United States Patent
Gulley et al.

(10) Patent No.: US 12,296,095 B2
(45) Date of Patent: May 13, 2025

(54) METHODS AND SYSTEMS FOR CONTROLLING OXYGEN DELIVERY IN A FLOW THERAPY APPARATUS

(71) Applicant: Fisher & Paykel Healthcare Limited, Auckland (NZ)

(72) Inventors: Anton Kim Gulley, Auckland (NZ); Russel William Burgess, Auckland (NZ); Bryn Alan Edwards, Auckland (NZ); Christopher Malcolm Crone, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 696 days.

(21) Appl. No.: 17/753,543

(22) PCT Filed: Sep. 10, 2020

(86) PCT No.: PCT/NZ2020/050101
§ 371 (c)(1),
(2) Date: Mar. 7, 2022

(87) PCT Pub. No.: WO2021/049954
PCT Pub. Date: Mar. 18, 2021

(65) Prior Publication Data
US 2022/0331548 A1    Oct. 20, 2022

Related U.S. Application Data

(60) Provisional application No. 62/898,464, filed on Sep. 10, 2019.

(51) Int. Cl.
*A61M 16/20*    (2006.01)
*A61M 16/00*    (2006.01)
(Continued)

(52) U.S. Cl.
CPC ...... *A61M 16/024* (2017.08); *A61M 16/1005* (2014.02); *A61M 16/125* (2014.02);
(Continued)

(58) Field of Classification Search
CPC ...... A61M 16/203–205; A61M 16/209; A61M 2016/0018; A61M 2016/0021;
(Continued)

(56) References Cited

U.S. PATENT DOCUMENTS 4,326,513 A    4/1982   Schulz et al.
4,889,116 A    12/1989  Taube
(Continued)

FOREIGN PATENT DOCUMENTS

AU    2011203234 A1    7/2011
CN    100522278 C      8/2009
(Continued)

OTHER PUBLICATIONS

International Search Report and Written Opinion of the International Searching Authority for International Application No. PCT/NZ2020/050101, mailed on Dec. 16, 2020, in 18 pages.

*Primary Examiner* — Bradley H Philips
*Assistant Examiner* — Kelsey Rhee
(74) *Attorney, Agent, or Firm* — Knobbe Martens Olson & Bear LLP

(57) ABSTRACT

The present disclosure provides for a control system for a flow therapy apparatus. The control system can control delivery of a fraction of delivered oxygen (FdO2) to a patient. The control system can maintain the FdO2 at a target level during a therapy session. The control system can automatically control an oxygen inlet valve in order to control the flow of oxygen to the patient.

12 Claims, 26 Drawing Sheets

(51) Int. Cl.
*A61M 16/10* (2006.01)
*A61M 16/12* (2006.01)
*F16K 31/06* (2006.01)
*G05D 16/20* (2006.01)
*G16H 20/40* (2018.01)

(52) U.S. Cl.
CPC .......... *A61M 16/204* (2014.02); *G16H 20/40* (2018.01); *A61M 2016/1025* (2013.01); *A61M 2202/0208* (2013.01); *F16K 31/0675* (2013.01); *G05D 16/2022* (2019.01); *G05D 16/208* (2013.01)

(58) Field of Classification Search
CPC ...... A61M 2016/1025; A61M 16/1005; A61M 16/021–026; A61M 16/12–122; A61M 16/125
See application file for complete search history.

(56) References Cited

U.S. PATENT DOCUMENTS

| | | | |
|---|---|---|---|
| 4,928,684 A | 5/1990 | Breitenfelder et al. | |
| 5,134,995 A | 8/1992 | Gruenke et al. | |
| 5,315,990 A | 5/1994 | Mondry | |
| 5,339,818 A | 8/1994 | Baker et al. | |
| 5,365,922 A | 11/1994 | Raemer | |
| 5,701,883 A | 12/1997 | Hete et al. | |
| 5,803,066 A | 9/1998 | Rapoport et al. | |
| 5,848,591 A | 12/1998 | Weismann | |
| 6,076,523 A | 6/2000 | Jones et al. | |
| 6,123,074 A | 9/2000 | Hete et al. | |
| 6,142,149 A | 11/2000 | Steen | |
| 6,148,814 A | 11/2000 | Clemmer et al. | |
| 6,186,142 B1 | 2/2001 | Schmidt et al. | |
| 6,371,114 B1 | 4/2002 | Schmidt et al. | |
| 6,397,655 B1 * | 6/2002 | Stephenson ........... F15B 19/002 73/1.72 | |
| 6,398,197 B1 | 6/2002 | Dickinson et al. | |
| 6,412,483 B1 | 7/2002 | Jones et al. | |
| 6,470,885 B1 | 10/2002 | Blue et al. | |
| 6,478,026 B1 | 11/2002 | Wood | |
| 6,512,938 B2 | 1/2003 | Claure et al. | |
| 6,532,958 B1 | 3/2003 | Buan et al. | |
| 6,561,187 B2 | 5/2003 | Schmidt et al. | |
| 6,644,312 B2 | 11/2003 | Berthon-Jones et al. | |
| 6,671,529 B2 | 12/2003 | Claure et al. | |
| 6,761,165 B2 | 7/2004 | Strickland, Jr. | |
| 6,796,305 B1 | 9/2004 | Banner et al. | |
| 6,839,581 B1 | 1/2005 | El-Solh et al. | |
| 6,845,773 B2 | 1/2005 | Berthon-Jones et al. | |
| 6,848,444 B2 | 2/2005 | Smith et al. | |
| 6,954,702 B2 | 10/2005 | Pierry et al. | |
| 7,008,380 B1 | 3/2006 | Rees et al. | |
| 7,066,173 B2 | 6/2006 | Banner et al. | |
| 7,089,937 B2 | 8/2006 | Berthon-Jones et al. | |
| 7,183,552 B2 | 2/2007 | Russell | |
| 7,210,478 B2 | 5/2007 | Banner et al. | |
| 7,222,624 B2 | 5/2007 | Rashad et al. | |
| 7,306,205 B2 | 12/2007 | Huddart et al. | |
| 7,331,343 B2 | 2/2008 | Schmidt et al. | |
| 7,415,297 B2 | 8/2008 | Al-Ali et al. | |
| 7,432,508 B2 | 10/2008 | Daniels et al. | |
| 7,501,630 B2 | 3/2009 | Russell | |
| 7,527,054 B2 | 5/2009 | Misholi | |
| 7,606,668 B2 | 10/2009 | Pierry et al. | |
| 7,607,437 B2 | 10/2009 | Boyle et al. | |
| 7,684,931 B2 | 3/2010 | Pierry et al. | |
| 7,736,132 B2 | 6/2010 | Bliss et al. | |
| 7,802,571 B2 | 9/2010 | Tehrani | |
| 8,066,647 B2 | 11/2011 | Armitstead | |
| 8,080,798 B2 | 12/2011 | Russell | |
| 8,091,547 B2 | 1/2012 | Thudor et al. | |
| 8,122,883 B2 | 2/2012 | Banner et al. | |
| 8,186,346 B2 | 5/2012 | Knight et al. | |
| 8,221,319 B2 | 7/2012 | Lovejoy | |
| 8,291,906 B2 | 10/2012 | Kooij et al. | |
| 8,333,194 B2 | 12/2012 | Lewis et al. | |
| 8,333,199 B2 | 12/2012 | Landis et al. | |
| 8,356,594 B2 | 1/2013 | Ujhazy et al. | |
| 8,386,083 B2 * | 2/2013 | Ding ................... G05D 7/0635 706/14 | |
| 8,397,725 B2 | 3/2013 | Slaker et al. | |
| 8,509,869 B2 | 8/2013 | Baker, Jr. et al. | |
| 8,522,782 B2 | 9/2013 | Lewis et al. | |
| 8,528,552 B2 | 9/2013 | von Blumenthal | |
| 8,544,467 B2 | 10/2013 | Berthon-Jones et al. | |
| 8,603,228 B2 | 12/2013 | Wilkinson et al. | |
| 8,616,207 B2 | 12/2013 | Wilkinson | |
| 8,640,699 B2 | 2/2014 | Baker, Jr. | |
| 8,640,700 B2 | 2/2014 | Baker, Jr. | |
| 8,667,963 B2 | 3/2014 | Sherman et al. | |
| 8,670,811 B2 | 3/2014 | O'Reilly | |
| 8,676,285 B2 | 3/2014 | Doyle et al. | |
| 8,689,788 B2 | 4/2014 | Rabi | |
| 8,721,542 B2 | 5/2014 | Al-Ali et al. | |
| 8,753,435 B2 | 6/2014 | Atlas et al. | |
| 8,770,192 B2 | 7/2014 | Tham | |
| 8,789,530 B2 | 7/2014 | Amjad et al. | |
| 8,852,094 B2 | 10/2014 | Al-Ali et al. | |
| 9,022,034 B2 | 5/2015 | Slaker et al. | |
| 9,089,657 B2 | 7/2015 | Kimm et al. | |
| 9,220,856 B2 | 12/2015 | Martin et al. | |
| 9,229,630 B2 | 1/2016 | Altas et al. | |
| 9,233,218 B2 | 1/2016 | Chapman et al. | |
| 9,254,368 B2 | 2/2016 | von Blumenthal | |
| 9,265,903 B2 | 2/2016 | Doyle et al. | |
| 9,283,341 B2 | 3/2016 | Ujhazy et al. | |
| 9,352,109 B2 | 5/2016 | Wittenber et al. | |
| 9,364,623 B2 | 6/2016 | Lellouche et al. | |
| 9,381,317 B2 | 7/2016 | Landis et al. | |
| 9,427,547 B2 | 8/2016 | Landis et al. | |
| 9,440,038 B2 | 9/2016 | Berthon-Jones et al. | |
| 9,616,192 B2 | 4/2017 | Chalvignac et al. | |
| 9,649,333 B2 | 5/2017 | Rabi | |
| 9,669,172 B2 | 6/2017 | Cullen et al. | |
| 9,931,484 B2 | 4/2018 | Thomas et al. | |
| 9,937,308 B2 | 4/2018 | Garde et al. | |
| 9,956,371 B2 | 5/2018 | DeVries et al. | |
| 10,046,134 B2 | 8/2018 | DeVries et al. | |
| 10,065,008 B2 | 9/2018 | Cullen et al. | |
| 10,098,591 B2 | 10/2018 | Al-Ali et al. | |
| 10,105,509 B2 | 10/2018 | DeVries et al. | |
| 10,238,823 B2 | 3/2019 | Ahmad | |
| 10,245,406 B2 | 4/2019 | DeVries et al. | |
| 10,252,020 B2 | 4/2019 | Wondka et al. | |
| 10,272,219 B2 | 4/2019 | Santhana Naidu et al. | |
| 10,315,002 B2 | 6/2019 | DeVries et al. | |
| 10,335,571 B2 | 7/2019 | Chalvignac et al. | |
| 10,357,629 B2 | 7/2019 | Barker et al. | |
| 10,398,862 B2 | 9/2019 | Martin et al. | |
| 10,398,870 B2 | 9/2019 | Chapman et al. | |
| 10,512,429 B2 | 12/2019 | Lau et al. | |
| 10,518,059 B2 | 12/2019 | Cipollone et al. | |
| 10,576,237 B2 | 3/2020 | DeVries et al. | |
| 10,617,836 B2 | 4/2020 | Kagan | |
| 10,675,427 B2 | 6/2020 | Landis et al. | |
| 10,718,447 B2 * | 7/2020 | Jagoda ................... E02F 9/2267 | |
| 10,751,490 B2 | 8/2020 | Martin et al. | |
| 10,758,699 B2 | 9/2020 | Cipollone et al. | |
| 10,821,259 B2 | 11/2020 | Borrello | |
| 10,835,699 B2 | 11/2020 | Albanese et al. | |
| 10,856,750 B2 | 12/2020 | Indorf et al. | |
| 10,856,802 B2 | 12/2020 | Ujhazy et al. | |
| 10,869,987 B2 | 12/2020 | Elliott et al. | |
| 10,980,967 B2 | 4/2021 | Barker et al. | |
| 10,987,066 B2 | 4/2021 | Chandran et al. | |
| 11,065,408 B2 | 7/2021 | Lellouche et al. | |
| 11,071,464 B2 | 7/2021 | Landis et al. | |
| 11,109,814 B2 | 9/2021 | Al-Ali et al. | |
| 11,123,511 B2 | 9/2021 | Creusot et al. | |
| 11,135,384 B2 | 10/2021 | Gale et al. | |
| 11,160,941 B2 | 11/2021 | Holley et al. | |
| 11,185,655 B2 | 11/2021 | Cipollone et al. | |

(56) References Cited

U.S. PATENT DOCUMENTS

| | | |
|---|---|---|
| 11,291,791 B2 | 4/2022 | DeVries et al. |
| 11,344,692 B2 | 5/2022 | Cipollone et al. |
| 11,351,330 B2 | 6/2022 | Leonard et al. |
| 11,351,334 B2 | 6/2022 | Chalvignac et al. |
| 2004/0159323 A1 | 8/2004 | Schmidt et al. |
| 2005/0098527 A1 | 5/2005 | Yates, III |
| 2006/0084877 A1 | 4/2006 | Ujhazy et al. |
| 2006/0102581 A1 | 5/2006 | Yates, III |
| 2006/0108363 A1 | 5/2006 | Yates, III |
| 2006/0213519 A1 | 9/2006 | Schmidt et al. |
| 2006/0237015 A1 | 10/2006 | Berthon-Jones et al. |
| 2007/0000494 A1 | 1/2007 | Banner et al. |
| 2007/0044799 A1 | 3/2007 | Hete et al. |
| 2007/0107737 A1 | 5/2007 | Landis et al. |
| 2007/0135724 A1 | 6/2007 | Ujhazy et al. |
| 2007/0221225 A1 | 9/2007 | Kutt et al. |
| 2008/0000866 A1 | 1/2008 | Yates, III |
| 2008/0058667 A1 | 3/2008 | Pierry et al. |
| 2008/0066752 A1 | 3/2008 | Baker et al. |
| 2008/0076962 A1 | 3/2008 | Miyagawa et al. |
| 2008/0142012 A1 | 6/2008 | Farnsworth et al. |
| 2008/0295839 A1 | 12/2008 | Habashi |
| 2009/0007911 A1 | 1/2009 | Cleary et al. |
| 2009/0227852 A1 | 9/2009 | Glaser |
| 2009/0320836 A1 | 12/2009 | Baker, Jr. |
| 2010/0137729 A1 | 6/2010 | Pierry et al. |
| 2010/0224191 A1 | 9/2010 | Dixon et al. |
| 2010/0224192 A1 | 9/2010 | Dixon et al. |
| 2010/0258126 A1 | 10/2010 | Ujhazy et al. |
| 2012/0000462 A1 | 1/2012 | Edwards et al. |
| 2012/0016218 A1 | 1/2012 | Lau et al. |
| 2012/0055474 A1 | 3/2012 | Wilkinson |
| 2012/0055475 A1 | 3/2012 | Wilkinson |
| 2012/0055477 A1 | 3/2012 | Wilkinson |
| 2012/0055478 A1 | 3/2012 | Wilkinson |
| 2012/0055480 A1 | 3/2012 | Wilkinson |
| 2012/0055483 A1 | 3/2012 | Wilkinson et al. |
| 2012/0088992 A1 | 4/2012 | Armitstead |
| 2012/0090611 A1 | 4/2012 | Graboi et al. |
| 2012/0107423 A1 | 5/2012 | Goldstein |
| 2012/0204870 A1 | 8/2012 | McAuley et al. |
| 2013/0152933 A1 | 6/2013 | Lischer et al. |
| 2013/0239961 A1 | 9/2013 | Ross, Jr. et al. |
| 2013/0245973 A1 | 9/2013 | Ross, Jr. et al. |
| 2013/0345532 A1 | 12/2013 | Doyle et al. |
| 2014/0202455 A1 | 7/2014 | Garde et al. |
| 2014/0275901 A1 | 9/2014 | Flanagan et al. |
| 2014/0318536 A1 | 10/2014 | Landis et al. |
| 2015/0018648 A1 | 1/2015 | Boyer et al. |
| 2015/0059745 A1* | 3/2015 | Barker ............... A61M 16/20 128/203.14 |
| 2015/0087936 A1 | 3/2015 | Al-Ali et al. |
| 2015/0208968 A1 | 7/2015 | Ennett et al. |
| 2016/0022952 A1 | 1/2016 | Brown |
| 2016/0058850 A1 | 3/2016 | Igonin et al. |
| 2016/0058933 A1* | 3/2016 | Ballantyne ........... G06F 21/565 210/85 |
| 2016/0121070 A1 | 5/2016 | Chapman et al. |
| 2016/0166797 A1* | 6/2016 | Orr .................. A61M 16/0677 128/204.23 |
| 2016/0287824 A1 | 10/2016 | Chang |
| 2016/0296721 A1 | 10/2016 | Landis et al. |
| 2016/0303405 A1 | 10/2016 | Elliott et al. |
| 2016/0317765 A1 | 11/2016 | Rees et al. |
| 2016/0367776 A1 | 12/2016 | Landis et al. |
| 2016/0367779 A1 | 12/2016 | Landis et al. |
| 2017/0182278 A1 | 6/2017 | Allen |
| 2017/0232221 A1 | 8/2017 | Kepler et al. |
| 2018/0099109 A1 | 4/2018 | Kinsky et al. |
| 2018/0125430 A1 | 5/2018 | Al-Ali et al. |
| 2018/0206795 A1 | 7/2018 | Al-Ali |
| 2019/0029578 A1 | 1/2019 | Al-Ali et al. |
| 2019/0134340 A1 | 5/2019 | Nebrigac |
| 2019/0201647 A1 | 7/2019 | Truschel et al. |
| 2019/0216377 A1 | 7/2019 | Flanagan et al. |
| 2019/0262572 A1 | 8/2019 | DeVries et al. |
| 2019/0275273 A1 | 9/2019 | Chang |
| 2019/0344030 A1 | 11/2019 | Martin et al. |
| 2020/0060628 A1 | 2/2020 | Al-Ali et al. |
| 2020/0297961 A1 | 9/2020 | Landis et al. |
| 2020/0345961 A1 | 11/2020 | Martin et al. |
| 2020/0384238 A1 | 12/2020 | Blunsden |
| 2021/0145300 A1 | 5/2021 | Indorf et al. |
| 2021/0187222 A1 | 6/2021 | Dickens et al. |
| 2021/0212640 A1 | 7/2021 | Chandran et al. |
| 2021/0322710 A1 | 10/2021 | Barker et al. |
| 2021/0346633 A1 | 11/2021 | Creusot et al. |
| 2021/0353221 A1 | 11/2021 | Armitstead |
| 2021/0353893 A1 | 11/2021 | Landis et al. |
| 2021/0361893 A1 | 11/2021 | Holley et al. |
| 2021/0361899 A1 | 11/2021 | Williams et al. |
| 2022/0054093 A1 | 2/2022 | Al-Ali et al. |

FOREIGN PATENT DOCUMENTS

| | | |
|---|---|---|
| CN | 108066862 A | 5/2018 |
| EP | 0876176 B1 | 12/2006 |
| EP | 2374490 A2 | 10/2011 |
| EP | 1653905 B1 | 6/2016 |
| EP | 3400984 A1 | 11/2018 |
| EP | 2682147 B1 | 3/2019 |
| WO | WO 2004/032719 A1 | 4/2004 |
| WO | WO 2005/013879 A2 | 2/2005 |
| WO | WO 2006/055508 A2 | 5/2006 |
| WO | WO 2007/033271 A1 | 3/2007 |
| WO | WO 2007/103855 A2 | 9/2007 |
| WO | WO 2009/115944 A1 | 9/2009 |
| WO | WO 2009/115948 A1 | 9/2009 |
| WO | WO 11/029074 | 3/2011 |
| WO | WO 2011/150260 A1 | 12/2011 |
| WO | WO 14/142681 | 9/2014 |
| WO | WO 15/192186 | 12/2015 |
| WO | WO 2016/157104 A1 | 10/2016 |
| WO | WO 2017/059530 A1 | 4/2017 |
| WO | WO 2018/208802 A1 | 11/2018 |
| WO | WO 2019/070136 A1 | 4/2019 |
| WO | WO 2019/112447 A1 | 6/2019 |

* cited by examiner

METHODS AND SYSTEMS FOR CONTROLLING OXYGEN DELIVERY IN A FLOW THERAPY APPARATUS

CROSS-REFERENCE TO RELATED APPLICATIONS

This application is the U.S. National Phase under 35 U.S.C. § 371 of International Application PCT/NZ2020/050101, filed Sep. 10, 2020, which claims priority to U.S. Application No. 62/898,464, filed Sep. 10, 2019, the entire contents of each of which are incorporated by reference herein and made a part of this specification.

FIELD OF THE DISCLOSURE

The present disclosure relates to methods and systems for controlling oxygen delivery in a flow therapy apparatus.

BACKGROUND

Respiratory apparatuses are used in various environments such as hospital, medical facility, residential care, or home environments to deliver a flow of gas to users or patients. A respiratory apparatus, or a flow therapy apparatus, may include an oxygen inlet to allow delivery of supplemental oxygen with the flow of gas, and/or a humidification apparatus to deliver heated and humidified gases. A flow therapy apparatus may allow adjustment and control over characteristics of the gases flow, including flow rate, temperature, gas concentration, such as oxygen concentration, humidity, pressure, etc.

SUMMARY

In accordance with certain features, aspects and advantages of a first embodiment disclosed herein, a respiratory apparatus that provides a flow of gases to a patient, the respiratory apparatus comprising: an ambient air inlet; a supplemental inlet for receiving supplemental gases from a supplemental gases source; a valve configured to control a flow rate of the supplemental gases received through the supplemental gases inlet; a flow rate sensor configured to measure a total flow rate of gases delivered to the patient; a controller configured to control delivery of gases to the patient, the controller configured to: determine a target supplemental gases flow rate based at least in part on the total flow rate; and set a valve current based on the target supplemental gases flow rate.

In some configurations of the first embodiment, the supplemental gases comprise concentrated oxygen.

In some configurations of the first embodiment, the controller is configured to determine the target supplemental gases flow rate based at least in part on a target fraction of delivered oxygen (FdO2).

In some configurations of the first embodiment, the controller is configured to determine the target supplemental gases flow rate based at least in part on a fraction of oxygen of ambient air.

In some configurations of the first embodiment, the controller is configured to determine the target supplemental gases flow rate based at least in part on a fraction of oxygen of the supplemental gas source.

In some configurations of the first embodiment, the controller is configured to set the valve current based on the target supplemental gas flow using a valve model.

In some configurations of the first embodiment, the valve model is updated over time.

In some configurations of the first embodiment, the valve model is updated based in part on the measured FdO2.

In some configurations of the first embodiment, the valve model is updated based in part on the total flow rate.

In some configurations of the first embodiment, the valve model is updated based in part on a target FdO2.

In some configurations of the first embodiment, the valve model includes an estimate of a minimum current required to open the valve.

In some configurations of the first embodiment, the estimate of the minimum current required to open the valve is updated over time.

In some configurations of the first embodiment, the valve model includes an estimate of the flow rate of the supplemental gases through the valve.

In some configurations of the first embodiment, the estimate of the flow rate of the supplemental gases through the valve is determined using at least one of a first order model, an advection diffusion equation, a naiver stokes equation, or machine learning algorithms.

In accordance with certain features, aspects and advantages of a second embodiment disclosed herein, a respiratory apparatus that provides a flow of gases to a patient, the respiratory apparatus comprising: an ambient air inlet; a supplemental inlet for receiving supplemental gases from a supplemental gases source; a valve configured to control a flow rate of the supplemental gases received through the supplemental gases inlet; a gases composition sensor configured to measure gases composition of mixed flow of ambient air and supplemental gases; a controller configured to control delivery of gases to the patient, the controller configured to: adjust actuation of the valve by controlling a valve current; determine a target supplemental gases flow rate; set the valve current based on the target supplemental gases flow rate using a valve model; and update valve model over time based in part on measurements received from the gases composition sensor.

In some configurations of the second embodiment, the supplemental gases comprise concentrated oxygen.

In some configurations of the second embodiment, the valve model is updated over time based in part on predicted changes in the measured gases composition.

In some configurations of the second embodiment, the predicted changes in the measured gases composition are based at least in part on a current valve position and a current flow rate.

In some configurations of the second embodiment, the gases composition measurement is a measured fraction of delivered oxygen (FdO2).

In some configurations of the second embodiment, the valve model is updated over time based in part on a target gases composition.

In some configurations of the second embodiment, the target gases composition is a target FdO2.

In some configurations of the second embodiment, the valve model is updated over time based in part on predicted changes in the gases composition.

In some configurations of the second embodiment, the predicted changes in the gases composition are based at least in part on the recent trend in measured gases composition.

In some configurations of the second embodiment, the valve model includes an estimate of a minimum current required to open the valve.

In some configurations of the second embodiment, the estimate of the minimum current required to open the valve is updated over time.

In some configurations of the second embodiment, the respiratory apparatus further includes a flow rate sensor configured to measure a total flow rate.

In some configurations of the second embodiment, the controller determines the target supplemental gases flow rate based at least in part on the total flow rate.

In some configurations of the second embodiment, the controller determines target supplemental gases flow rate based at least in part on target FdO2.

In some configurations of the second embodiment, the controller determines target supplemental gases flow rate based at least in part on the fraction of oxygen of the ambient air.

In some configurations of the second embodiment, the controller determines target supplemental gases flow rate based at least in part on the fraction of oxygen of the supplemental gas source.

In some configurations of the second embodiment, the controller updates the valve model at different rates depending on expected respiration rate ranges.

In some configurations of the second embodiment, the controller updates the valve model at different rates depending on expected amplitudes of flow rate oscillations.

In some configurations of the second embodiment, the controller updates the valve model at different rates depending on the flow rate.

In some configurations of the second embodiment, the controller updates the valve model using a feedback loop.

In some configurations of the second embodiment, the coefficients of the feedback loop are adjusted based in part on flow rate.

In some configurations of the second embodiment, the valve model includes an estimate of the flow rate of the supplemental gases through the valve.

In some configurations of the second embodiment, the estimate of the flow rate of the supplemental gases through the valve is determined using at least one of a first order model, an advection diffusion equation, a naiver stokes equation, or machine learning algorithms.

In accordance with certain features, aspects and advantages of a third embodiment disclosed herein, a respiratory apparatus that provides a flow of gases to a patient, the respiratory apparatus comprising: an ambient air inlet; a supplemental inlet for receiving supplemental gases from a supplemental gases source; a valve, wherein the valve requires a minimum amount of current in order to open; a gases composition sensor configured to measure gases composition of mixed flow of ambient air and supplemental gases; a main controller configured to control delivery of gases to the patient, the controller configured to: adjust actuation of a valve opening by controlling valve current; and activate a coarse controller when a target flow rate of supplemental gas is increased from zero; a coarse controller configured to: control actuation of the valve opening by controlling the valve current, wherein the main controller or the coarse controller can control the valve current; iteratively increases current supplied to the valve; and switch control of the actuation of the valve to the main controller after flow through the valve is detected.

In some configurations of the third embodiment, prior to iteratively increasing the valve current, the controller sets the valve current at an initial value.

In some configurations of the third embodiment, the initial value corresponds to the minimum possible current required to open the valve opening of the valve.

In some configurations of the third embodiment, at each iteration of the coarse controller, the controller executes a step change in the valve current.

In some configurations of the third embodiment, the size of step change increases at each iteration.

In some configurations of the third embodiment, the size of step change is based at least in part on a target FdO2.

In some configurations of the third embodiment, the size of step change is based at least in part on total flow rate.

In some configurations of the third embodiment, the respiratory apparatus includes a gases composition sensor.

In some configurations of the third embodiment, flow through the valve is detected using the gases composition sensor.

In some configurations of the third embodiment, flow through the valve is determined to be occurring when the concentration of supplemental gas exceeds ambient levels.

In some configurations of the third embodiment, flow through the valve is determined to be occurring when the concentration of supplemental gas exceeds ambient levels by an amount greater than the potential sensor error.

In some configurations of the third embodiment, the supplemental gases comprise concentrated oxygen.

In accordance with certain features, aspects and advantages of a fourth embodiment disclosed herein, a respiratory apparatus that provides a flow of gases to a patient, the respiratory apparatus comprising: a display; an ambient air inlet; a supplemental inlet for receiving supplemental gases from a supplemental gases source; a valve; a gases composition sensor configured to measure gases composition of mixed flow of ambient air and supplemental gases; a controller configured to control delivery of gases to the patient: receive input of target gases composition; adjust actuation of the valve to control gases composition; display target gases composition while in a target mode; display measured gases composition while in a measured mode; monitor difference between target gases composition and measured gases composition; change from the target mode to the measured mode when the difference exceeds a first threshold; and change from the measured mode to the target mode when the difference falls below a second threshold.

In some configurations of the fourth embodiment, the supplemental gases comprise concentrated oxygen.

In some configurations of the fourth embodiment, the gases composition measurement is a measured fraction of delivered oxygen (FdO2).

In some configurations of the fourth embodiment, the gases composition sensor comprises acoustic transducers.

In some configurations of the fourth embodiment, the first threshold is determined in part based on the target gases composition.

In some configurations of the fourth embodiment, the second threshold is determined in part based on the target gases composition.

In some configurations of the fourth embodiment, the first threshold is equal to the second threshold.

In some configurations of the fourth embodiment, the first threshold is above the second threshold.

In accordance with certain features, aspects and advantages of a fifth embodiment disclosed herein, a respiratory apparatus comprising; an ambient air inlet for receiving a flow of ambient air; a supplemental inlet for receiving supplemental gases from a supplemental gases source; a valve; a controller configured to control delivery of gases to the patient, the controller configured to: adjust a valve position to control a flow rate of supplemental gases added to the flow of ambient air; calculate a first level, wherein the first level represents a flow rate of supplemental gases required to achieve a target gases composition for a current total flow rate of gases; calculate a second level, wherein the second level represents a flow rate of supplemental gases, the second level being lower than the first level; calculate a third level, wherein the third level represents a flow rate of supplemental gases, the third level being higher than the first level; analyze a breath cycle of the patient, the breath cycle including consecutive respiratory periods, each respiratory period comprising an inspiratory period and an expiratory period; control the valve to deliver the first level of supplemental gases during a first portion of each of the patient's respiratory periods; control the valve to deliver the second level of supplemental gases during a second portion of each of the patient's respiratory periods; and control the valve to deliver the third level of supplemental gases during a third portion of each of the patient's respiratory periods.

In some configurations of the fifth embodiment, the supplemental gas comprises oxygen.

In some configurations of the fifth embodiment, the target gases composition is a target fraction of delivered oxygen (FdO2).

In some configurations of the fifth embodiment, the supplemental gas comprises an aerosolized medicament.

In some configurations of the fifth embodiment, the target gases composition is a target aerosolized medicament concentration.

In some configurations of the fifth embodiment, the respiratory apparatus includes a flow generator.

In some configurations of the fifth embodiment, the flow generator comprises a blower.

In some configurations of the fifth embodiment, the controller is further configured to control the flow generator to deliver a target flow rate.

In some configurations of the fifth embodiment, the controller is further configured to control the flow generator to deliver a flow rate that meets or exceeds a patient's inspiratory demand.

In some configurations of the fifth embodiment, the apparatus provides nasal high flow therapy.

In some configurations of the fifth embodiment, the first portion of the respiratory period includes at least a portion of the inspiratory period of the respiratory period.

In some configurations of the fifth embodiment, the second portion of the respiratory period includes at least a portion of the start of the expiratory period of the respiratory period.

In some configurations of the fifth embodiment, the third portion of the respiratory period includes at least a portion of the end of the expiratory period of the respiratory period.

In some configurations of the fifth embodiment, the controller is further configured to account for a travel time of gases within a respiratory circuit between the valve and a patient interface when switching between the first, second, and/or third levels.

In some configurations of the fifth embodiment, the controller is further configured to estimate the travel time between the valve and the patient interface.

In some configurations of the fifth embodiment, the controller is further configured to estimate the travel time between the valve and the patient interface based on the current total flow rate of gases.

In some configurations of the fifth embodiment, the second level is a set fraction of the first level.

In some configurations of the fifth embodiment, the second level corresponds to no flow of supplemental gases being delivered to the flow of ambient air.

In some configurations of the fifth embodiment, the third level is a set multiple of the first level.

In some configurations of the fifth embodiment, the third level corresponds to a maximum flow rate of supplemental gases.

In some configurations of the fifth embodiment, the controller is further configured to calculate a first value that is a defined multiple of the first level and a second value that is a maximum flow rate of supplemental gases, and set the third level at the lower of the first value or the second value.

In some configurations of the fifth embodiment, the maximum flow rate of supplemental gases is determined based on the total flow rate.

In some configurations of the fifth embodiment, the controller is further configured to calculate a running average of total supplemental gases supplied throughout the respiratory period, and generates a conservation metric by comparing the running average of total supplemental gases with an estimated amount of supplemental gas that would be used if the valve were controlled to continuously deliver the first level of supplemental gas.

In some configurations of the fifth embodiment, the respiratory apparatus is configured to display the conservation metric on a graphical user interface of a display of the respiratory apparatus.

In some configurations of the fifth embodiment, the controller is configured to switch to continuously controlling the valve to deliver the first level of supplemental gas if the conservation metric does not satisfy a conservation threshold.

In some configurations of the fifth embodiment, the controller is further configured to adjust a length of time for which at least one of the first, second, or third level is set.

In some configurations of the fifth embodiment, the controller is further configured to adjust the length of time based at least in part on the flow rate.

In some configurations of the fifth embodiment, the controller is further configured to adjust the length of time based at least in part on the patient's respiratory rate.

In some configurations of the fifth embodiment, the controller is further configured to adjust the length of time for which the third level of supplemental gases is delivered based at least in part on the difference between the first level and the second level.

In accordance with certain features, aspects and advantages of a sixth embodiment disclosed herein, a respiratory apparatus comprising; an ambient air inlet for receiving a flow of ambient air; a supplemental inlet for receiving supplemental gases from a supplemental gases source; a valve; a controller configured to control delivery of gases to the patient, the controller configured to: adjust a valve position to control a flow rate of supplemental gases added to the flow of ambient air; calculate a first level, wherein the first level represents a flow rate of supplemental gases required to achieve a target gases composition for a current total flow rate of gases; calculate a second level, wherein the second level represents a flow rate of supplemental gases, the second level being lower than the first level; analyze a breath cycle of the patient, the breath cycle including consecutive respiratory periods, each respiratory period comprising an inspiratory period and an expiratory period; and determine the suitability of a first mode of operation or a second mode of operation based on one or more operation parameters and/or patient parameters; and automatically select the first mode of operation or the second mode of operation based on the determination; wherein, in the first mode of operation, the valve is continuously controlled to deliver the first level of supplemental gases flow throughout the entirety of the patient's respiratory period; wherein, in the second mode of operation, the valve is controlled to deliver the first level of supplemental gases flow during a first portion of the patient's respiratory period, and to deliver the second level of supplemental gases flow during a second portion of the patient's respiratory period.

In some configurations of the sixth embodiment, the controller is further configured to determine the patient's respiratory period.

In some configurations of the sixth embodiment, the determination of the patient's respiratory period comprises a determination of the patient's respiratory rate and respiratory phase.

In some configurations of the sixth embodiment, the determination of the patient's respiratory period includes a respiratory confidence metric, wherein the respiratory confidence metric represents the confidence that the determination of the patient's respiratory rate and/or respiratory phase is correct.

In some configurations of the sixth embodiment, the controller is further configured to select the mode of operation based at least in part on the respiratory confidence metric.

In some configurations of the sixth embodiment, the controller is further configured to compare the respiratory confidence metric with a threshold, and automatically select the first mode of operation if the respiratory confidence metric is below the threshold.

In some configurations of the sixth embodiment, the determination of the suitability of the first mode of operation or the second mode of operation comprises comparing a patient's respiratory rate with a threshold.

In some configurations of the sixth embodiment, the determination of the suitability of the first mode of operation or the second mode of operation comprises comparing a patient's respiratory rate with a threshold, and automatically selecting the first mode if the patient's respiratory rate is above the threshold.

In some configurations of the sixth embodiment, the determination of the suitability of the first mode of operation or the second mode of operation comprises comparing flow rate with a threshold.

In some configurations of the sixth embodiment, the determination of the suitability of the first mode of operation or the second mode of operation comprises comparing flow rate with a threshold, and automatically selecting the first mode if the flow rate is below the threshold.

In some configurations of the sixth embodiment, the determination of the suitability of the first mode of operation or the second mode of operation comprises calculating a ratio of the patient's respiratory rate to the flow rate and comparing the ratio with a threshold.

In some configurations of the sixth embodiment, the determination of the suitability of the first mode of operation or the second mode of operation comprises calculating a ratio of the patient's respiratory rate to the flow rate, comparing the ratio with a threshold, and automatically selecting the first mode of operation if the ratio satisfies the threshold.

In some configurations of the sixth embodiment, the controller is further configured to estimate the average amount of supplemental gas that would be used in the first mode and the second mode, generate a conservation metric by comparing the two values, and select the operation mode based at least partially on the value of the conservation metric.

In some configurations of the sixth embodiment, the first portion of the respiratory period includes at least a portion of the inspiratory period of the respiratory period.

In some configurations of the sixth embodiment, the second portion of the respiratory period includes at least a portion of the start of the expiratory period of the respiratory period.

In some configurations of the sixth embodiment, the controller is further configured to calculate a third level, wherein the third level represents a flow rate of supplemental gases, the third level being higher than the first level.

In some configurations of the sixth embodiment, the controller is further configured to, in the second mode of operation, control the valve to deliver the third level of supplemental gases during a third portion of the patient's respiratory period.

In some configurations of the sixth embodiment, the third portion of the respiratory period includes at least a portion of the end of the expiratory period of the respiratory period.

In some configurations of the sixth embodiment, the controller is further configured to account for a travel time of gases within a respiratory circuit between the valve and a patient interface when switching between the first, second, and/or third levels.

In some configurations of the sixth embodiment, the third level is a set multiple of the first level.

In some configurations of the sixth embodiment, the third level corresponds to a maximum flow rate of supplemental gases.

In some configurations of the sixth embodiment, the controller is further configured to calculate a first value that is a defined multiple of the first level and a second value that is a maximum flow rate of supplemental gases, and set the third level at the lower of the first value or the second value.

In some configurations of the sixth embodiment, the controller is further configured to adjusts a length of time for which at least one of the first, second, or third levels is set.

In some configurations of the sixth embodiment, the controller is further configured to adjusts the length of time based at least in part on the flow rate.

In some configurations of the sixth embodiment, the controller is further configured to adjust the length of time based at least in part on the patient's respiratory rate.

In some configurations of the sixth embodiment, the controller is further configured to adjust the length of time for which the third level of supplemental gases is delivered based at least in part on the difference between the first level and the second level.

In some configurations of the sixth embodiment, the supplemental gas comprises oxygen.

In some configurations of the sixth embodiment, the target gases composition is a target fraction of delivered oxygen (FdO2).

In some configurations of the sixth embodiment, the controller is further configured to determine the suitability of the first mode or the second mode of operation at a determined interval of time.

In some configurations of the sixth embodiment, the determined interval of time is based on the one or more operation parameters and/or the patient parameters.

Features from one or more embodiments or configurations may be combined with features of one or more other embodiments or configurations. Additionally, more than one embodiment may be used together during a process of respiratory support of a patient.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

DETAILED DESCRIPTION

Figure 1A:
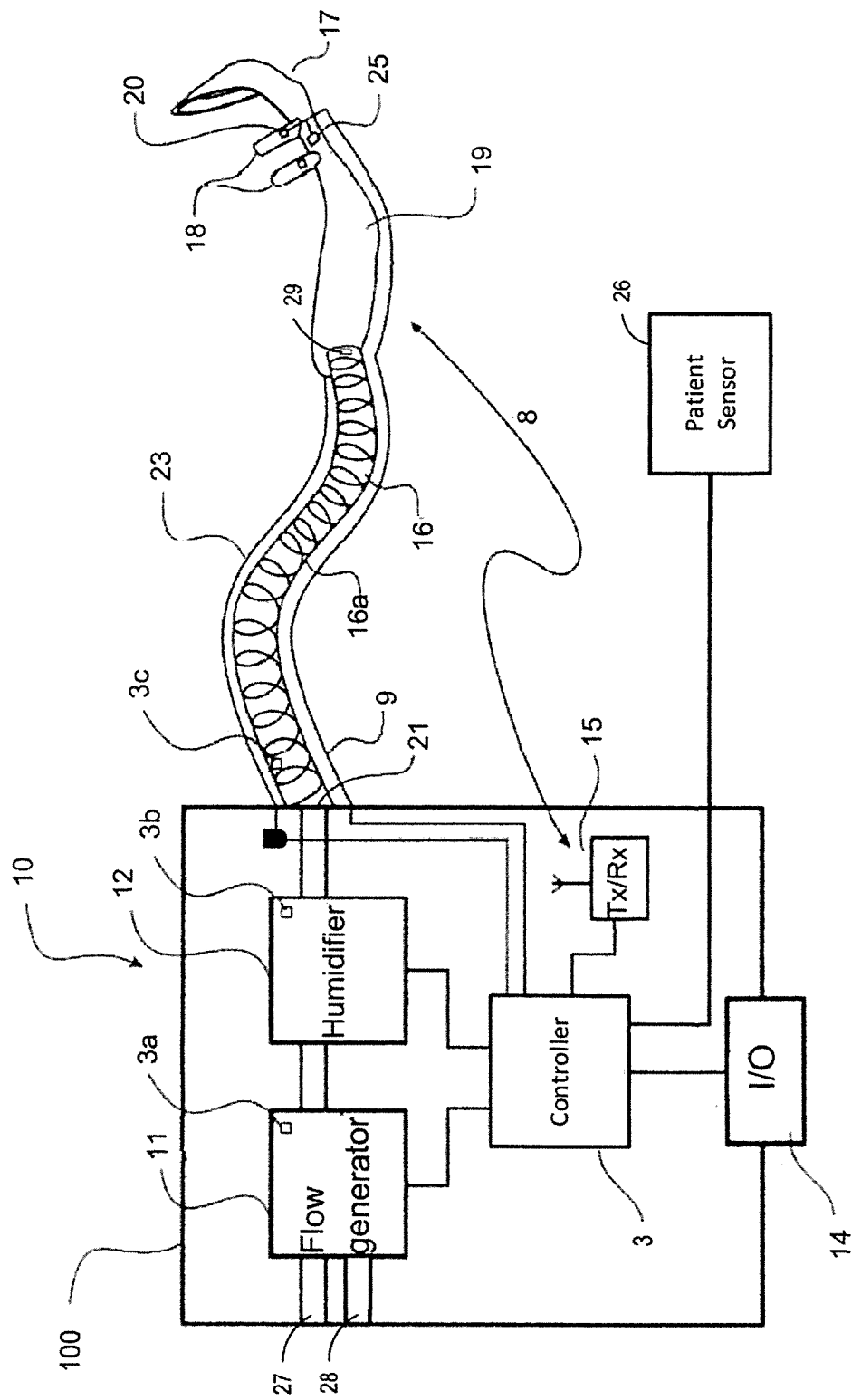
FIG. 1A shows in diagrammatic form a flow therapy apparatus.

Patients suffering from various health conditions and diseases can benefit from oxygen therapy. For example, patients suffering from chronic obstructive pulmonary disease (COPD), pneumonia, asthma, bronchopulmonary dysplasia, heart failure, cystic fibrosis, sleep apnea, lung disease, trauma to the respiratory system, acute respiratory distress, receiving pre- and post-operative oxygen delivery, and other conditions or diseases can benefit from oxygen therapy. A common way of treating such problems is by supplying the patients with supplemental oxygen to prevent their blood oxygen saturation (SpO2) from dropping too low (e.g., below about 90%). However, supplying the patient with too much oxygen can over oxygenate their blood, and is also considered dangerous. Generally, the patient's SpO2 is kept in a range from about 80% to about 99%, and preferably about 92% to about 96%, although these ranges may differ due to patient conditions. Due to various factors such as respiratory rate, lung tidal volume, heart rate, activity levels, height, weight, age, gender, and other factors, there is no one prescribed level of supplemental oxygen that can consistently achieve an SpO2 response in the targeted range for each patient. Individual patients will regularly need their fraction of oxygen delivered to the patient (FdO2) monitored and adjusted to ensure they are receiving the correct FdO2 to achieve the targeted SpO2. Achieving a correct and consistent SpO2 is an important factor in treating patients with various health conditions or diseases. Additionally, patients suffering from these health problems may find benefit from a system that automatically controls oxygen saturation. The present disclosure is applicable to a wide range of patients that require fast and accurate oxygen saturation control.

The fraction of oxygen delivered to a patient (FdO2) may be controlled manually. A clinician can manually adjust an oxygen supply valve to change the flow rate or fraction of oxygen being delivered to the patient. The clinician can determine SpO2 levels of the patient using a patient monitor, such as a pulse oximeter. The clinician can continue to manually adjust the amount of oxygen being delivered to the patient until the SpO2 level of the patient reaches a determined level.

One problem with current methods is that it can be difficult to manually maintain a target FdO2. Additionally, the clinician cannot constantly adjust the valve to account for a flow rate is that is fluctuating, such as over the course of the breath of the patient.

The present disclosure provides for a system of FdO2 control that allows for automatic control of a valve such that a target FdO2 can be consistently achieved, even if the total flow rate is fluctuating, such as over the course of a breath. The system can also allow a user to set a target FdO2 more easily, as well as maintaining a target FdO2 despite changes in flow rate without requiring further input form the user. The FdO2 control system can also be used to more effectively execute a closed loop SpO2 control algorithm.

The present disclosure provides for a control system for a flow therapy apparatus. The control system can be configured to ensure that the instantaneous FdO2 is maintained at a target level at substantially all points during a therapy session. The open loop control system uses the measured total flow rate and certain gas properties to determine a target flow rate through a supplemental gas inlet valve, such as an oxygen control valve. The target valve flow rate is based on the flow rate that would be required to achieve a target FdO2 for the patient. The flow therapy apparatus can use the target valve flow rate and certain assumed valve properties to set the valve current. The valve current can control the actuation of the valve, which in turn controls the flow rate of gases through the supplemental valve. The flow therapy apparatus can use the target valve flow rate and an estimate of the actual valve flow rate to adjust the assumed valve properties.

In some configurations, the flow therapy apparatus can use multiple controllers. A coarse controller can be used to quickly find the required minimum current to open the oxygen control valve, and then control of the valve can be transferred to a main controller once the required minimum current has been determined. The main controller can determine a measure of effective FdO2 based on the average FdO2 across a breath.

The controller can continuously determine a measure of effective FdO2. The flow therapy apparatus can then alternate between displaying the target FdO2 and the effective FdO2 based on the difference between the two values. The controller can determine whether the effective FdO2 is sufficiently close to the target FdO2. When the device is displaying the effective FdO2, it would switch to displaying the target FdO2 if the difference falls below a first threshold. When the device is displaying target FdO2, it would switch to displaying effective FdO2 if the difference exceeds a second threshold.

Flow Therapy Apparatus

A flow therapy apparatus 10 is shown in FIG. 1A. The apparatus 10 can comprise a main housing 100 that contains a flow generator 11 in the form of a motor/impeller arrangement (for example, a blower), an optional humidifier 12, a controller 13, and a user interface 14 (comprising, for example, a display and input device(s) such as button(s), a touch screen, or the like). The controller 13 can be configured or programmed to control the operation of the apparatus. For example, the controller can control components of the apparatus, including but not limited to: operating the flow generator 11 to create a flow of gas (gases flow) for delivery to a patient, operating the humidifier 12 (if present) to humidify and/or heat the generated gases flow, control a flow of oxygen into the flow generator blower, receiving user input from the user interface 14 for reconfiguration and/or user-defined operation of the apparatus 10, and outputting information (for example on the display) to the user. The user can be a patient, healthcare professional, or anyone else interested in using the apparatus. As used herein, a "gases flow" can refer to any flow of gases that may be used in the breathing assistance or respiratory device, such as a flow of ambient air, a flow comprising substantially 100% oxygen, a flow comprising some combination of ambient air and oxygen, and/or the like.

A patient breathing conduit 16 is coupled at one end to a gases flow outlet 21 in the housing 100 of the flow therapy apparatus 10. The patient breathing conduit 16 is coupled at another end to a patient interface 17 such as a non-sealed nasal cannula with a manifold 19 and nasal prongs 18. Additionally, or alternatively, the patient breathing conduit 16 can be coupled to a face mask, a nasal mask, a nasal pillows mask, an endotracheal tube, a tracheostomy interface, and/or the like. The gases flow that is generated by the flow therapy apparatus 10 may be humidified, and delivered to the patient via the patient conduit 16 through the cannula 17. The patient conduit 16 can have a heater wire 16a to heat gases flow passing through to the patient. The heater wire 16a can be under the control of the controller 13. The patient conduit 16 and/or patient interface 17 can be considered part of the flow therapy apparatus 10, or alternatively peripheral to it. The flow therapy apparatus 10, breathing conduit 16, and patient interface 17 together can form a flow therapy system.

The controller 13 can control the flow generator 11 to generate a gases flow of the desired flow rate. The controller 13 can also control a supplemental oxygen inlet to allow for delivery of supplemental oxygen, the humidifier 12 (if present) can humidify the gases flow and/or heat the gases flow to an appropriate level, and/or the like. The gases flow is directed out through the patient conduit 16 and cannula 17 to the patient. The controller 13 can also control a heating element in the humidifier 12 and/or the heating element 16a in the patient conduit 16 to heat the gas to a desired temperature for a desired level of therapy and/or level of comfort for the patient. The controller 13 can be programmed with or can determine a suitable target temperature of the gases flow. In some embodiments, gas mixture compositions including supplemental oxygen and/or administration of therapeutic medicaments may be provided through the supplemental oxygen inlet. The gas mixtures compositions may comprise oxygen, heliox, nitrogen, nitric oxide, carbon dioxide, argon, helium, methane, sulfur hexafluoride, and combinations thereof, and/or the supplemental gas can comprise an aerosolized medicament.

The oxygen inlet port 28 can include a valve through which a pressurized gas may enter the flow generator or blower. The valve can control a flow of oxygen into the flow generator blower. The valve can be any type of valve, including a proportional valve or a binary valve. The source of oxygen can be an oxygen tank or a hospital oxygen supply. Medical grade oxygen is typically between 95% and 100% purity. Oxygen sources of lower purity can also be used. Examples of valve modules and filters are disclosed in U.S. Provisional Application No. 62/409,543, titled "Valve Modules and Filter", filed on Oct. 18, 2016, and U.S. Provisional Application No. 62/488,841, titled "Valve Modules and Filter", filed on Apr. 23, 2017, which are hereby incorporated by reference in their entireties. Valve modules and filters are discussed in further detail below with relation to FIGS. 17-25.

The flow therapy apparatus 10 can measure and control the oxygen content of the gas being delivered to the patient, and therefore the oxygen content of the gas inspired by the patient. During high flow therapy, the high flow rate of gas delivered meets or exceeds the peak inspiratory demand of the patient. This means that the volume of gas delivered by the device to the patient during inspiration meets, or is in excess of, the volume of gas inspired by the patient during inspiration. High flow therapy therefore helps to prevent entrainment of ambient air when the patient breathes in, as well as flushing the patient's airways of expired gas. So long as the flow rate of delivered gas meets or exceeds peak inspiratory demand of the patient, entrainment of ambient air is prevented, and the gas delivered by the device is substantially the same as the gas the patient breathes in. As such, the oxygen concentration measured in the device, fraction of delivered oxygen, (FdO2) would be substantially the same as the oxygen concentration the user is breathing, fraction of inspired oxygen (FiO2), and as such the terms may can be seen as equivalent.

Operation sensors 3a, 3b, 3c, such as flow, temperature, humidity, and/or pressure sensors can be placed in various locations in the flow therapy apparatus 10. Additional sensors (for example, sensors 20, 25) may be placed in various locations on the patient conduit 16 and/or cannula 17 (for example, there may be a temperature sensor 29 at or near the end of the inspiratory tube). Output from the sensors can be received by the controller 13, to assist the controller in operating the flow therapy apparatus 10 in a manner that provides suitable therapy. In some configurations, providing suitable therapy includes meeting a patient's peak inspiratory demand. The apparatus 10 may have a transmitter and/or receiver 15 to enable the controller 13 to receive signals 8 from the sensors and/or to control the various components of the flow therapy apparatus 10, including but not limited to the flow generator 11, humidifier 12, and heater wire 16a, or accessories or peripherals associated with the flow therapy apparatus 10. Additionally, or alternatively, the transmitter and/or receiver 15 may deliver data to a remote server or enable remote control of the apparatus 10.

Oxygen may be measured by placing one or more gas composition sensors (such as an ultrasonic transducer system, also referred to as an ultrasonic sensor system) after the oxygen and ambient air have finished mixing. The measurement can be taken within the device, the delivery conduit, the patient interface, or at any other suitable location.

The flow therapy apparatus 10 can include a patient sensor 26, such as a pulse oximeter or a patient monitoring system, to measure one or more physiological parameters of the patient, such as a patient's blood oxygen saturation (SpO2), heart rate, respiratory rate, perfusion index, and provide a measure of signal quality. The sensor 26 can communicate with the controller 13 through a wired connection or by communication through a wireless transmitter on the sensor 26. The sensor 26 may be a disposable adhesive sensor designed to be connected to a patient's finger. The sensor 26 may be a non-disposable sensor. Sensors are available that are designed for different age groups and to be connected to different locations on the patient, which can be used with the flow therapy apparatus. The pulse oximeter would be attached to the user, typically at their finger, although other places such as an earlobe are also an option. The pulse oximeter would be connected to a processor in the device and would constantly provide signals indicative of the patient's blood oxygen saturation. The patient sensor 26 can be a hot swappable device, which can be attached or interchanged during operation of the flow therapy apparatus 10. For example, the patient sensor 26 may connect to the flow therapy apparatus 10 using a USB interface or using wireless communication protocols (such as, for example, near field communication, WiFi or Bluetooth®). When the patient sensor 26 is disconnected during operation, the flow therapy apparatus 10 may continue to operate in its previous state of operation for a defined time period. After the defined time period, the flow therapy apparatus 10 may trigger an alarm, transition from automatic mode to manual mode, and/or exit control mode (e.g., automatic mode or manual mode) entirely. The patient sensor 26 may be a bedside monitoring system or other patient monitoring system that communicates with the flow therapy apparatus 10 through a physical or wireless interface.

The flow therapy apparatus 10 may comprise a high flow therapy apparatus. High flow therapy as discussed herein is intended to be given its typical ordinary meaning as understood by a person of skill in the art, which generally refers to a respiratory assistance system delivering a targeted flow of humidified respiratory gases via an intentionally unsealed patient interface with flow rates generally intended to meet or exceed inspiratory flow of a patient. Typical patient interfaces include, but are not limited to, a nasal or tracheal patient interface. Typical flow rates for adults often range from, but are not limited to, about fifteen liters per minute (LPM) to about seventy liters per minute or greater. Typical flow rates for pediatric patients (such as neonates, infants and children) often range from, but are not limited to, about one liter per minute per kilogram of patient weight to about three liters per minute per kilogram of patient weight or greater. High flow therapy can also optionally include gas mixture compositions including supplemental oxygen and/or administration of therapeutic medicaments. High flow therapy is often referred to as nasal high flow (NHF), humidified high flow nasal cannula (HHFNC), high flow nasal oxygen (HFNO), high flow therapy (HFT), or tracheal high flow (THF), among other common names. The flow rates used to achieve "high flow" may be any of the flow rates listed below. For example, in some configurations, for an adult patient 'high flow therapy' may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between 25 LPM and 75 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may deliver gases to the patient at a flow rate of between about 1 LPM and about 100 LPM, or at a flow rate in any of the sub-ranges outlined above. The flow therapy apparatus 10 can deliver any concentration of oxygen (e.g., FdO2), up to 100%, at any flow rate between about 1 LPM and about 100 LPM. In some configurations, any of the flow rates can be in combination with oxygen concentrations (FdO2s) of about 20%-30%, 21%-30%, 21%-40%, 30%-40%, 40%-50%, 50%-60%, 60%-70%, 70%-80%, 80%-90%, and 90%-100%. In some combinations, the flow rate can be between about 25 LPM and 75 LPM in combination with an oxygen concentration (FdO2) of about 20%-30%, 21%-30%, 21%-40%, 30%-40%, 40%-50%, 50%-60%, 60%-70%, 70%-80%, 80%-90%, and 90%-100%. In some configurations, the flow therapy apparatus 10 may include safety thresholds when operating in manual mode that prevent a user from delivering to much oxygen to the patient.

High flow therapy may be administered to the nares of a user and/or orally, or via a tracheostomy interface. High flow therapy may deliver gases to a user at a flow rate at or exceeding the intended user's peak inspiratory flow requirements. The high flow therapy may generate a flushing effect in the nasopharynx such that the anatomical dead space of the upper airways is flushed by the high incoming gases flow. This can create a reservoir of fresh gas available for each and every breath, while minimizing re-breathing of nitrogen and carbon dioxide. Meeting inspiratory demand and flushing the airways is additionally important when trying to control the patient's FdO2. High flow therapy can be delivered with a non-sealing patient interface such as, for example, a nasal cannula. The nasal cannula may be configured to deliver breathing gases to the nares of a user at a flow rate exceeding the intended user's peak inspiratory flow requirements.

The term "non-sealing patient interface" as used herein can refer to an interface providing a pneumatic link between an airway of a patient and a gases flow source (such as from flow generator 11) that does not completely occlude the airway of the patient. Non-sealed pneumatic link can comprise an occlusion of less than about 95% of the airway of the patient. The non-sealed pneumatic link can comprise an occlusion of less than about 90% of the airway of the patient. The non-sealed pneumatic link can comprise an occlusion of between about 40% and about 80% of the airway of the patient. The airway can include one or more of a nare or mouth of the patient. For a nasal cannula the airway is through the nares.

The flow generator or blower 11 can include an ambient air inlet port 27 to entrain ambient room air into the blower. The flow therapy apparatus 10 may also include an oxygen inlet port 28 leading to a valve through which a pressurized gas may enter the flow generator or blower 11. The valve can control a flow of oxygen into the flow generator blower 11. The valve can be any type of valve, including a proportional valve or a binary valve.

The blower can operate at a motor speed of greater than about 1,000 RPM and less than about 30,000 RPM, greater than about 2,000 RPM and less than about 21,000 RPM, greater than about 4,000 RPM and less than about 19,000 RPM or between any of the foregoing values. Operation of the blower can mix the gases entering the blower through the inlet ports. Using the blower as the mixer can decrease the pressure drop that would otherwise occur in a system with a separate mixer, such as a static mixer comprising baffles, because mixing requires energy. Having a static mixer can also increase the volume of the gas flow path between the valve and the gases composition sensor, which can further increase the delay between when the valve current is changed and when a corresponding change in oxygen concentration is measured.

Based on user inputs and the therapy supplied by the specific device, the controller can determine a target output parameter for the blower. The controller can receive measurements of the target output parameter, and based on the difference between determined flow rate and the measured flow rate, the controller can adjust the speed of the blower.

The target output parameter may be flow rate. The target flow rate may be a constant value, (e.g., nasal high flow). The target flow rate may be a value that fluctuates. In some configurations, the controller can control a blower motor speed based on a target flow rate, and additionally increase or decrease the motor speed based on a patient's breathing cycle. The target flow rate does not necessarily change, but, the controller causes the motor speed to fluctuate in order add oscillations to the instantaneous flow rate such that the flow rate is synchronized with the patient's breathing. Such a system is described in International Application No. PCT/NZ2017/050063, titled "Flow Path Sensing for Flow Therapy Apparatus", filed on May 17, 2017.

The target output parameter may alternatively be pressure. The target pressure may be a constant value, (e.g., CPAP). Alternatively, the target flow rate may a value that fluctuates, potentially in time with the breath, (e.g., bi-level NW). In both of these scenarios, the total flow rate is unlikely to be constant.

Figure 1B:
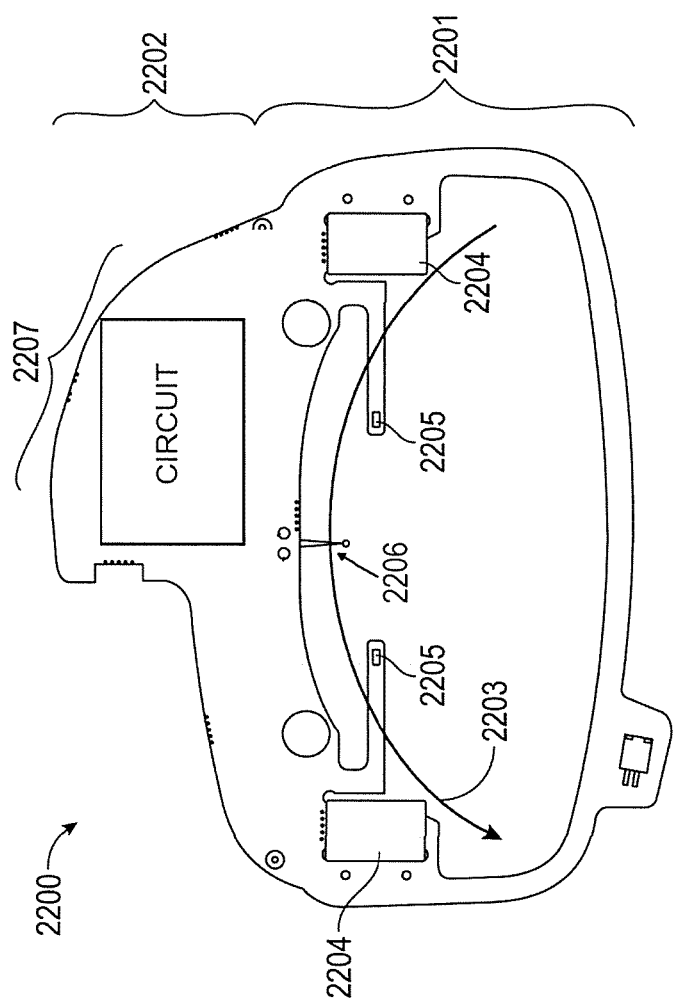
FIG. 1B illustrates a sensing circuit board including a flow rate sensor that may be used in a flow therapy apparatus.

With additional reference to FIG. 1B, a sensing circuit board 2200 is shown that can be implemented in the flow therapy apparatus 10. The sensing circuit board 2200 can be positioned in a sensor chamber such that the sensing circuit board 2200 is at least partially immersed in the flow of gases. The flow of gases may exit the blower 11 through a conduit and enter a flow path in the sensor chamber. At least some of the sensors on the sensing circuit board 2200 can be positioned within the flow of gases to measure gas properties within the flow. After passing through the flow path in the sensor chamber, the gases can exit to the humidifier 12 described above.

The sensing circuit board 2200 can be a printed sensing circuit board (PCB). Alternatively, the circuit on the board

2200 can be built with electrical wires connecting the electronic components instead of being printed on a circuit board. At least a portion of the sensing circuit board 2200 can be mounted outside of a flow of gases. The flow of gases can be generated by the flow generator 11 described above. The sensing circuit board 2200 can comprise ultrasonic transducers 2204. The sensing circuit board 2200 can comprise one or more of thermistors 2205. The thermistors 2205 can be configured to measure a temperature of the gases flow. The sensing circuit board 2200 can comprise a thermistor flow rate sensor 2206. The sensing circuit board 2200 can comprise other types of sensors, such as humidity sensors including humidity only sensors to be used with a separate temperature sensor and combined humidity and temperature sensors, sensors for measuring barometric pressure, sensors for measuring differential pressure, and/or sensors for measuring gauge pressure. The thermistor flow rate sensor 2206 can comprise hot wire anemometer, such as a platinum wire, and/or a thermistor, such as a negative temperature coefficient (NTC) or positive temperature coefficient (PTC) thermistor. Other non-limiting examples of the heated temperature sensing element include glass or epoxy-encapsulated or non-encapsulated thermistors. The thermistor flow rate sensor 2206 can be configured to measure flow rate of the gases by being supplied with a constant power, or be maintained at a constant sensor temperature or a constant temperature difference between the sensor and the flow of gases.

The sensing circuit board 2200 can comprise a first portion 2201 and a second portion 2202. The first portion 2201 can be positioned to be within the flow path of the gases, whereas the second portion 2202 can be positioned to be outside the flow path of the gases. The direction of the flow of gases is indicated in FIG. 1B by the arrow 2203. The direction of the flow of gases can be a straight line, or curved in shown in FIG. 1B.

Positioning the one or more of thermistors 2205 and/or the thermistor flow rate sensor 2206 downstream of the combined blower and mixer can take into account heat supplied to the gases flow from the blower. Also, immersing the temperature-based flow rate sensors in the flow path can increase the accuracy of measurements because the sensors being immersed in the flow can more likely to be subject to the same conditions, such as temperature, as the gases flow and therefore provide a better representation of the gases characteristics.

The sensing circuit board 2200 can comprise ultrasonic transducers, transceivers, or sensors of the sensing circuit board to measure gases properties of the gases flow, such as gas composition or concentration of one or more gases within the gases stream. Any suitable transducer, transceiver, or sensor may be mounted to the sensing circuit board 2200 as will be appreciated. In this configuration, the sensing circuit board includes an ultrasonic transducer system (also referred to as an ultrasonic sensor system) that employs ultrasonic or acoustic waves for determining gas concentrations. Various sensor configurations are described below with respect to FIGS. 1C-1F.

The ultrasonic transducer system may determine the relative gas concentrations of two or more gases in the gases flow. The ultrasonic transducer system may be configured to measure the oxygen fraction in the bulk gases stream flow, which consists of atmospheric air augmented with supplemental oxygen, which is essentially a binary gas mixture of nitrogen (N2) and oxygen (O2). It will also be appreciated that the ultrasonic transducer system may be configured to measure the gas concentrations of other augmentation gases that have blended with atmospheric air in the gases stream, including nitrogen (N2) and carbon dioxide (CO2). The ultrasonic transducers can determine the gas concentration of gases in the gases flow at a relatively high frequency. For example, the ultrasonic transducers can output a measured FdO2 value at a maximum sample rate of the sensors or at a lower frequency than the maximum sample rate, such as between about 1 Hz and 200 Hz, about 1 Hz and 100 Hz, about 1 Hz and 50 Hz, and about 1 Hz and 25 Hz.

In some configurations, sensing circuit board 2200 includes a pair of ultrasonic transducers that are provided on opposite sides of the sensing circuit board. Various alternative configurations of the ultrasonic transducers can be used for sensing the characteristics of the gases stream by the transmission and reception of ultrasonic beams or pulses.

The distance between the ultrasonic transducers 2204 on opposite ends of the sensing circuit board 2200 can affect measurement resolution. An increased distance between each of the ultrasonic transducers 2204 can reduce the proportional or fractional error, since in general a measured length will have a certain amount of error, and if the length is increased, the proportion of error generated during measurement is less than for a shorter length. Thus, the overall uncertainty of the measurement decreases. An increased distance can also increase measurement resolution and accuracy, since it allows for a longer time period for acoustic signals between the ultrasonic transducers 2204. However, an increased distance can lead to a weaker signal.

The ultrasonic transducers 2204 can be positioned such that the space between the ultrasonic transducers 2204 at least partially coincides with the flow path. In some configurations, the ultrasonic transducers are positioned on opposing ends of the sensing circuit board. Because the whole face of the flow path is exposed to the acoustic path, the sound waves propagate through all of the gases in the flow path. Averaging of the waves can occur across the entire flow path rather than a section of the flow path. Averaging over a longer distance reduces error and reduces the dependence of air-oxygen mixing. The ultrasonic transducers can be configured to measure the gases characteristics from any angle relative to the flow path.

Positioning sensors in the flow path or module, instead of outside the flow path or module, allows the transducers 2204 to both operate within a smaller temperature range relative to one another, or both substantially at one temperature (namely, the temperature of the gas flow). Having them at a substantially homogenous temperature increases accuracy as the transducers are sensitive to temperature. Further, positioning sensors along the flow path allows for measurements and calculations that account for the influence of the gas velocity so that the effect of gas velocity can be removed from the sensor measurement.

The ultrasonic transducer system is configured as an ultrasound binary gas sensing system. Binary gas analysis using ultrasound is based on sensing the speed of an acoustic pulse through the gas sample, which in this case is the bulk or primary flow of the gases stream flowing through sensing passage of the sensor housing. The speed of sound is a function of gas mean molecular weight and temperature. The system can receive a sensor signal indicative of the temperature of the gases flowing between the beam path between ultrasonic transducers. With knowledge of sensed speed of sound and sensed temperature, the gas composition in the gases stream may be determined or calculated. In particular, measurements of the speed of sound across the sensing passage may be used to infer the ratios of two known gases by reference to empirical relationships, standard algorithms, or data stored in the form of look-up tables, as is known in the art of binary gas analysis with ultrasound. It will be appreciated that alternatively an estimate of the temperature of the gases stream in the beam path of the ultrasound transducers may be used in the binary gas analysis calculations if a temperature sensor is not employed. In such alternative embodiments, the temperature of the gases stream may be conditioned or controlled to within a narrow temperature band to enable an estimate of temperature of the gases stream in the beam path to be used.

In some configurations, the flow therapy apparatus may also be provided with a humidity sensor that is located in the flow path and which is configured to generate a humidity signal indicative of the humidity of the gases stream flowing through the sensor assembly. In such embodiments, the gas composition may be determined by the sensed speed of sound, and the sensed temperature and/or sensed humidity. The humidity sensor may be a relative humidity sensor or an absolute humidity sensor. In some embodiments, the gas composition may be determined based on the sensed speed of sound and the sensed humidity, without the need for a temperature sensor.

The ultrasonic transducer system may be used to measure respective ratios of any two known gases in a gas composition. The ultrasonic transducer system can determine the relative gas concentration in a mixture of air blended with supplementary oxygen, which is substantially equivalent to a nitrogen/oxygen mixture. In such a binary gas mixture, by monitoring the speed of sound and taking the temperature into account, the mean molecular weight of the gas can be determined, and thus, the relative concentrations of the two gases may be determined. From this ratio, the oxygen fraction or nitrogen fraction of the gases stream may be extracted.

Referring to FIGS. 1C-1F, various configurations of the ultrasonic transducers will be described for the gas composition sensing system for sensing the speed of sound through the gases stream by the transmission and reception of ultrasonic beams or pulses. Like reference numerals, represent like components.

Figure 1E:
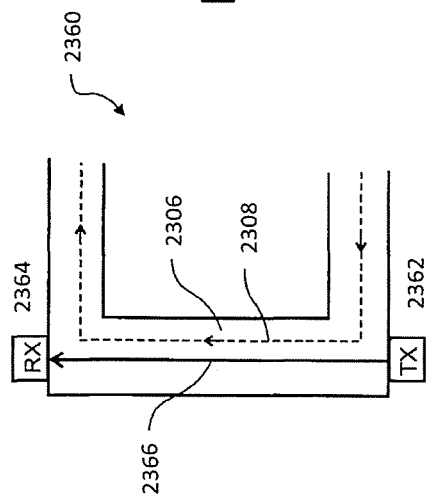
FIGS. 1E-1F illustrate schematic diagrams of various ultrasonic transducer configurations for the sensor system using along-flow beams.
Figure 1F:
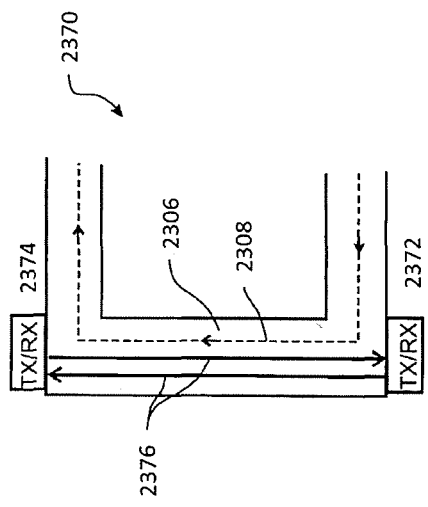
Figure 1C:
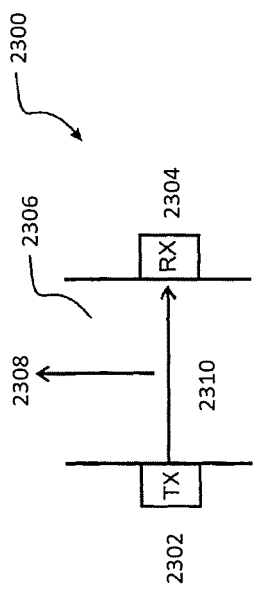
FIGS. 1C-1D illustrate schematic diagrams of various ultrasonic transducer configurations for the sensor system using cross-flow beams.

Referring to FIG. 1C, the transducer configuration 2300 provides an arrangement in which there is a pair of transducers 2302, 2304 opposing each other and positioned on opposite sides of the sensing passage 2306, with the gases flow path direction indicated generally by 2308. In this configuration, each of the transducers 2302, 2304 is driven as either a dedicated transmitter or receiver, such that ultrasonic pulses 2310 are transmitted uni-directionally across the gases flow path from the transmitter to the receiver transducer. As shown, the transducer pair is aligned (i.e. not-displaced upstream or downstream from each other) relative to the air flow path direction 2308 and is configured to transmit cross-flow pulses that are substantially perpendicular to the gases flow path direction.

Figure 1D:
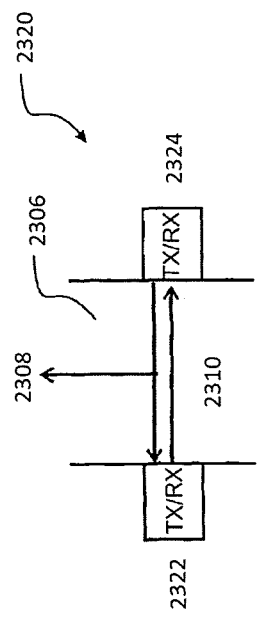

Referring to FIG. 1D, an alternative transducer configuration 2320 is illustrated in which a pair of transducers 2322, 2324 is provided opposing each other on opposite sides of the sensing passage, but wherein each transducer may operate as both a transmitter and receiver (i.e., the transducer is an ultrasonic transmitter-receiver or transceiver). In this configuration, bi-directional ultrasonic pulses 2326 may be sent between the transducer pair 2322, 2324. For example, pulses may be sent back and forth alternately between the transducers or in any other sequence or pattern. Again, the transducer pair is aligned relative to the gases flow path direction and are configured to transmit cross-flow pulses that are substantially perpendicular to the gases flow path direction.

Referring to FIG. 1E, an alternative transducer configuration 2360 is illustrated in which there is a pair of transducers 2362, 2364 opposing each other from opposite ends of the sensing passage 2306, with the gases flow path direction or axis indicated generally by 2308. In this configuration 2360, each of the transducers 2362, 2364 is driven as either a dedicated transmitter or receiver, such that along-flow ultrasonic pulses 2366 are transmitted uni-directionally in a beam path between the transmitter and receiver that is substantially aligned or parallel with the gases flow path axis 2308 in the sensing passage 2306. In the embodiment shown, the transmitter is upstream of the receiver, but it will be appreciated that the opposite arrangement could be employed. With this configuration, a flow rate sensor is provided in the sensing passage to provide a flow rate signal indicative of the flow rate of the gases stream in the sensing passage. It will be appreciated that the speed of sound in the sensing passage can be derived or determined in a similar manner to that previously described, and that the flow rate signal is utilized in the signal processing to remove or compensate for the gases flow rate in the calculated speed of sound signal.

Referring to FIG. 1F, an alternative transducer configuration 2370 is illustrated in which a pair of transducers 2372, 2374 is provided opposing each other from opposite ends of the sensing passage like in FIG. 1E, but wherein each transducer may operate as both a transmitter and receiver, i.e. is an ultrasonic transmitter-receiver or transceiver. In this configuration, bi-directional along-flow ultrasonic pulses 2376 may be sent between the transducer pair 2372, 2374. For example, pulses may be sent back and forth alternately between the transducers or in any other sequence or pattern. Again, the transducer pair are aligned with the gases flow path axis 2308 and are configured to transmit along-flow pulses in a beam path or paths that are substantially aligned or parallel to the gases flow path axis 2308 in the sensing passage 2306. With this configuration, a separate flow rate sensor need not necessarily be provided, as the flow rate component of the speed of sound signal can be directly derived or determined from processing of the transmitted and received acoustic pulses.

In some configurations, the flow therapy apparatus can measure the total flow rate of gases using a flow bead, as is described in International Application No. PCT/NZ2017/050119, titled "Thermistor Flow Sensor Having Multiple Temperature Points", filed on Sep. 13, 2017. The flow bead can have the advantage of providing a more accurate measure of the flow rate, however it can be slow to react to sudden changes in the flow (such as high frequency oscillations). The ultrasonic transducers can measure sudden changes in the flow, however the overall measurement can be less accurate. In some configurations, the controller can generate a final measurement of the total flow rate by combining inputs from a flow bead and ultrasonic transducers, thereby allowing for a measure of the flow rate that is both accurate and able to detect sudden changes in the flow.

Some examples of flow therapy apparatuses are disclosed in International Application No. PCT/NZ2016/050193, titled "Flow Path Sensing for Flow Therapy Apparatus", filed on Dec. 2, 2016, and International Application No. PCT/M2016/053761, titled "Breathing Assistance Apparatus", filed on Jun. 24, 2016, which are hereby incorporated by reference in their entireties. Examples of configurations of flow therapy apparatuses that can be used with aspects of the present disclosure are discussed in further detail below.

Closed Loop Control

With reference again to FIG. 1A, the controller 13 can be programmed with or configured to execute a closed loop control system for controlling the operation of the flow therapy apparatus. The closed loop control system can be configured to ensure the patient's SpO2 reaches a target level and consistently remains at or near this level.

The controller 13 can receive input(s) from a user that can be used by the controller 13 to execute the closed loop control system. The target SpO2 value can be a single value or a range of values. The value(s) could be pre-set, chosen by a clinician, or determined based on the type of patient, where type of patient could refer to current affliction, and/or information about the patient such as age, weight, height, gender, and other patient characteristics. Similarly, the target SpO2 could be two values, each selected in any way described above. The two values would represent a range of acceptable values for the patient's SpO2. The controller can target a value within said range. The targeted value could be the middle value of the range, or any other value within the range, which could be pre-set or selected by a user. Alternatively, the range could be automatically set based on the targeted value of SpO2. The controller can be configured to have one or more set responses when the patient's SpO2 value moves outside of the range. The responses may include alarming, changing to manual control of FdO2, changing the FdO2 to a specific value, and/or other responses. The controller can have one or more ranges, where one or more different responses occur as it moves outside of each range.

Generally, SpO2 would be controlled between about 80% and about 100%, or about 80% and about 90%, or about 88% and about 92%, or about 90% and about 99%, or about 92% and about 96%. The SpO2 could be controlled between any two suitable values from any two of the aforementioned ranges. The target SpO2 could be between about 80% and about 100%, or between about 80% and about 90%, or between about 88% and about 92%, or between about 90% and about 99%, or between about 92% and about 96%, or about 94%, or 94% or about 90%, or 90%, or about 85%, or 85%. The SpO2 target could be any value between any two suitable values from any two of the aforementioned ranges. The SpO2 target can correspond to the middle of the SpO2 for a defined range.

The FdO2 can be configured to be controlled within a range. As discussed previously, the oxygen concentration measured in the apparatus (FdO2) would be substantially the same as the oxygen concentration the patient is breathing (FiO2) so long as the flow rate meets or exceeds the peak inspiratory demand of the patient, and as such the terms may can be seen as equivalent. Each of the limits of the range could be pre-set, selected by a user, or determined based on the type of patient, where the type of patient could refer to current affliction, and/or information about the patient such as age, weight, height, gender, and/or other patient characteristic. Alternatively, a single value for FdO2 could be selected, and the range could be determined at least partially based on this value. For example, the range could be a set amount above and below the selected FdO2. The selected FdO2 could be used as the starting point for the controller. The system could have one or more responses if the controller tries to move the FdO2 outside of the range. These responses could include alarming, preventing the FdO2 moving outside of the range, switching to manual control of FdO2, and/or switching to a specific FdO2. The device could have one or more ranges where one or more different responses occur as it reaches the limit of each range.

Figure 2:
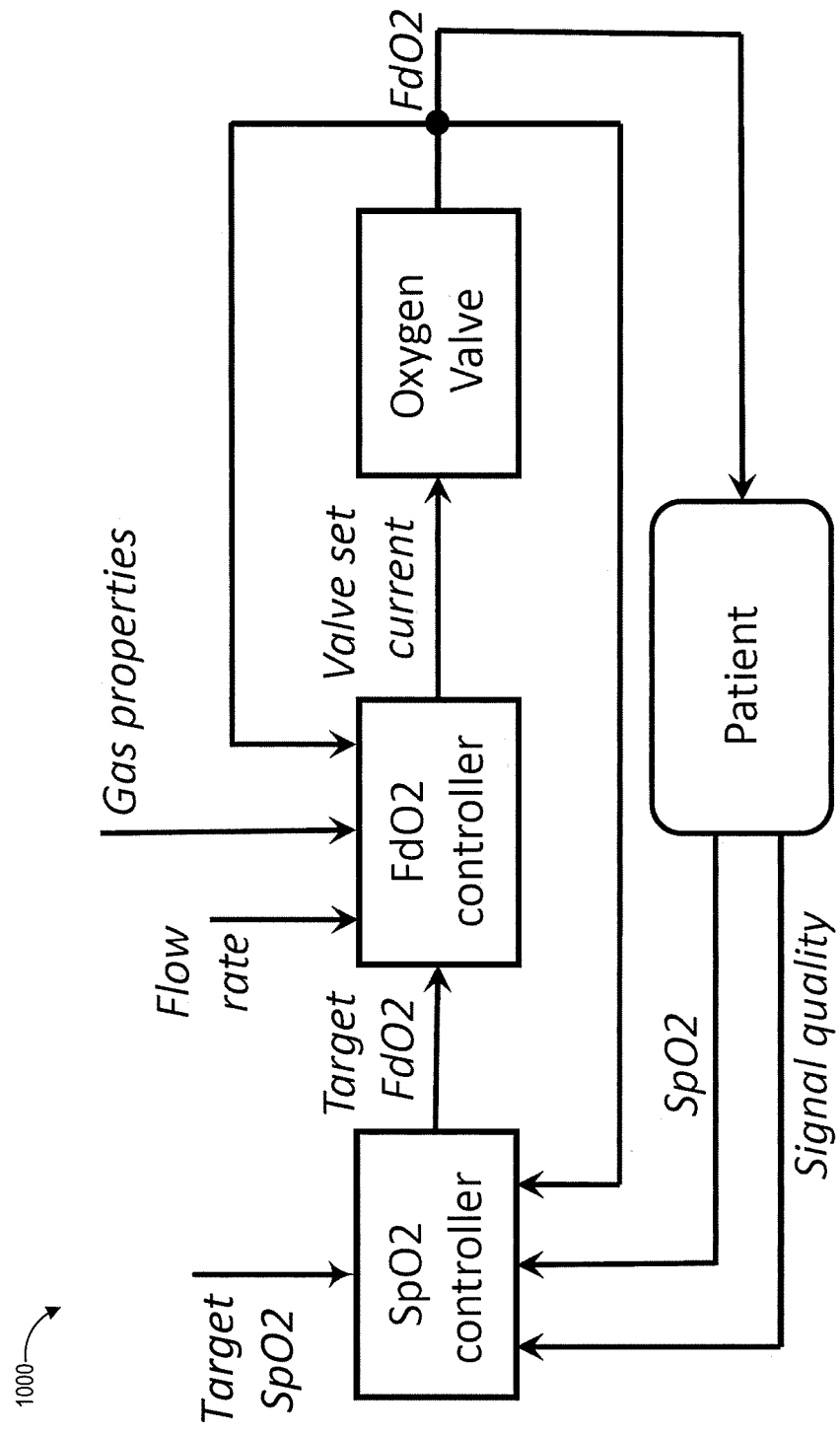
FIG. 2 is a schematic diagram of a closed loop control system.

With reference to FIG. 2 a schematic diagram of the closed loop control system 1000 is illustrated. The closed loop control system may utilize two control loops. The first control loop may be implemented by the SpO2 controller. The SpO2 controller can determine a target FdO2 based in part on the target SpO2 and/or the measured SpO2. As discussed above, the target SpO2 value can be a single value or a range of acceptable values. The value(s) could be pre-set, chosen by a clinician, or determined automatically based on client characteristics. Generally, target SpO2 values are received or determined before or at the beginning of a therapy session, though target SpO2 values may be received at any time during the therapy session. During a therapy session, the SpO2 controller can also receive as inputs: measured FdO2 reading(s) from a gases composition sensor, and measured SpO2 reading(s) and a signal quality reading(s) from the patient sensor. In some configurations, the SpO2 controller can receive target FdO2 as an input, in such a case, the output of the SpO2 controller may be provided directly back to the SpO2 controller as the input. Based at least in part on the inputs, the SpO2 controller can output a target FdO2 to the second control loop.

During the therapy session, the SpO2 and FdO2 controllers can continue to automatically control the operation of the flow therapy apparatus until the therapy session ends or an event triggers a change from the automatic mode to manual mode.

FdO2 Control System

With reference again to FIG. 1A, the controller 13 can be programmed with or configured to execute an FdO2 control system for controlling the operation of the flow therapy apparatus.

The FdO2 control system can be configured to ensure that the instantaneous FdO2 is maintained at a target level at all points during a therapy session. The controller can measure the FdO2, compare it with the target FdO2, and then adjust the oxygen inlet valve accordingly. However, when the FdO2 sensors are located at a non-insignificant distance away from the valve, there is a time delay between when a change is made to the valve and when a corresponding change in the FdO2 is measured. The controller may adjust the valve after the time delay. However, if the flow rate is fluctuating, then the controller may be able to achieve the target FdO2 on average, but not at a continuous and substantially instantaneous basis. In order to maintain the FdO2 at the target level at a continuous and substantially instantaneous basis, without moving the FdO2 sensors closer to the valve, the FdO2 controller can factor in the measurement of a total flow rate into the control of the valve.

Process for Adjusting Valve Flow Rate

Figure 18:
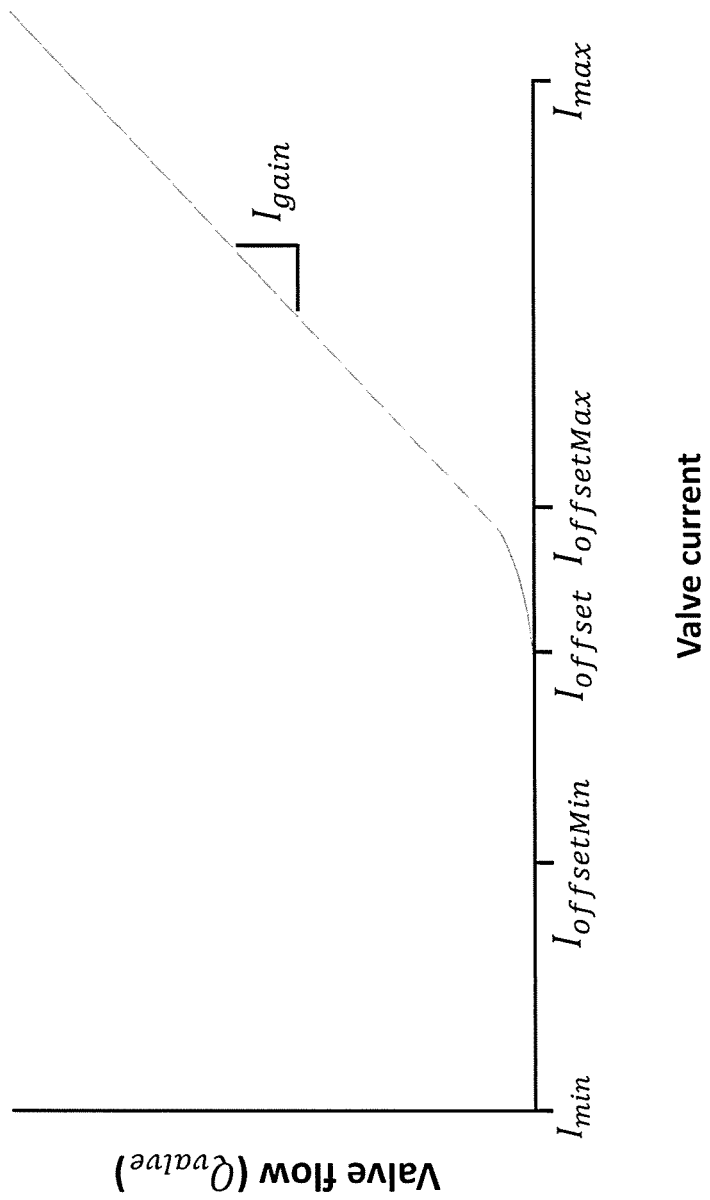
FIG. 18 is an example of a graph that illustrates relationships between valve parameters.
Figure 19:
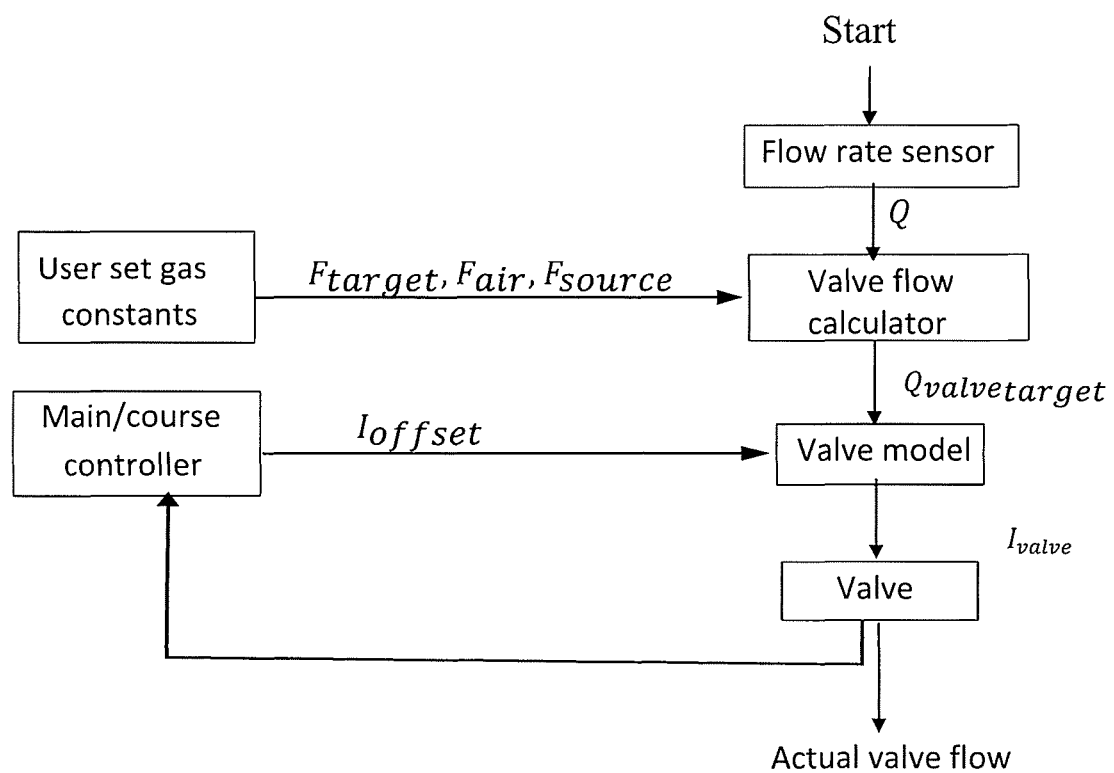
FIG. 19 illustrates an example of a flow chart for a process of adjusting a valve.
Figure 20:
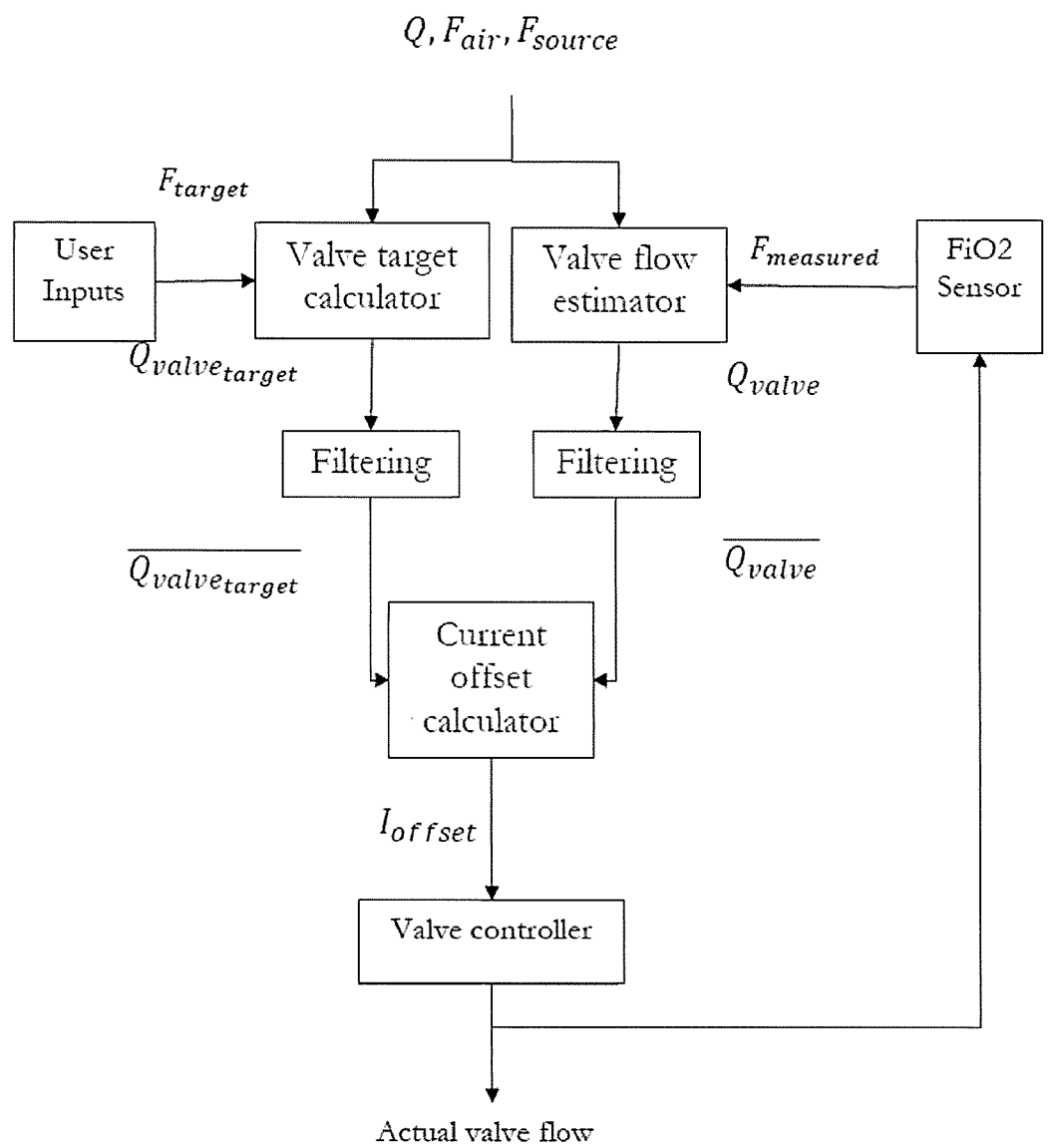
FIG. 20 illustrates an example of a flow chart for a process of updating a valve model.

With additional reference to FIGS. 18 and 19, the process for adjusting the flow rate of the oxygen inlet valve is illustrated. The main controller can first determine a valve flow rate that would be required to achieve the target FdO2. This can be based on the target oxygen concentration, the oxygen concentration of the oxygen source, the oxygen concentration of the ambient air, and the current flow rate.

Target oxygen concentration ($F_{target}$) can be set by the user or by the closed loop SpO2 control algorithm described herein. Oxygen concentration of the ambient air ($F_{air}$) can be assumed to be constant. Generally, oxygen concentration of the oxygen source ($F_{source}$) is a constant parameter. In some cases, the oxygen concentration may be able to be adjusted to by the user. The current flow rate (Q) can be measured by one or more flow rate sensors.

$$Q_{valve_{target}} = Q\left(\frac{F_{target} - F_{air}}{F_{source} - F_{air}}\right)$$

In one configuration, the equation above for the target valve flow rate ($Q_{valve_{target}}$) can be constantly updated as the target FdO2 and the flow rate change.

Once the target valve flow rate is determined, the controller can determine the required valve current to actuate the valve to achieve the target valve flow rate, which can be determined by a valve model.

The valve model may use two or more parameters to determine the valve current. The first parameter can be valve gain ($I_{gain}$), which defines the linear component of the relationship between a change in current and a change in flow rate. In some configuration, the value for the valve gain can be a pre-set constant. Alternatively, the valve gain can be determined based on the pressure of the oxygen source. The pressure of the oxygen source can refer to the pressure upstream of the flow control valve, which has likely been set by a pressure regulator on the oxygen supply. The pressure of the oxygen source may be measured by a pressure sensor upstream of the oxygen valve.

The second parameter can be the current offset required to open the valve ($I_{offset}$), below which there will be no flow through the valve. The current offset can vary within a range having a minimum ($I_{offsetMin}$) and a maximum ($I_{offsetMax}$). The current offset value can be first estimated by a coarse controller, and then adjusted over time using a main controller. In some embodiments, a single controller can estimate and adjust the value.

$$I_{valve} = I_{offset} + \frac{Q_{valve_{target}}}{I_{gain}} + \frac{Q_{valve_{target}}}{30 + 100 Q_{valve_{target}}}$$

The controller can then set the valve current ($I_{valve}$) at the determined value. This process of determining the target valve flow rate and then updating the valve current can be run continuously. For example, the process can be ran at a rate of 20 Hz.

Coarse Controller

When the valve is first activated (e.g., target FdO2 raised from 21%), the coarse controller can first determine the current offset required to open the valve. As described previously, due to the distance between the valve and the gases composition sensor, there is a time delay between when the position of the valve is adjusted and when a corresponding change in FdO2 is measured. As such, there is a risk that increasing the current too quickly when determining the current offset could cause the controller to overshoot the target FdO2. On the other hand, increasing the current too slowly could cause there to be more delay before the device can begin supplying the target FdO2 levels to the patient.

Initially, the estimated current offset may be set to a minimum expected value ($I_{offset_{min}}$) (see, for example, FIG. 18). The current for the valve can then be set based on the target valve flow rate using the valve model. The estimate for the current offset can be continually updated by the main controller. However, as described above, the main controller may be too slow to find the current offset when the valve is closed, resulting in an extended time period in which no supplemental oxygen is supplied.

The coarse controller can iteratively increase the estimation of the current offset until a flow of gas through the valve is detected. The magnitude of the increase at each iteration may be calculated in at least two ways. In some configurations, the larger of the two magnitudes calculated can then be implemented.

The current offset can be adjusted at each time step by increasing the current offset by an exponentially increasing amount ($\Delta I_{exp}$). Alternatively, the current offset can be adjusted at each time step by increasing the current offset by a minimum amount ($\Delta I_{min}$). This minimum amount can be proportional to the determined target valve flow rate. A higher target valve flow rate can mean that larger changes in the current offset estimation can be made without risking overshooting the target FdO2.

At each iteration of the coarse controller, the coarse controller can increase the current offset estimation by the larger of the two values described above. In some configurations, the controller could begin by increasing the valve by $\Delta I_{min}$, and then switch to using $\Delta I_{exp}$ once $\Delta I_{exp} > \Delta I_{min}$.

$$\Delta I_{exp} = \Delta I_{exp}^{previous}(1 + \Delta t \Delta I_{increase})$$

$$\Delta I_{min} = \frac{Q_{valve_{target}}}{I_{gain}}$$

$$I_{offset} = I_{offset}^{previous} + \max(\Delta I_{exp}, \Delta I_{min})$$

Wherein $\Delta t$ is the time step of the controller, and $\Delta I_{increase}$ is the fractional increase in $\Delta I_{exp}$.

The coarse controller can be activated when the target FdO2 is first changed or any time the target FdO2 is changed from ambient to an increased value (e.g., $FiO2_{target}=21\% \rightarrow FiO2_{target}>21\%$). The coarse controller can also be activated when the user enters closed loop SpO2 control. The estimation of current offset value ($I_{offset}$) determined during a therapy session can be stored by the coarse controller, such that the current offset is not reset to the minimum current offset after each activation.

The flow therapy apparatus can switch from using the coarse controller to using the main controller once a flow of gas from the valve is detected. The flow of gas from the valve can be determined by measuring the FdO2 using the gases composition sensor. The valve can be determined to be opened once the measured FdO2 exceeds ambient levels by a threshold amount. The threshold amount may be based on a sensor error (e.g., for a gases composition sensor with up to 3% error in the measured FdO2 value, the valve is determined to be open when the FdO2 exceeds 24%).

Updating the Valve Model

In order to maintain the FdO2 at the target level, the process, described with relation to FIG. 19, relies on the accuracy of the valve model. In order to improve this accuracy, the main controller can continuously evaluate the accuracy of the model, and then adjust the current offset ($I_{offset}$) accordingly. The process for updating the valve model is described with respect to FIG. 20. This process can be done at a rate that is slower than the process for setting the valve current ($I_{valve}$). For example, in some configurations, the current offset can be adjusted at a rate of 3 Hz. The valve model can be updated at different rates depending on various settings or parameters, such as, for example, expected respiration rate ranges, expected amplitudes of flow rate oscillations, and/or other settings or parameters.

Exponential Filtering

To adjust the current offset, the controller can compare the average target valve flow rate with an estimate of the average actual valve flow rate (the average for both of these values being the average over a breath). In order to obtain these averages, several parameters can be filtered over time using an exponential filter with a time constant $T_{fill}$. $T_{fill}$ can be selected such that fluctuations in the measured flow rate within the course of a breath of a patient are filtered out. At each iteration of the main controller, the filtered values of the following parameters can be updated:

$$\overline{Q} \quad \overline{QF_{measured}} \quad \overline{QF_{target}} \quad \overline{\frac{dF_{measured}}{dt}}$$

The macron is used throughout the present specification to indicate parameters that are representative of an average value across a breath of a patient.

Average Target Valve Flow Rate

Following the update of filtered values above, the main controller can calculate the average target valve flow rate and the estimate of the average actual valve flow rate.

$$\overline{Q_{valve_{target}}} = \frac{\overline{QF_{target}} - \overline{QF_{air}}}{F_{source} - F_{air}}$$

The equation above for determining the average target valve flow rate is similar to the equation for determining the instantaneous valve flow rate, the only difference being certain values being replaced by filtered versions of the same parameter.

Average Valve Flow Rate

The average valve flow rate can be estimated using a model. The average value flow rate model can estimate the flow through the valve. The model can take into account the amount of time it takes for oxygen to mix with ambient air and reach the sensor. In some configurations, this model may be a physically derived differential equation such as a first order model, advection diffusion equation, or naiver stokes equation. This model could be obtained numerically using machine learning algorithms, such as neural networks. In one configuration, the average valve flow rate ($\overline{Q_{valve}}$) can be calculated by the following equations.

$$\overline{Q_{valve}} = \frac{\overline{QF_{control}} - \overline{QF_{air}}}{F_{source} - F_{air}}$$

$$\overline{QF_{control}} = V\left(\overline{\frac{dF_{measured}}{dt}}\right) + \overline{QF_{measured}}$$

Where $F_{measured}$ is the fraction of oxygen measured by the gases composition sensor, $F_{control}$ is the fraction of oxygen that the measured fraction of oxygen is tending towards and that will result from the current valve position and the current flow rate, and V is the effective volume between the valve outlet and the gases composition sensor. $F_{control}$ is used instead of $F_{measured}$ in the first equation due to the time delay between when the valve position is adjusted and when gases composition sensor detects a corresponding change in $F_{measured}$. When estimating the valve flow rate ($Q_{valve}$), $F_{control}$ can be used instead of $F_{measured}$ in order to account for the delay between a change in valve current and a corresponding change in $F_{measured}$. This can be calculated by using the derivative term in the second equation. As such, $F_{control}$ can function as a prediction of what $F_{measured}$ is going to be. As can be seen in the second equation, if the gases composition sensor was substantially close to the valve outlet, the V would be close to zero, and the $F_{control}$ would be substantially the same as $F_{measured}$.

The difference between $\overline{Q_{valve_{target}}}$ and $\overline{Q_{valve}}$ can then be input into the controller, which can then output a change to estimate of $I_{offset}$. If $\overline{Q_{valve_{target}}}$ and $\overline{Q_{valve}}$ are very similar, then it indicates that the estimate of $I_{offset}$ is close to being correct, and as such only a small change is made. Conversely, if $\overline{Q_{valve_{target}}}$ and $\overline{Q_{valve}}$ are substantially different then it indicates that the $I_{offset}$ further from the correct value, and as such a larger change is made.

The coefficients used by the controller can be inversely proportional to the time constant used for the exponential filter.

Accounting for Different Therapies

The FdO2 controller can vary the control of the flow therapy apparatus depending on which therapy is delivered by the specific device. In one configuration, time constants can be set for the exponential filtering based on the therapy, which in turn can set the coefficients of the controller described herein.

The time constant used for each therapy can be set based on typical fluctuations in flow for said therapy. Therapies with more consistent flow rates can have smaller time constants such that older data can be decayed away faster. This in turn can result in larger coefficients for the controller, such that the value of $I_{offset}$ is adjusted in larger increments. When the total flow is more consistent, then the current offset can be adjusted more quickly.

Conversely, therapies with less consistent flow rates can have smaller time constants such that such that older data is decayed away slower. This in turn can result in smaller coefficients for the PI controller, such that the value of $I_{offset}$ is adjusted in smaller increments. When the total flow is less consistent, then the current offset can be adjusted more slowly.

Additionally, the filter time constant (and in turn the coefficients) may be adjusted based on the set flow rate for certain therapies. In general, a larger flow rate would result in a smaller filter time constant, as the resulting flow rate would be more consistent, and the time delay between the valve and the gases composition sensor would be smaller.

Target Oxygen Alarms

In addition to controlling the valve to achieve the target FdO2, the main controller can also continuously assess whether or not the target FdO2 can be achieved. The main controller can set an accuracy threshold for the FdO2 algorithm. The accuracy threshold may increase with the target FdO2 value.

An alarm may be generated if the oxygen is determined to be too high. In some configurations, the alarm is generated if the following two criteria are met continuously for at least a defined period of time (e.g., 8 seconds or more): (i) the measured FdO2 exceeds the target FdO2 by an amount greater than the accuracy threshold; and (ii) the estimated current offset is at its minimum expected value. The period of time can be any defined period of time.

The determination of oxygen being too high and the corresponding alarm are then cleared if the measured FdO2 then falls below the threshold for a defined period of time (e.g., more than two seconds).

The oxygen is determined to be too low and an alarm is generated if the following two criteria are met continuously for a defined period of time (e.g., 5 seconds or more): (i) the measured FdO2 is less than the target FdO2 by an amount greater than the accuracy threshold; and (ii) the estimated current offset is at its maximum expected value.

The determination of oxygen being too low and the corresponding alarm are then cleared if the measured FdO2 then exceeds the threshold for a defined period of time (e.g., more than two seconds). The period of time for each threshold to turn on or off the corresponding alarm can be any defined period of time and can be different or the same as other thresholds.

Oxygen Filtering for Display

The controller can continuously determine a measure of effective FdO2. The effective FdO2 can be calculated by filtering a measure of the total quantity of oxygen delivered to the patient, and then dividing this value by a filtered measure of the total gas delivered to the patient.

$$F_{effective} = \frac{\overline{QF_{measured}}}{\overline{Q}}$$

The controller can then alternate between displaying the target FdO2 and the effective FdO2. If the effective FdO2 is close enough to the target FdO2, then it is preferable to simply display the target FdO2, as this target value is being satisfied within a defined threshold. Alternatively, if the effective FdO2 is significantly different than the target FdO2, then the effective FdO2 is displayed instead. In which case, the target FdO2 is not within the defined threshold and may not be considered an accurate representation of the FdO2 being delivered to the patient.

If the device is operating in low pressure mode (e.g., the device is set up to be supplied oxygen via the low pressure port), then the target FdO2 can be considered to be 21%.

The controller can determine whether the effective FdO2 is sufficiently close to the target FdO2 by taking the difference between the two values and comparing it with a threshold. When the device is displaying the effective FdO2, it would switch to displaying the target FdO2 if the difference falls below a first threshold. When the device is displaying target FdO2, it would switch to displaying effective FdO2 if the difference exceeds a second threshold. The second threshold may be greater than the first threshold. For example, the first threshold can be 0.5% and the second threshold can be 2.5%. The first threshold may be the same as the second threshold. For example the first threshold and the second threshold can be 2.5%.

Additionally, or alternatively, the first and/or second threshold may be determined at least in part based on an accuracy threshold used for the high/low oxygen alarms. Using the accuracy threshold can help to ensure that the flow therapy apparatus does not generate a high/low oxygen alarm while also displaying the target FdO2.

Oxygen Conservation Process

With reference again to FIG. 1A, the controller 13 can be programmed with or configured to execute an oxygen conservation process for controlling the operation of the flow therapy apparatus 10. The oxygen conservation process can work in conjunction with the closed loop control system and open loop control systems disclosed herein. The oxygen conservation process can be configured to conserve oxygen while ensuring the patient's SpO2 reaches a target level and consistently remains at or near this level.

The oxygen conservation process described herein reduces the total amount of oxygen used without reducing the effective FdO2 received by the patient during inspiration. The oxygen conservation process can adjust an oxygen flow control valve such that the FdO2 during at least a portion of the expiratory period is below the target FdO2.

The oxygen conservation process can adjust the oxygen flow control valve to deliver an increased amount of oxygen enriched gas above the FdO2 target at the end of expiration and/or at the start of inspiration, such that the FdO2 delivered to the patient is quickly returned to the FdO2 target level for the inspiratory period. The oxygen conservation process can adjust the oxygen flow control valve down to such that the FdO2 is brought back down the FdO2 target level.

An advantage of the oxygen conservation process is to reduce the amount of supplementary gases (e.g. oxygen) used by the flow therapy apparatus without significantly impacting the therapy provided to the patient. The oxygen conservation process can be beneficial in that it allows oxygen to be conserved during the expiratory period while still providing the desired therapy by achieving a target FdO2 during the inspiratory period. This is also beneficial because it reduces the amount of oxygen being dispersed into the ambient environment, and a reduction in the amount of oxygen used reduces cost for the user. This can also reduce the frequency at which the user needs to refill or replace the oxygen source, such as an oxygen canister.

Determination of Respiratory Period

A "respiratory period" as used herein can refer to one full breath cycle of a patient, which is made up of an inspiratory period and an expiratory period. The inspiratory period covering a full cycle of inspiration and the expiratory period covering a full cycle of expiration.

A "respiratory phase" as used herein can refer to a discrete time position in either the inspiratory period or the expiratory period.

In order to conserve oxygen without reducing the efficacy of the therapy, the oxygen conservation process can reduce the oxygen being delivered during expiration, while returning the FdO2 at the patient interface to the target FdO2 level by the start of each inspiratory period. To do this, the controller 13 can generate a model of the patient's respiratory cycle. The controller 13 can control and/or receive signals from components of the flow therapy apparatus 10. The controller 13 can be configured to analyse respiration cycles of the patient and determine the respiratory model of the patient. For example, the controller can generate a waveform representative of the patient's respiratory period. The controller 13 can also estimate the instantaneous fraction of oxygen of the gas exiting the patient interface.

Figure 21:
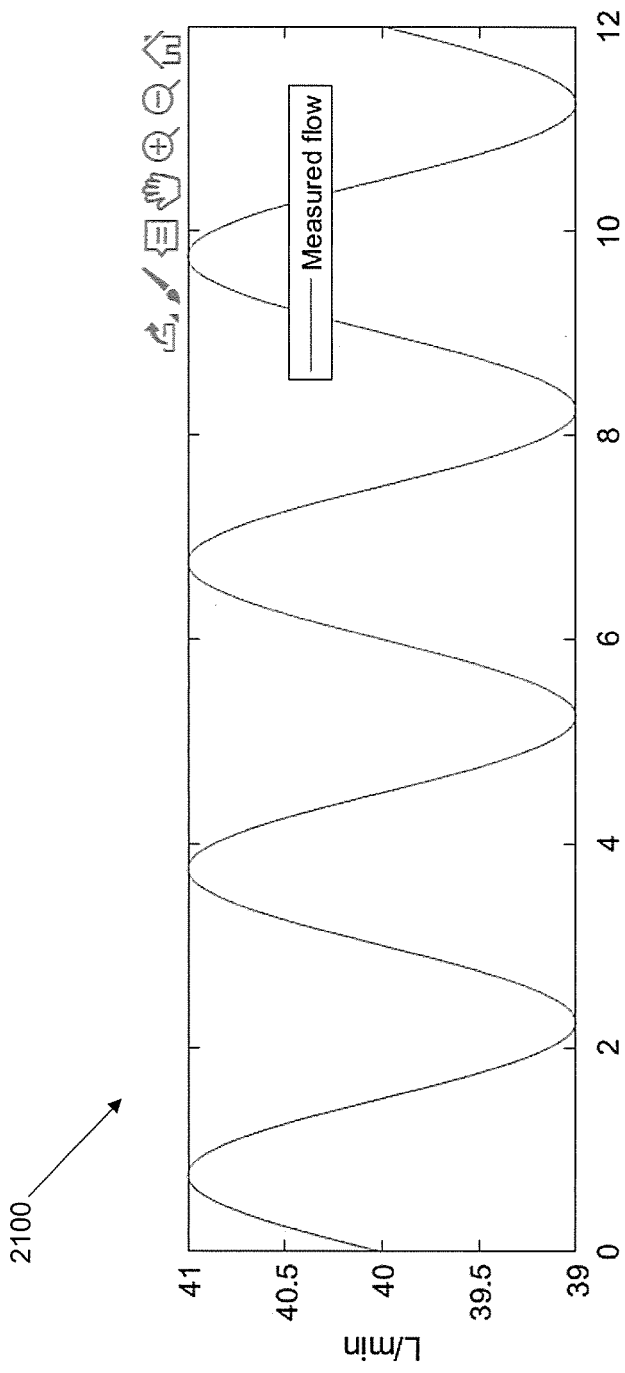
FIG. 21 illustrates an example of a chart of measured flow during respiration.

FIG. 21 illustrates a waveform 2100 of measured flow during respiration in a high flow system. In a high flow system, the flow rate of the gases can be maintained at a relatively constant level. However, due to the speed of the control algorithm for the blower, there can still be slight fluctuations in flow, specifically, an increased flow rate during inspiration and a decreased flow rate during expiration.

The controller 13 can determine the respiratory period and/or phase by analysing fluctuations in flow rate. The respiratory period and/or phase can be determined using a combination of measurements. For example, by analysing a combination of flow rate and motor speed, an estimate of the resistance of the circuit can be calculated. The resistance will fluctuate periodically with the patient's respiration. Example embodiments of systems and methods for analysing and determining a respiratory rate of the patient are further described in PCT/M2018/059195 and PCT/NZ2017/050063, which are incorporated by reference herein in their entirety.

The patient's respiratory period can be determined through frequency analysis (such as an FFT) or time domain analysis (such as zero crossings). The control of the FdO2 can be done based on a system of triggering, wherein the controller 13 can identify one or more indicators of a transition between inspiration and expiration (and vice versa) and use the indicators to initiate an adjustment in FdO2.

In some embodiments, the controller 13 can wait until the patient's respiratory cycle is determined to be consistent, and then begin executing an oxygen conservation mode based on a control cycle that corresponds to the patient's respiratory period. The controller can then adjust or halt the control cycle should the patient's respiratory period change.

The controller can be configured to execute the oxygen conservation mode of operation when the characterisation of the patient's respiratory cycle satisfies a certain confidence threshold, as the conservation of oxygen is dependent upon the accurateness of the characterisation of the patient's respiratory cycle. The confidence threshold is more likely to be satisfied when the patient is breathing consistently with a sufficiently high tidal volume. In situations where the patient's respiratory cycle cannot be confidently characterised, the controller 13 can execute the default therapy mode instead of the oxygen conservation mode where the controller is configured to meet the target FdO2 at substantially all points of the patient's respiratory cycle as further described herein.

Advection-Diffusion Calculations

When the oxygen conservation process is delivering a flow of gases with an FdO2 that is relatively consistent over time, the FdO2 can also be assumed to be consistent throughout the length of the breathing circuit. However, if the FdO2 is fluctuating over time, then the FdO2 at specific moments in time may be different at different locations in the breathing circuit. In particular, the measurement of FdO2 by the gases composition sensors in the device may not match the FdO2 at the patient interface. In order to ensure that the patient is being supplied with the correct FdO2, an estimate of the FdO2 at the patient interface can be calculated based on the FdO2 measured at the device over time.

There are two main factors that result in the difference between the FdO2 measured at the device and the FdO2 at the patient interface. The first factor is the time delay caused by the gas traveling between the two locations, resulting in the peaks and troughs in the FdO2 values at the patient interface, which can be offset in the time domain by the corresponding peaks and troughs in the FdO2 measurements at the device. The second factor is that a certain amount of mixing will occur as the gases travel through the circuit, resulting in a reduced amplitude in the waveform in the oxygen concentration at locations that are further downstream in the breathing circuit.

Both of these factors can be accounted for using an advection-diffusion equation. The advection-diffusion equation comprises an advection term to account for the aforementioned time delay, and a diffusion term to account for the aforementioned mixing. Equation (1) is an example embodiment of an advection-diffusion equation:

$$\frac{\partial F}{\partial t} = -Q\frac{\partial F}{\partial L} + 0.05\frac{\partial^2 F}{\partial L^2} \quad (1)$$

An advection-diffusion equation can be solved numerically, such as by using an upwind finite difference scheme with Crank-Nicholson time stepping. Alternatively, an advection-diffusion equation can be solved with a low accuracy numerical scheme for an advection equation, wherein the diffusion term is ignored and instead obtained as from the "numerical-diffusion" that arises from this scheme. This second method can be less accurate but can save on computational power.

Figure 22:
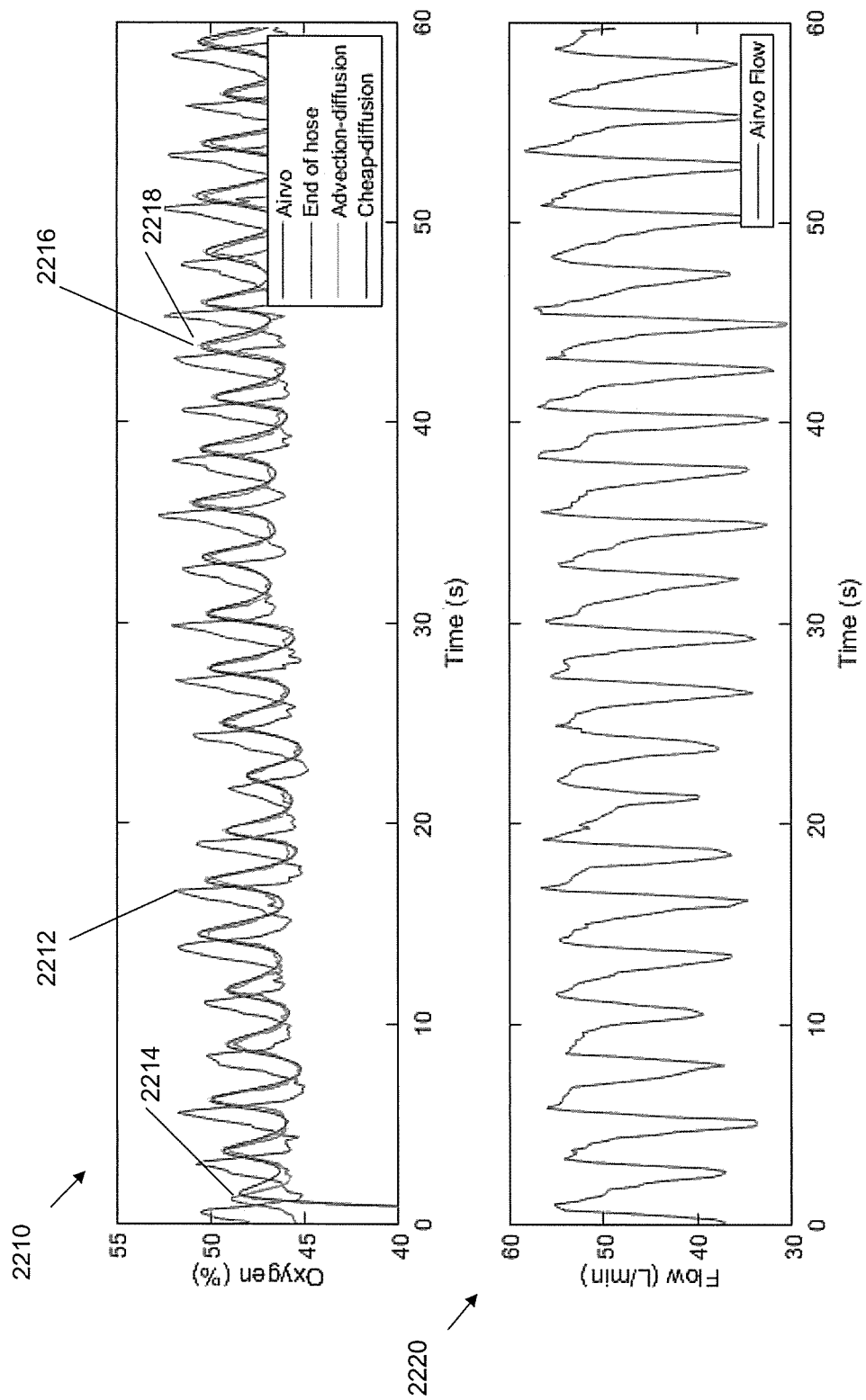
FIG. 22 illustrates an example of a chart illustrating example results of an oxygen content analysis in a breathing circuit.

FIG. 22 illustrates an example of chart 2210 illustrating example results of an analysis using the above described methods for determining oxygen content in the breathing circuit. Airvo 2212 provides a measured oxygen percentage at the gases composition sensors in the breathing circuit. End of hose 2214 provides a measured oxygen percentage at the patient interface. Advection-diffusion 2216 and Cheap-diffusion 2218 provide calculated estimates for the oxygen percentage at the patient interface. Chart 2220 illustrates a measured flow rate for the same time period.

Valve Control

The controller 13 can use a valve control algorithm can be used to estimate the start of the expiratory and inspiratory periods of the patient's breath cycle, and to adjust the valve prior to the start of these periods such that the desired FdO2 is being delivered during each period. Specifically, the controller 13 can estimate the transition from the inspiratory period to the expiratory period and adjust the valve such that the FdO2 at the patient interface begins to drop once inspiration has finished. Similarly, the controller 13 estimates the transition from the expiratory period to the inspiratory period and can adjust the valve such that the FdO2 at the patient interface returns to a target level by the time inspiration begins.

The primary priority is to deliver the target FdO2 to the patient, with conserving as much oxygen as possible being a secondary priority. As such, the ramping up and down of FdO2 can occur during the expiratory period, with the FdO2 at the patient interface being at the target level at the beginning of the inspiratory period and not beginning to drop until inspiration has finished.

There is a delay between adjusting the valve and measuring the change in FdO2 at the device and a further delay until the change occurs at the patient interface. The controller can compensate for the delay by predicting the beginning of expiration and adjusting the valve accordingly. In one embodiment, the beginning of expiration is estimated by observing the start of one expiratory period, and then predicting the next expiratory period's start time by using an estimation of the patient's respiratory rate.

Based on the current flow rate, the controller can calculate the travel time of the gases between the valve and the patient interface. The controller can use the travel time to determine when to reduce the FdO2 after one breath cycle has passed. For example, in one instance, if the patient has a respiratory rate of 20 breaths per minute, then one respiratory cycle would be 3 seconds. If the travel time is 0.5 seconds, the controller could shut off the valve 2.5 seconds after the start of the expiration period in order to begin dropping the FdO2 at the end of the upcoming inspiratory period.

Increasing the FdO2 poses a slightly more complicated challenge, as the controller has to ensure that the FdO2 at the patient interface is at or close to the target level by the start of the inspiratory period. To do this, the controller determines a deadline by which the FdO2 at the patient interface returns to the target level following the start of expiration. This deadline can be set at 1-1.5 breath cycles after the start of expiration less the travel time. Setting the deadline closer to 1.5 breath cycles less the travel time increases the amount of oxygen saved, but also increases the chance that the FdO2 at the patient interface might not be at the target level in time for the start of inspiration. The deadline may initially be set at a more conservative value (e.g., closer to 1 breath cycle less the travel time) and then moved to closer to its upper limit if the controller determines that the target FdO2 is being delivered to the patient interface by the start of inspiration. In use, the deadline may be around 1.4 breath cycles less the travel time.

To ensure that the target FdO2 threshold is being satisfied, the controller can adjust the valve to deliver the target FdO2 to the patient interface by the deadline. Due to diffusion of oxygen within the system, the FdO2 will ramp up over a period of time, even if a step change is executed in the valve control signal. As such, the controller can compensate for the diffusion by adjusting the valve at a determined time based on a calculated time that it will take for the FdO2 at the patient interface to ramp up to the FdO2 target threshold. The time period prior to the deadline can be referred to as the boost period.

The amount of oxygen conserved can be higher if the FdO2 is ramped up more quickly, as this allows the oxygen to cut for a longer portion of each expiratory period. The FdO2 can be ramped up more quickly by setting a higher target oxygen flow rate for the valve during the boost period. This increased target oxygen flow rate may exceed the oxygen flow rate used to achieve the target FdO2 at the target total flow rate.

Figure 23:
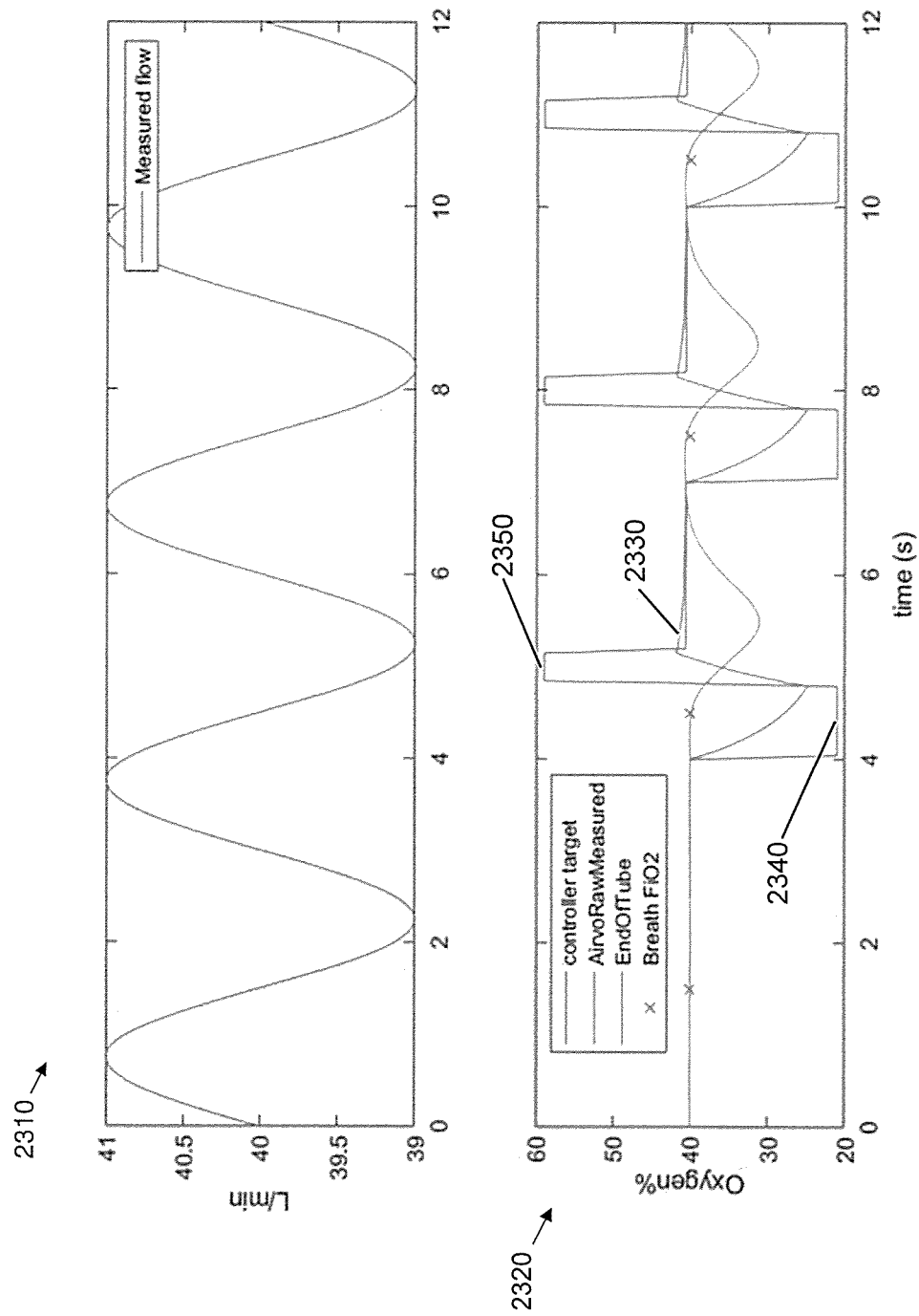
FIG. 23 illustrates an example of a control scheme of an oxygen conservation mode.

With reference to FIG. 23, an example of a control scheme of oxygen conservation mode is illustrated. In the illustrated embodiment, the controller can calculate three target levels for operation during the oxygen conservation mode. The first level 2330 is the target FdO2 for the patient. The target FdO2 for the patient can be determined for the patient using the processes described herein, such as open and/or closed loop control, or determined by a user. The second level 2340 is lower than the first level. The second level 2340 can be referred to as a low level or low period. Preferably the valve is entirely shut in order to conserve oxygen. The third level 2350 is higher than the first level. The third level can be referred to as the boost level or boost period.

The boost level can be an increase of the target oxygen flow rate as a multiple of the target FdO2 2330. The target oxygen flow rate can be the oxygen flow rate used to achieve the target FdO2 when the oxygen conservation mode is not running. In the illustrated example, the target oxygen flow rate is doubled during the boost period. For example, if the target FdO2 level 2330 is 40%, then the FdO2 for the boost level 2350 would be 59%. The increase of the target oxygen flow rate can be any value up to the maximum oxygen flow rate of the system, as increasing the oxygen flow rate beyond this would not increase the FdO2. For example, if the target FdO2 level 2330 is 80%, then the FdO2 for the boost level 2350 can be 100% (or lower if the 02 concentration of the 02 source is less than 100%).

Using a multiplication factor for increasing the oxygen during the boost period instead of always supplying maximum oxygen can help to reduce the risk of overshooting the target and can allow for additional adjustments to the flow rate in the event that inspiration starts earlier than predicted.

The boost period 2350 can extend until the deadline, after which the FdO2 can return to the target level 2330. The start of the boost period 2350 can be determined based on a calculated length of the boost period. The calculated length of the boost period can be dependent on a range of factors. In some embodiments, the length of the period is proportional to:

the length of time for which the oxygen is turned off (the low period 2340);
the difference between the oxygen flow rate at the first level 2330 and the oxygen flow rate at the second level 2340; and
the volume of the breathing circuit between inlets and the patient interface.

The length of the boost period 2350 can be inversely proportional to the difference between the oxygen flow rate at the first level 2330 and the oxygen flow rate at the third level 2350; and the target total flow rate.

The length of time for the boost period 2350 may be slightly adjusted based on a further estimated amount of diffusion that may be occurring. This estimation may be based on the total flow rate.

In the chart 2320 illustrated in FIG. 23, the controller target is the FdO2 target set by the control algorithm, wherein the oxygen valve is fully shut off for the low period 2340, and the FdO2 in the boost period 2350 is double the FdO2 of the first level 2330. AirvoRawMeasured is the signal from the gases composition sensor and EndOfTube is the estimated FdO2 calculated using the advection-diffusion equation. Breath FiO2 is the effective FdO2, which is calculated by taking the total amount of oxygen delivered during the inspiratory period and dividing it by the total volume of gases delivered for the same period. Chart 2310 illustrates a measured flow rate for the same time period.

The example in FIG. 23 is for a patient with a respiratory rate of 20 BPM, and a target flow of 40 LPM. The effective FdO2 is roughly at the target level, and the oxygen used has been reduced by about 15%.

In an alternative embodiment, the target oxygen flow rate for the boost period can be set to the same value as the target total flow rate, thereby resulting in maximum FdO2 during the boost period. This would allow for the sharpest possible ramp in FdO2 at the patient interface, but it also increases the risk of overshooting the target FdO2.

Determining Applicability of Oxygen Conservation

The controller 13 can make a determination of whether the conditions are suitable for executing an oxygen conservation mode of operation. The controller may determine based on one or more factors whether to execute the oxygen conservation mode. Additionally, the controller may continually monitor each of the various factors during operation to determine whether to enter or exit the oxygen conservation mode.

One factor is whether the modelling of the patient's respiratory cycle is sufficiently accurate. As the oxygen conservation mode relies on an accurate analysis of the patient's respiratory cycle. The controller may only execute the oxygen conservation mode if the analysis meets a defined confidence threshold for modelling the patient's respiratory cycle. The controller can calculate a confidence metric associated with the model of the patient's respiratory cycle and compare the calculated confidence metric to the confidence threshold.

Another factor is the amount of oxygen conserved. While the oxygen conservation mode conserves oxygen during the low period, the oxygen conservation mode also uses an increased amount of oxygen during the boost period. The controller may compare these two values and may only execute the oxygen conservation mode if the predicted oxygen savings during the low period is greater than the increase in oxygen usage during the boost period. Alternatively, the controller may execute the oxygen conservation mode only if the total reduction in oxygen used satisfies a defined threshold.

Another factor can be based on an analysis of the target flow rate and the respiratory rate. As can be seen in the advection term of the advection-diffusion equation, the travel time between the device and the patient interface increases when lower flow rates are used. As such, controlling the FdO2 becomes easier at higher flow rates. Additionally, as the patient's respiratory rate increases, the length of each breath cycle becomes shorter, and in turn the controller must transition between the various control periods more frequently, and the prediction of the inspiratory and expiratory transitions must be more precise.

Oxygen conservation becomes increasingly difficult in particular at low flow rates combined with high respiratory rates for two main reasons. Firstly, the travel time begins to get quite large in relation to the length of the breath cycle, and as such the valve changes need to be made further in advance of the inspiratory and expiratory transitions, which introduces greater possibility for error. Secondly, while frequent transitions in FdO2 can be achieved by the valve, the low flow rate of the gases allows for increased mixing before reaching the patient interface, and as such the resulting FdO2 oscillations become smaller. If the controller is to maintain target FdO2 during the inspiratory period, then the amount of oxygen that can be conserved becomes quite small.

The controller may additionally determine whether to execute the oxygen conservation mode based in part on the relationship between the target flow rate and the patient's respiratory rate. For example, execution of the oxygen conservation mode may be dependent on the ratio between the flow rate and the respiratory rate exceeding a threshold.

Execution of Oxygen Conservation Mode

Figure 24:
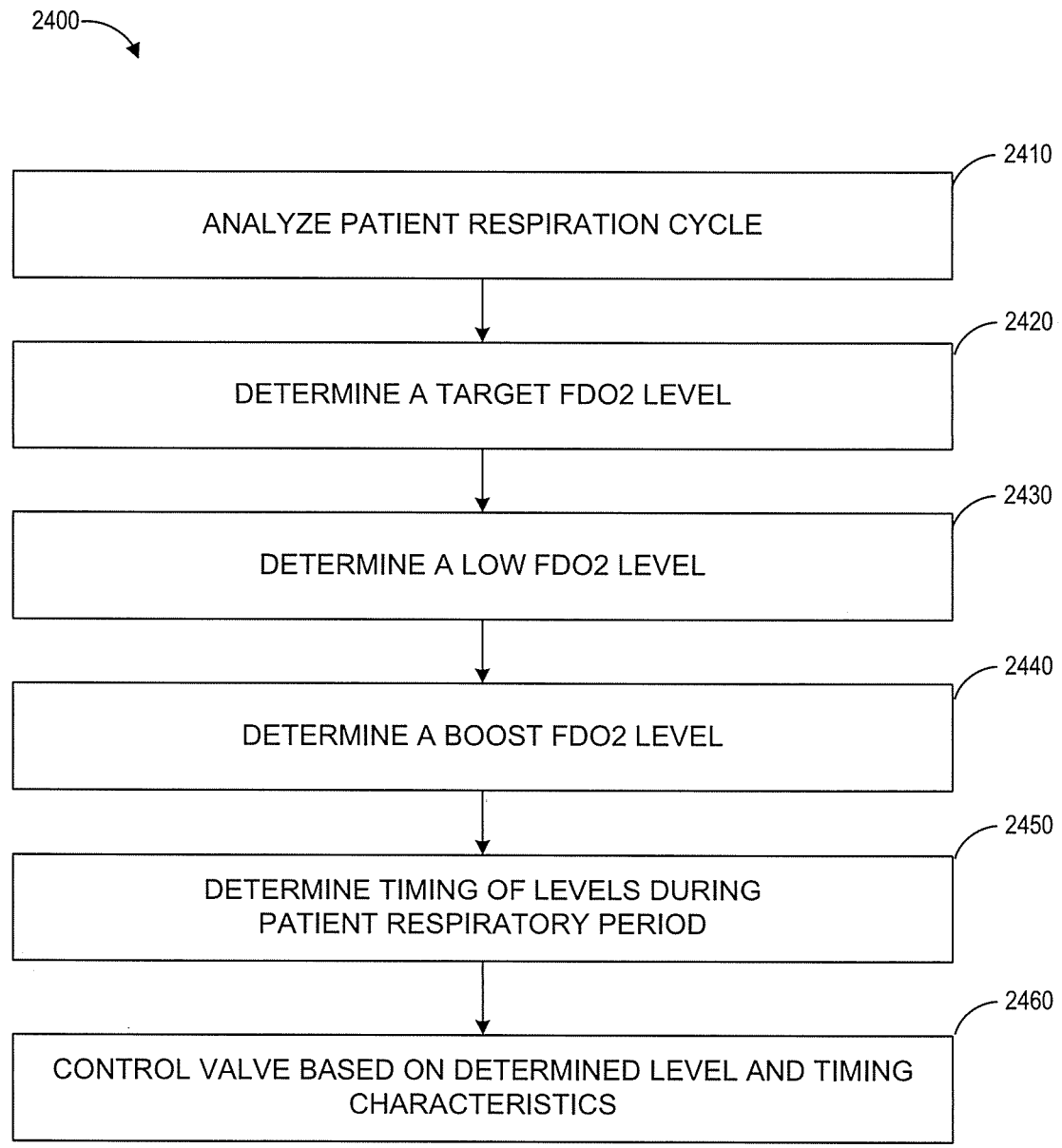
FIG. 24 illustrates an example of a flow chart for execution of an oxygen conservation mode during a therapy session.

FIG. 24 illustrates an embodiment of a flowchart for execution of an oxygen conservation mode during a therapy session. The process 2400 can be implemented by a controller or control system configured to control operation of a flow therapy apparatus. For example, the process 2400, in whole or in part, can be implemented by the controller 13 of the flow therapy apparatus 10.

At block 2410, the controller can analyse the patient's respiratory cycle. The controller 13 can be configured to determine a respiratory model of the patient based on the analysis. For example, the controller can generate a waveform representative of the patient's respiratory period. The respiratory period and/or phase can be determined using a combination of measurements. The patient's breath cycle can be determined through frequency analysis (such as an FFT) or time domain analysis (such as zero crossings).

At block 2420, the controller determines a target FdO2 level for the therapy session. This can be referred to as the first level. The target FdO2 level for the patient can be determined for the patient using the various processes described herein, such as open and/or closed loop control, or determined by a user. The target FdO2 level can represent a flow rate of supplemental gases (e.g., oxygen) required to achieve a target gases composition based on a total flow rate of gases.

At block 2430, the controller determines a low FdO2 level. The low FdO2 level is a second level and is lower than the target FdO2 level. The low FdO2 level may be an ambient oxygen level. The low FdO2 level may be as achieved by cutting off the flow of supplemental gases (e.g., oxygen) entirely. For example, the controller 13 can be configured to close the valve entirely.

At block 2440, the controller determines a boost FdO2 level. The boost FdO2 level is a third level and is higher than the target FdO2 level. The boost level can be an increase of the target oxygen flow rate as a multiple of the target FdO2. For example, the boost level can be double the target FdO2 level. The increase of the target oxygen flow rate can be any value up to the maximum oxygen flow rate of the system. Using a multiplicative factor for increasing the oxygen during the boost period instead of always supplying maximum oxygen can help to reduce the risk of overshooting the target and can allow for additional adjustments to the flow rate in the event that inspiration starts earlier than predicted.

At block 2450, the controller determines the timing of each level during a respiratory period. The controller can determine a duration and timing of a target FdO2 period, a low FdO2 period, and a boost FdO2 period. Each period can extend a portion of the respiratory period.

At block 2460, the controller controls operation of the valve based on the determined level and timing characteristics of the patient's respiratory cycle and determined characteristics for each level. The controller 13 can adjust the valve during operation based on determined periods such that the desired FdO2 is being delivered during each period. Specifically, the controller 13 can estimate the transition from the inspiratory period to the expiratory period and adjust the valve such that the FdO2 drops from the target FdO2 level to the low FdO2 level once inspiration has finished. The controller 13 can determine the transition from the low FdO2 level to the boost FdO2 level and can adjust the valve such that the FdO2 moves from the low FdO2 level to the boost FdO2 level. The controller 13 can estimate the transition from the expiratory period to the inspiratory period and can adjust the valve such that the FdO2 returns to the FdO2 target level from the boost FdO2 level by the time inspiration begins.

Additionally, the controller can continually monitor and adjust the various level and timing characteristics based on the continued analysis of the patient's respiration cycle. The controller can make a determination of whether the conditions are suitable for continued execution of the oxygen conservation mode. An embodiment of factors for determining whether to transition between operational modes is further described with respect to the process described in FIG. 25.

Process for Selecting Oxygen Conservation Mode

Figure 25:
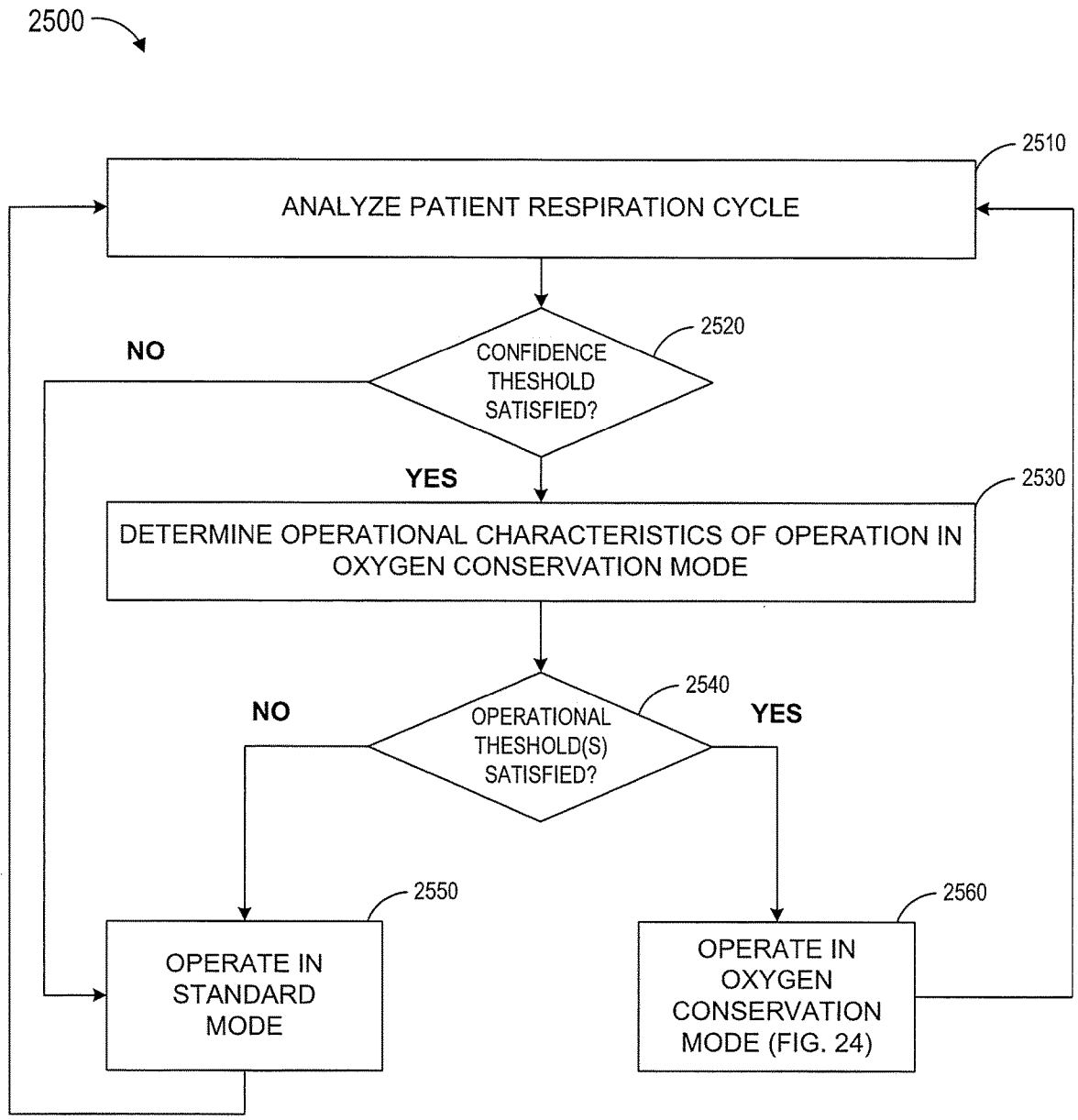
FIG. 25 illustrates an example of a flow chart for a process for determining whether to use an oxygen conservation mode during a therapy session.

FIG. 25 illustrates an embodiment of a flowchart for a process determining whether to use an oxygen conservation mode during a therapy session. The process 2500 can be implemented by a controller or control system configured to control operation of a respiratory apparatus. For example, the process 2500, in whole or in part, can be implemented by the controller 13 of the respiratory apparatus 10.

At block 2510, the controller can analyse the patient respiration cycle. The oxygen conservation process can be configured to execute the oxygen conservation process when the characterisation of the patient's respiratory cycle satisfies a certain confidence threshold. The oxygen conservation mode relies on an accurate analysis of the patient's respiratory cycle. The controller may only execute the oxygen conservation mode if the analysis meets a defined confidence threshold for modelling the patient's respiratory cycle. The controller can calculate a confidence metric associated with the model of the patient's respiratory cycle.

At block 2520, the controller can determine whether a confidence threshold for implementing the oxygen conservation mode has been satisfied by comparing the confidence metric to the confidence threshold. In situations where the patient's respiratory cycle cannot be confidently characterised and the confidence threshold is not satisfied, the oxygen conservation process can operate in the standard therapy mode and the process can proceed to block 2550. If the threshold has been satisfied, the process proceeds to block 2530.

At block 2530, the controller can determine operational characteristics of operation in the oxygen conservation mode. The operational characteristics can include oxygen conservation characteristics. The oxygen conservation characteristics can be used to determine how much oxygen will be conserved by operating in the oxygen conservation mode. The oxygen conservation mode conserves oxygen during the low period, the oxygen conservation mode also uses an increased amount of oxygen during the boost period. The system can determine and compare these two values in order to evaluate the predicted amount of oxygen conservation. The operation characteristics can include the target flow rate and the patient's respiratory rate. Oxygen conservation can be increasingly difficult in particular at low flow rates combined with high respiratory rates. The controller may determine a ratio between the flow rate and the respiratory rate.

At block 2540, the controller can determine whether an operational threshold for implementing the oxygen conservation mode has been satisfied. The controller may compare oxygen conservation characteristic to the oxygen conservation threshold values in order to determine whether the total reduction in oxygen satisfies the oxygen conservation threshold. In addition to or in the alternative, the ration of the flow rate and the respiratory rate may be compared to a separate threshold. If any of the defined thresholds have not been satisfied, the process proceeds to block 2550. If the threshold has been satisfied, the process proceeds to block 2560.

At block 2550, the controller operates the system in standard mode (as described in more detail herein) where the controller is configured to meet the target FdO2 at substantially all points of the patient's respiratory cycle. The controller can continue to analyse the characteristics of the patient's respiratory cycle at block 2510 to determine whether the controller continues to operate in standard mode or transitions to oxygen conservation mode.

At block 2560, the controller operates the system in oxygen conservation mode where the controller operates the valve using three different levels as described in more detail in FIG. 24. The controller can continue to analyse the characteristics of the patient's respiratory cycle at block 2510 to determine whether the controller continues to operate in oxygen conservation mode or transitions to standard mode.

The analysis to determine whether to continue to use or transition into the oxygen conservation mode may be performed at determined intervals. For example, the determined intervals may be performed every respiratory period, every other respiratory period, or after a defined number of respiratory periods. The analysis may be performed based on any suitable time increment, such as every second, every five seconds, or any determined time increment. The determined intervals may be based on operational characteristics of the current mode and/or patient characteristics.

Motor and/or Sensor Module Configuration

Figure 3:
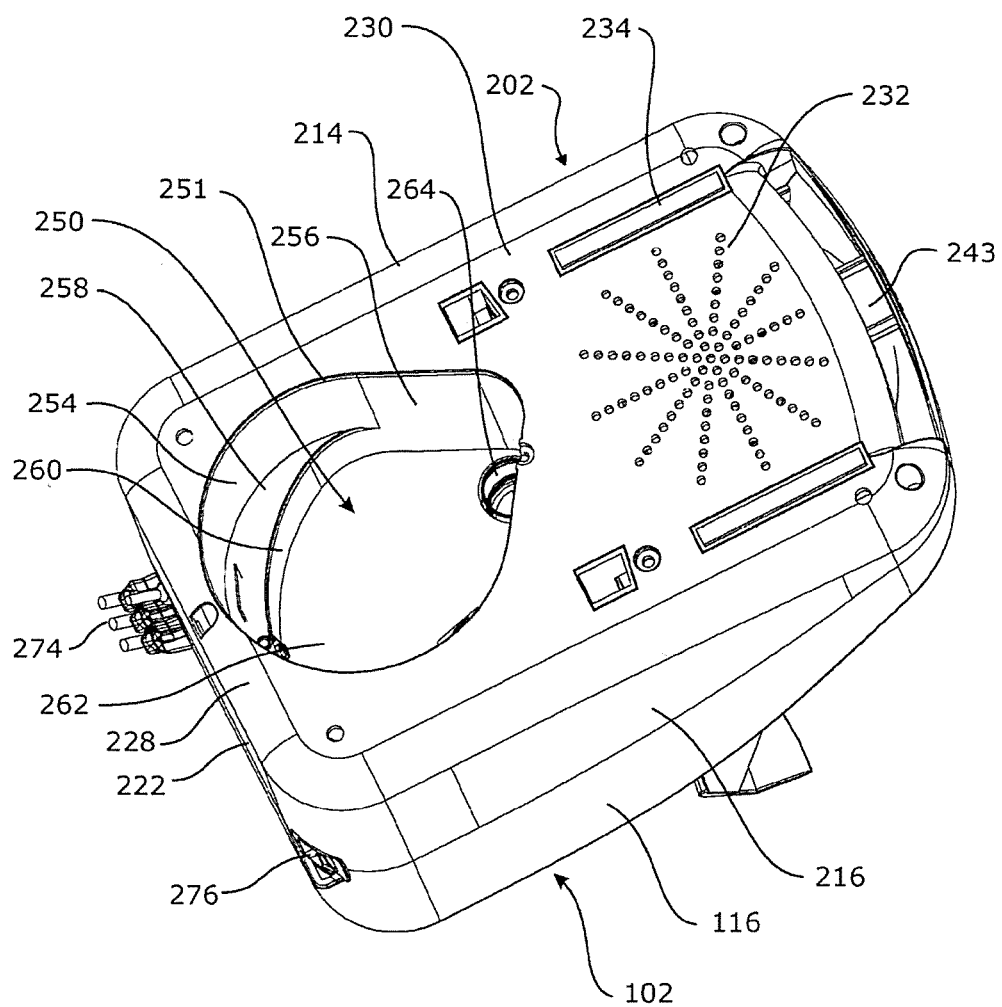
FIG. 3 is a first underside perspective view of the main housing of the flow therapy apparatus showing a recess inside the housing for the motor and/or sensor module sub-assembly.
Figure 4:
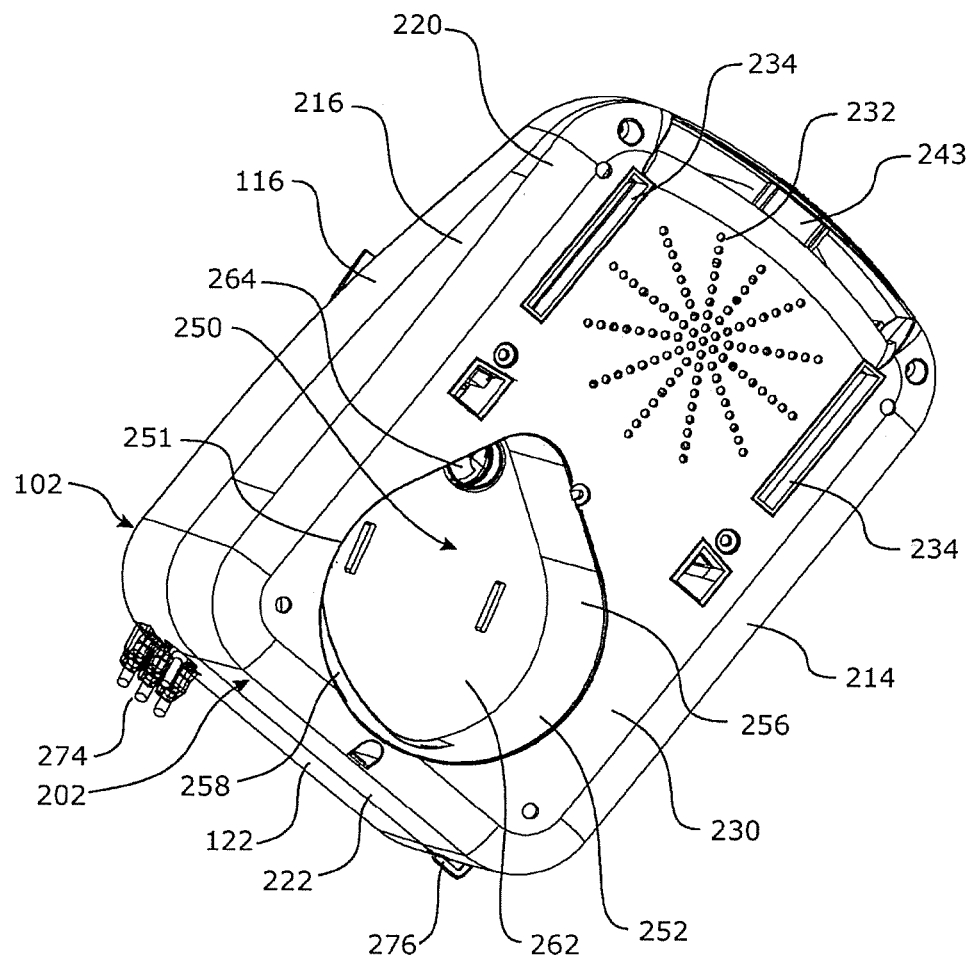
FIG. 4 is a second underside perspective view of the main housing of the flow therapy apparatus showing the recess for the motor and/or sensor module sub-assembly.
Figure 5:
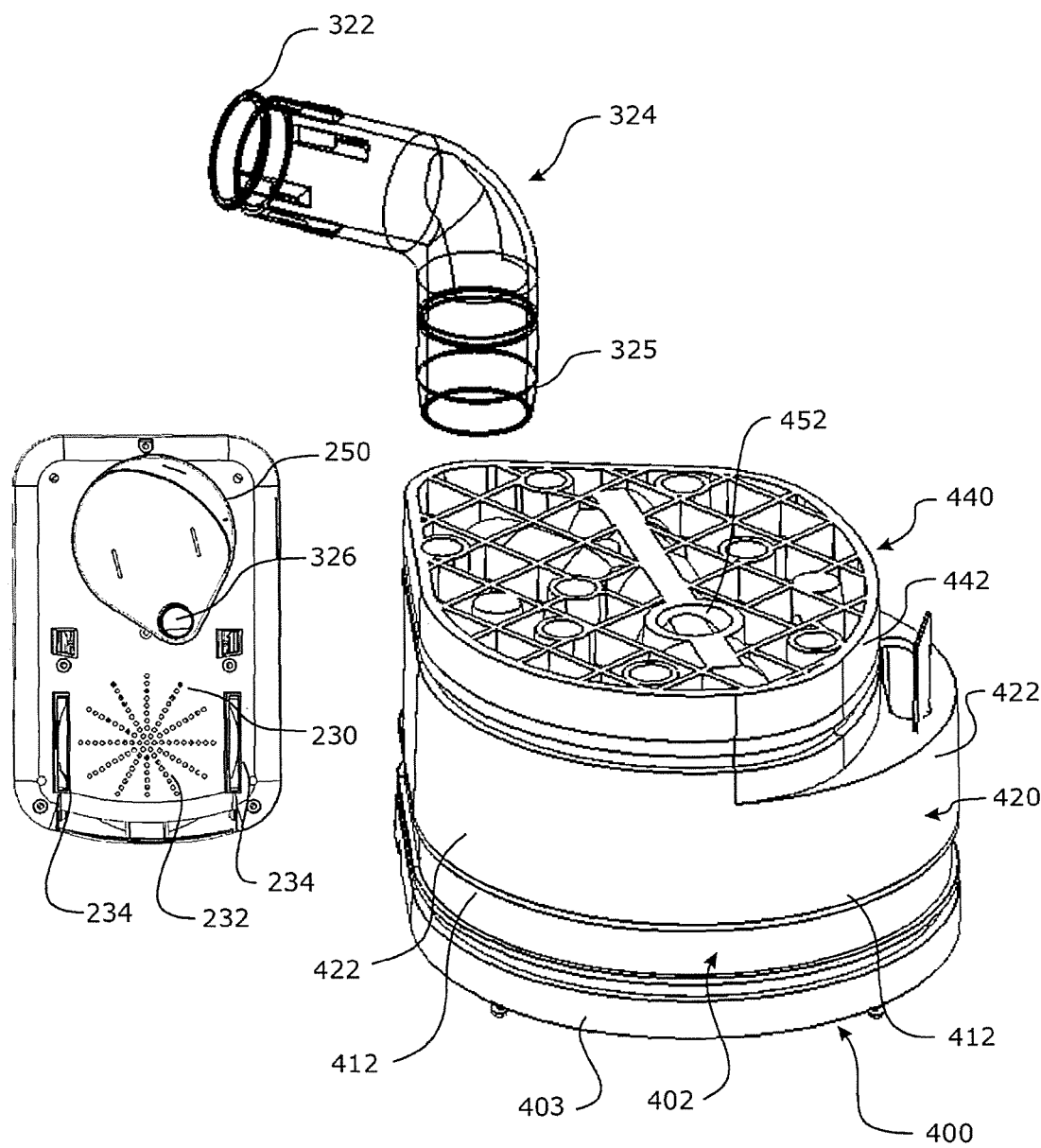
FIG. 5 is a perspective view of the motor and/or sensor subassembly, underside of the main housing, and fixed elbow of the flow therapy apparatus.

A configuration of a flow therapy apparatus 10 is illustrated in FIGS. 3 to 5. The flow therapy apparatus comprises a main housing 100. The main housing 100 has a main housing upper chassis 102 and a main housing lower chassis 202.

As shown in FIGS. 3 and 4, the lower chassis 202 has a motor recess 250 for receipt of a removable or non-removable motor and/or sensor module 400 which is shown in FIGS. 3 to 5 and will be described in further detail below. A recess opening 251 is provided in the bottom wall 230 adjacent a rear edge thereof, for receipt of a removable or non-removable motor/sensor module 400 which is shown in FIGS. 3 and 5 and will be described in further detail below.

FIGS. 5 to 8 show the motor and/or sensor module or sub-assembly 400 in greater detail. As discussed above, the lower chassis 202 comprises a recess 250 for receipt of the motor and/or sensor module 400.

In the form shown in FIGS. 5 to 8, the motor and/or sensor module 400 comprises a stacked arrangement of three main components; a base 403 of the sub-assembly 400 (on which is positioned the motor 402), an outlet gas flow path and sensing layer 420 positioned above the base 403, and a cover layer 440. The base 403, the sensing layer 420, and the cover layer 440 assemble together to form a sub-assembly housing that has a shape that is complementary to that of the recess 250 so that the sub-assembly 400 can be received in the recess 250. The base 403 is configured to close the recess opening 251 when the sub-assembly 400 is positioned in the recess 250. The sub-assembly 400 may be maintained in position in the recess in any suitable way such as with fasteners, clips, or a quick release arrangement for example, or fixed in a non-removable manner.

The sensing layer comprises a gas flow path with one or more sensors, the gas flow path arranged to deliver gas to the outlet port of the housing.

The motor 402 has a body 408 that defines an impeller chamber that contains an impeller. The motor 402 could be any suitable gas blower motor, and may for example be a motor and impeller assembly of the type described in published PCT specification WO2013/009193. The contents of that specification are incorporated herein in their entirety by way of reference.

A gases outlet 406 is in fluid communication with a gases inlet of the outlet gas flow path and sensing layer 420, which is stacked on top of the motor. This layer 420 comprises a body 422 which comprises a plurality of mounting legs 425 that can be inserted into a plurality of mounting slots (not shown) of the base 403 to secure the body 422 to the base 403. In one configuration, the body 422 defines a gas flow path that couples the gases outlet 406 with the gases inlet of the gas flow path and sensing layer 420.

The body 422 defines a lower portion 426 of a sensing and gas flow path. The cover layer 440 has a body 442 that defines the upper portion 446 of the sensing and gas flow path, with the shape of the upper and lower portions 426, 446 corresponding substantially to each other.

Figure 6:
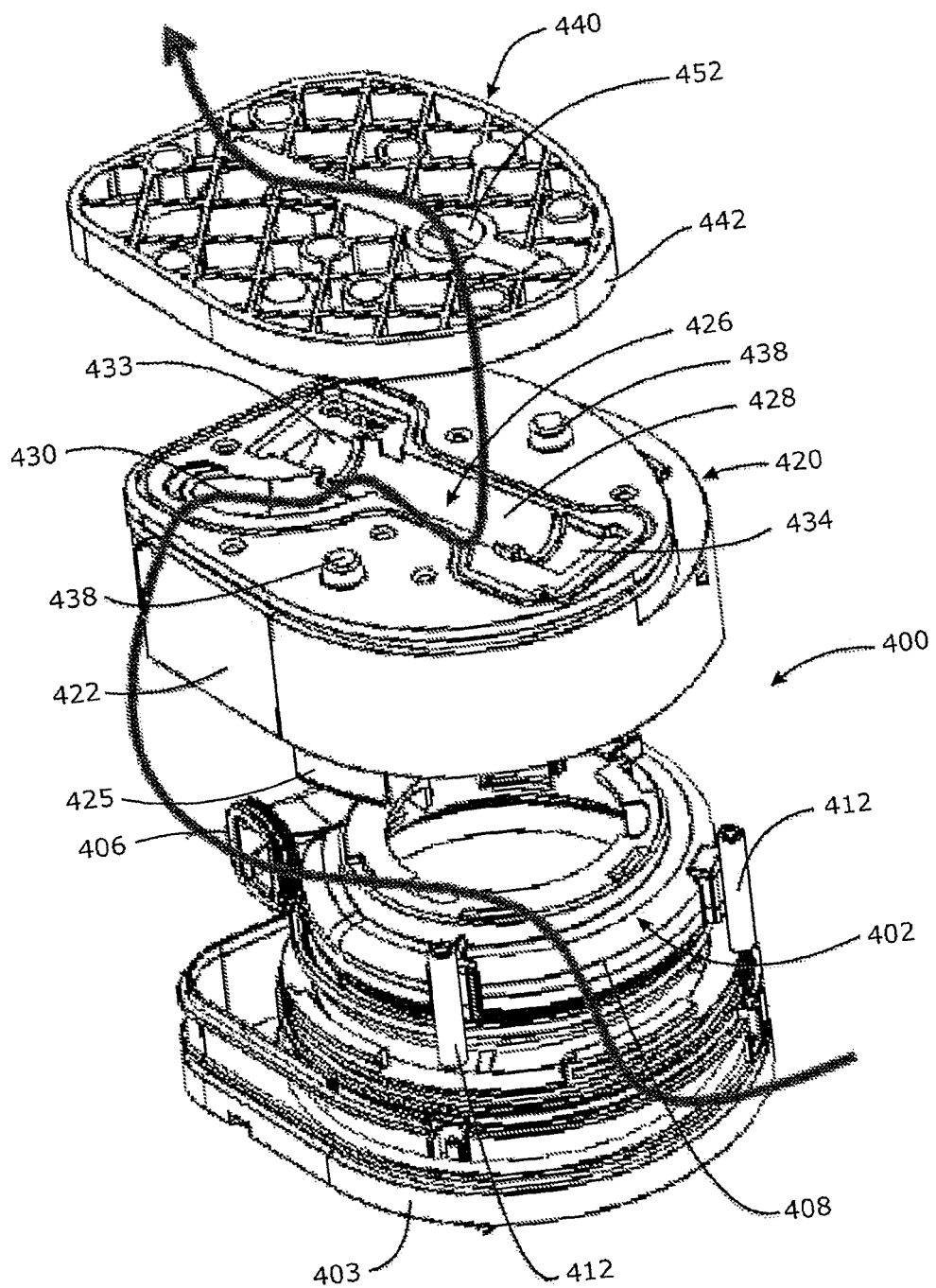
FIG. 6 is an exploded perspective view of components of the motor and/or sensor sub-assembly schematically showing by way of an arrow the gas flow path through the sub-assembly.
Figure 7:
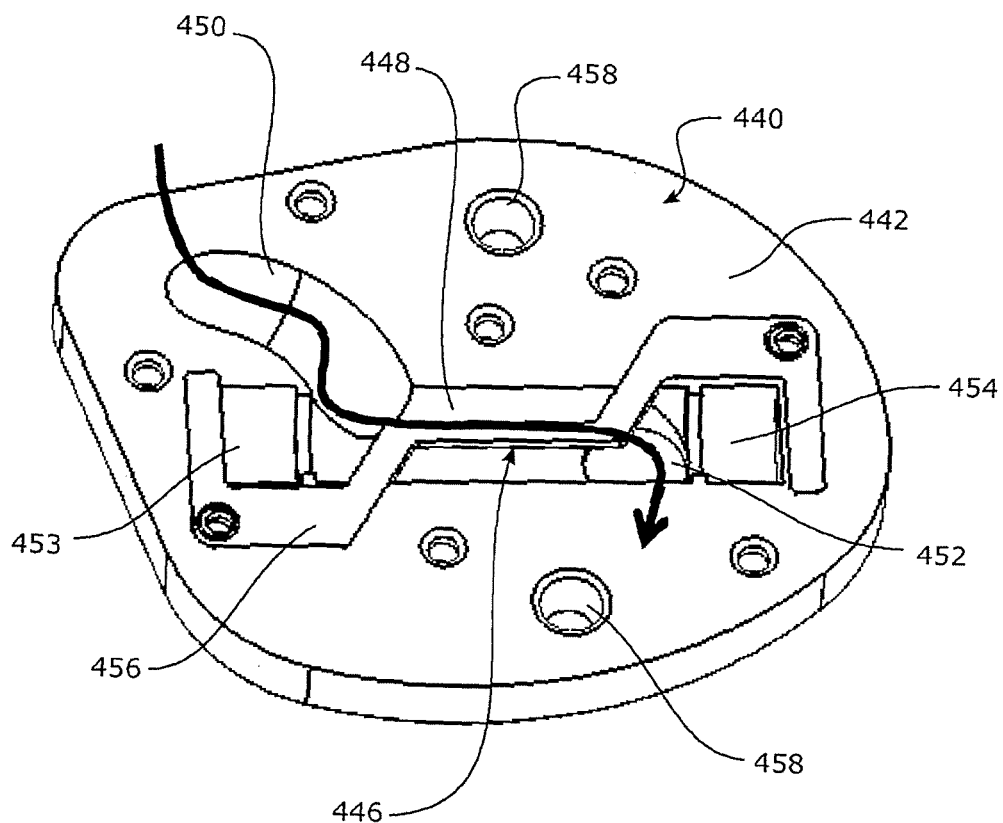
FIG. 7 is an underside view of a cover and sensing PCB of the motor and/or sensor sub-assembly showing the position of sensors.

As shown in FIGS. 6 and 7, the gas flow path comprises a linear elongate gas flow portion 428, 448. The inlet is in fluid communication with a tangential entrance portion 430, 450 of the gas flow path, which is located at or adjacent an entrance end of the linear elongate portion 428, 448 of the gas flow path. Recesses 433, 453 and 434, 454 may be provided at opposite ends of the linear elongate portion of the gas flow path.

A gas flow outlet port 452 extends vertically through the body 442 of the cover layer 440, and is located at or adjacent an opposite exit end of the linear elongate portion 428, 448 of the gas flow path. The gas outlet port 452 is in fluid communication with an upper portion of the motor recess 250, which in turn is in fluid communication with the gas flow passage. Again, due to the wall 252 and ceiling 262 configuration of the recess 250, if there is gas leakage from the motor/sensor module 400, that will be vented to atmosphere rather than entering the portion of the main housing 100 that contains the bulk of the electronics and control equipment. The recess 250 may comprise spacer(s), such as lugs that protrude downwardly from ceiling 262 as shown in FIG. 4, to maintain a suitable spacing for gas flow from the gas outlet port 452 and the ceiling of the recess 262.

It can be seen from FIG. 6 that that at least part of the gas flow path through and out of the motor and/or sensing module 400 has a tortuous or sinuous configuration. For example, the direction of gas flow travel through the elongate portions 428, 448 is generally opposite to the direction of gas flow travel from the gas outlet port 452 to the entrance of the gas flow passage through elbow 324.

Figure 8:
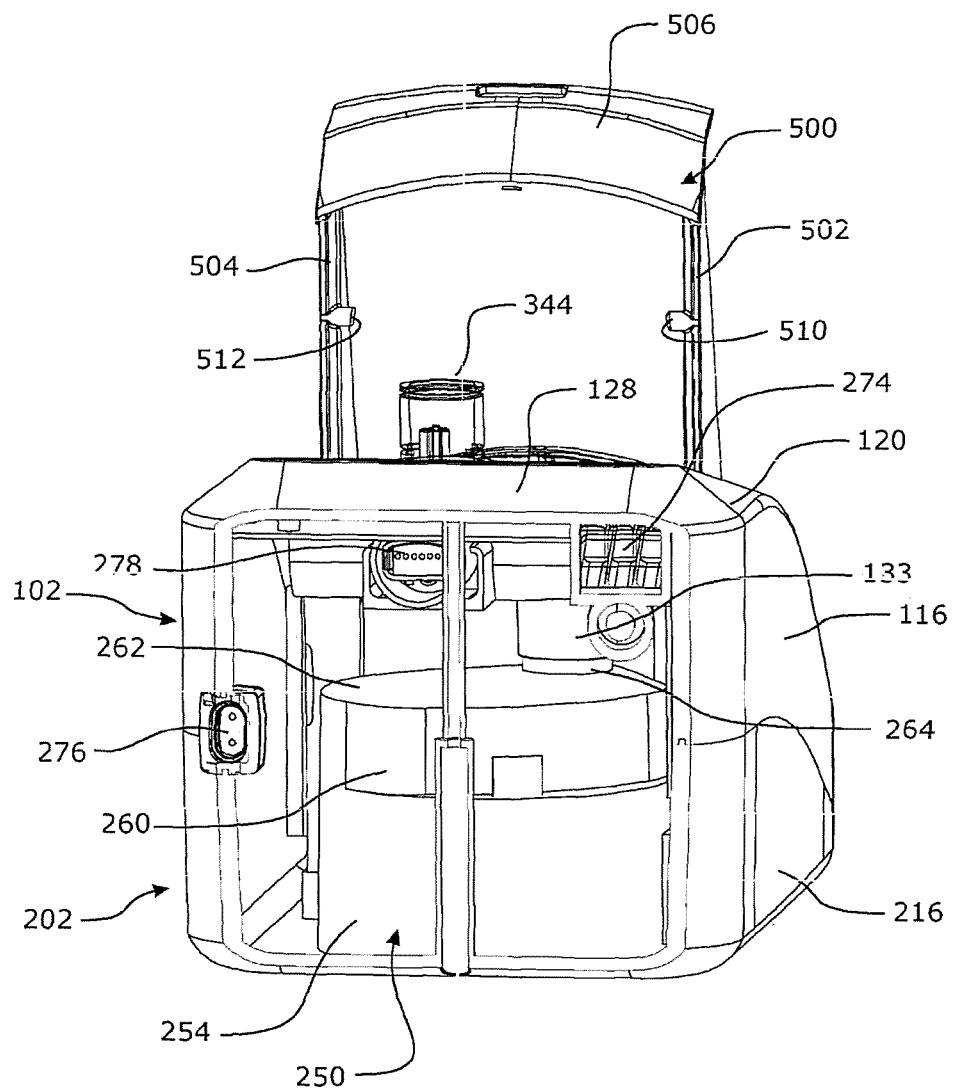
FIG. 8 is a rear perspective view of the flow therapy apparatus sectioned adjacent the rear edge of the apparatus, showing the arrangement of a portion of the main housing that provides the recess for receipt of the motor and/or sensor sub-assembly.
Figure 9:
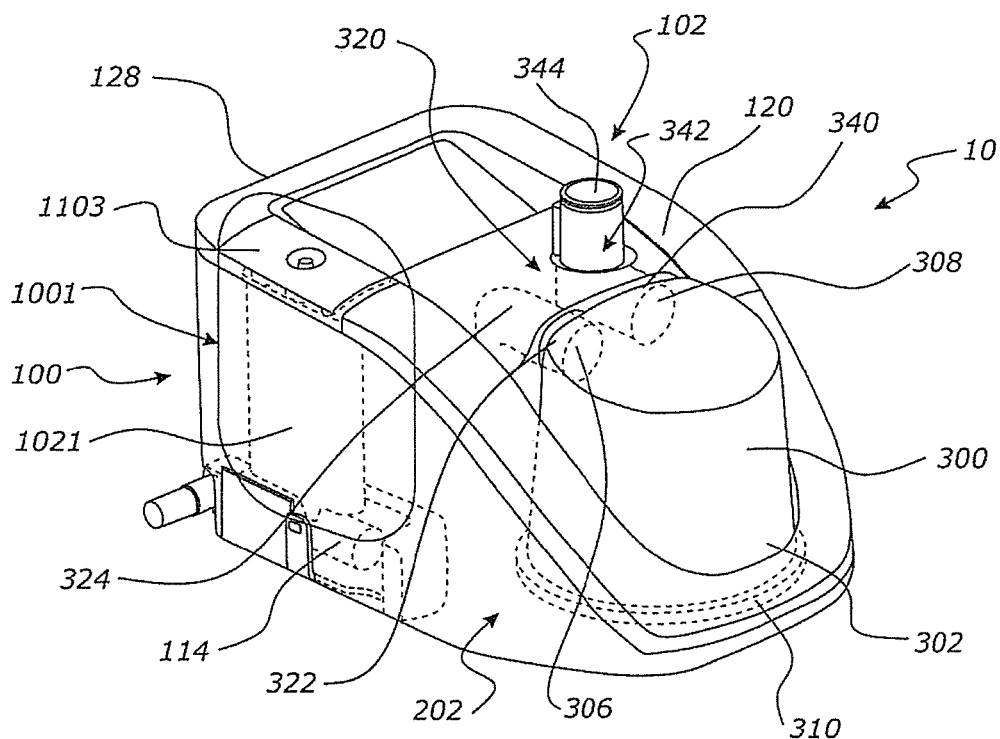
FIG. 9 is a left front perspective view of the flow therapy apparatus.
Figure 10:
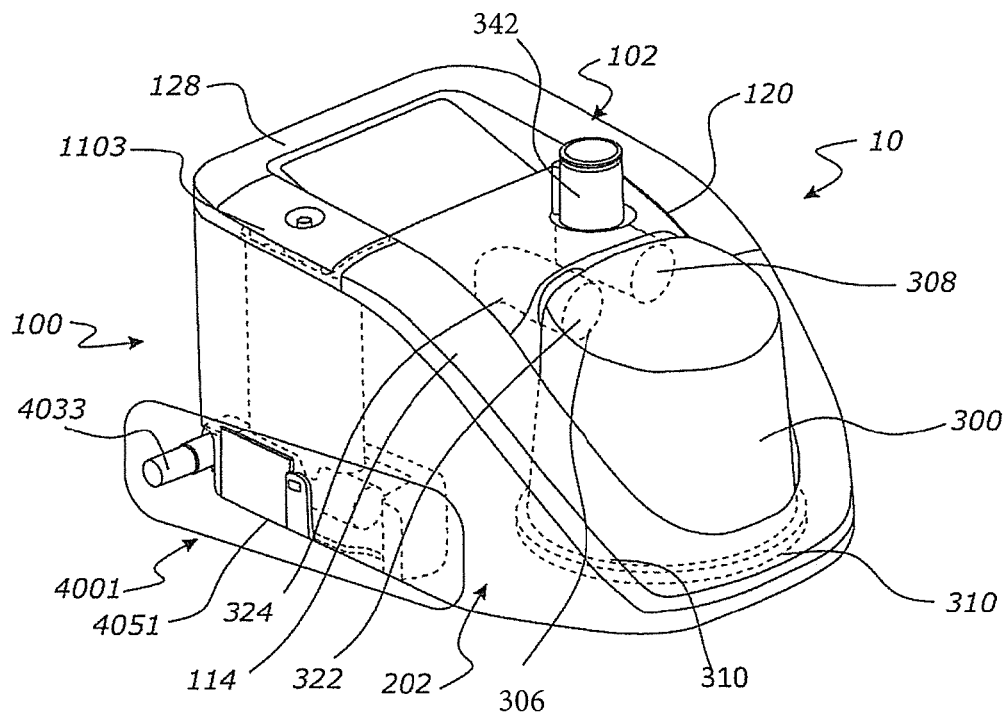
FIG. 10 is a left front perspective view of the flow therapy apparatus.
Figure 11:
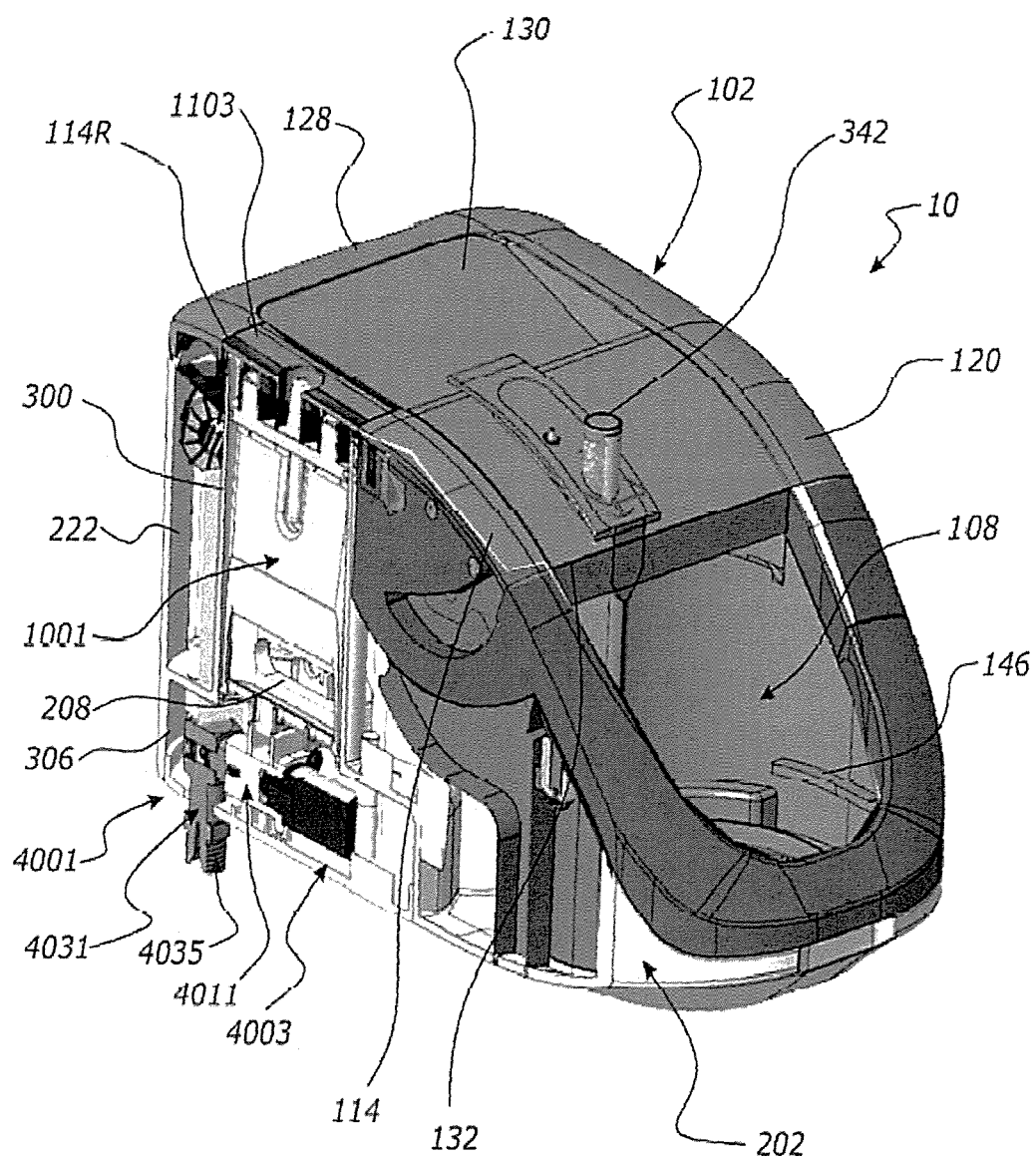
FIG. 11 is a left front perspective partial cutaway view showing the valve module and the filter module.
Figure 12:
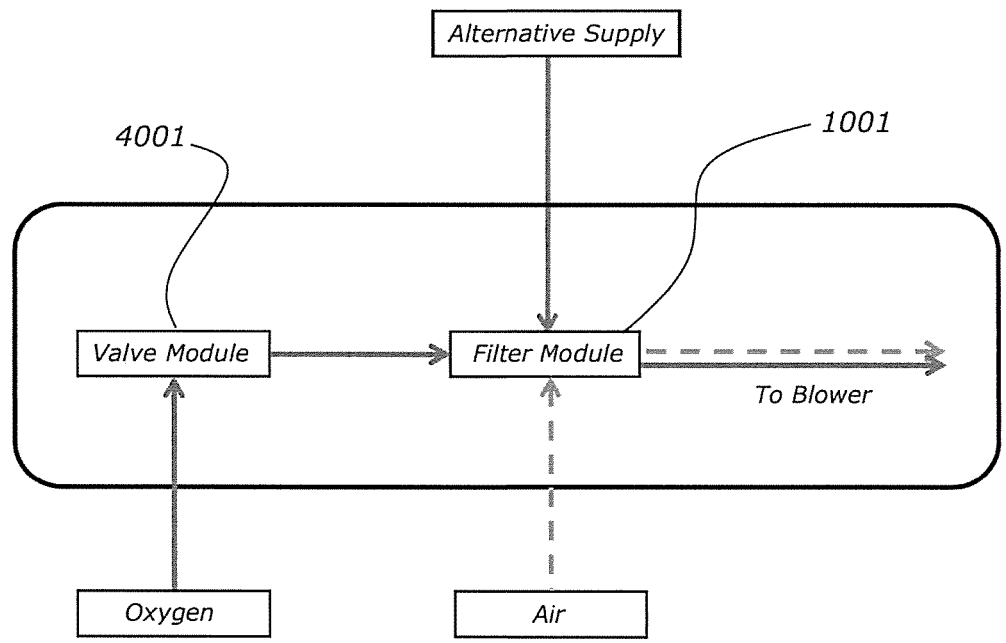
FIG. 12 is a schematic gas flow path diagram for the filter module and the valve module, with the solid line arrows representing the flow of oxygen (or another gas), and the dashed line arrows representing the flow of ambient air.
Figure 13:
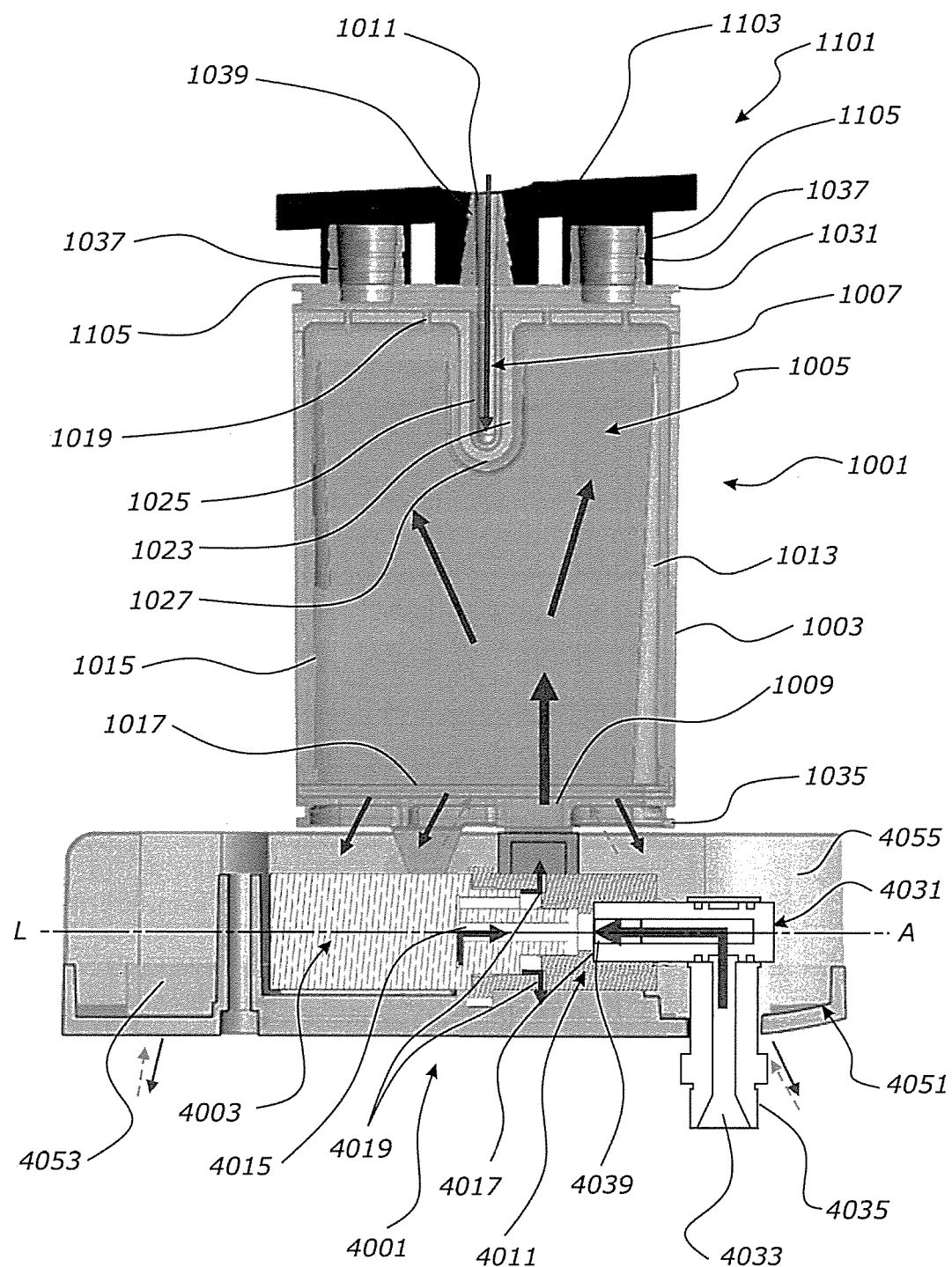
FIG. 13 is a sectional view showing the gas flow path through the filter module and the valve module.
Figure 14:
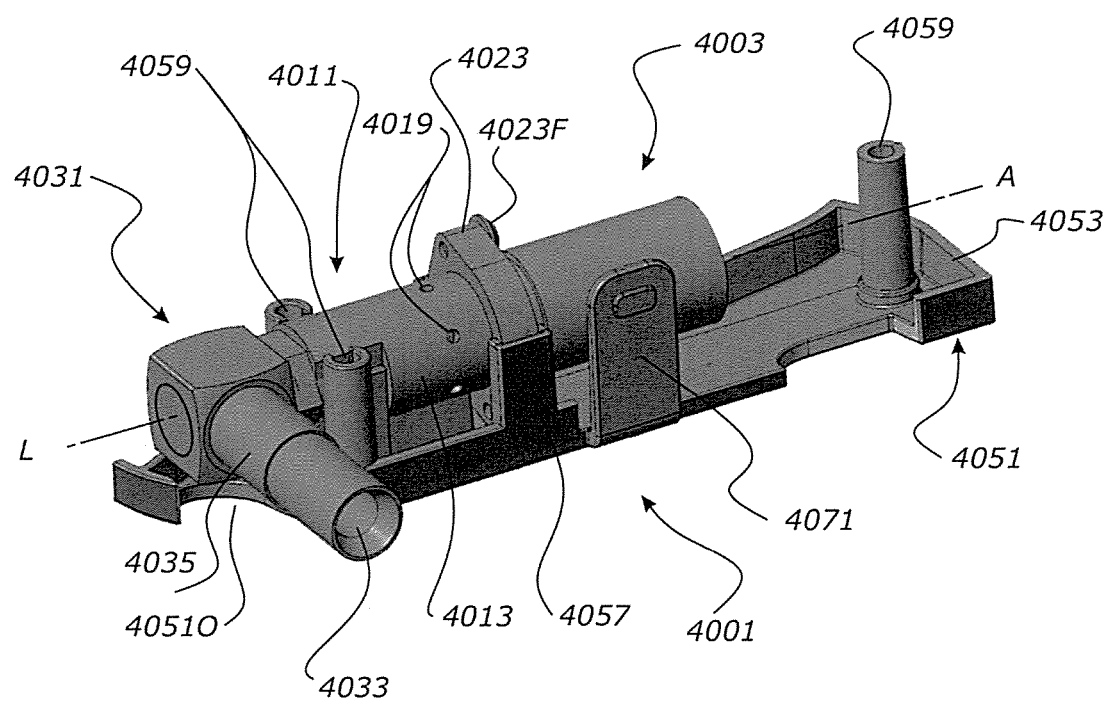
FIG. 14 is a rear side overhead perspective view of a first configuration valve module.
Figure 15:
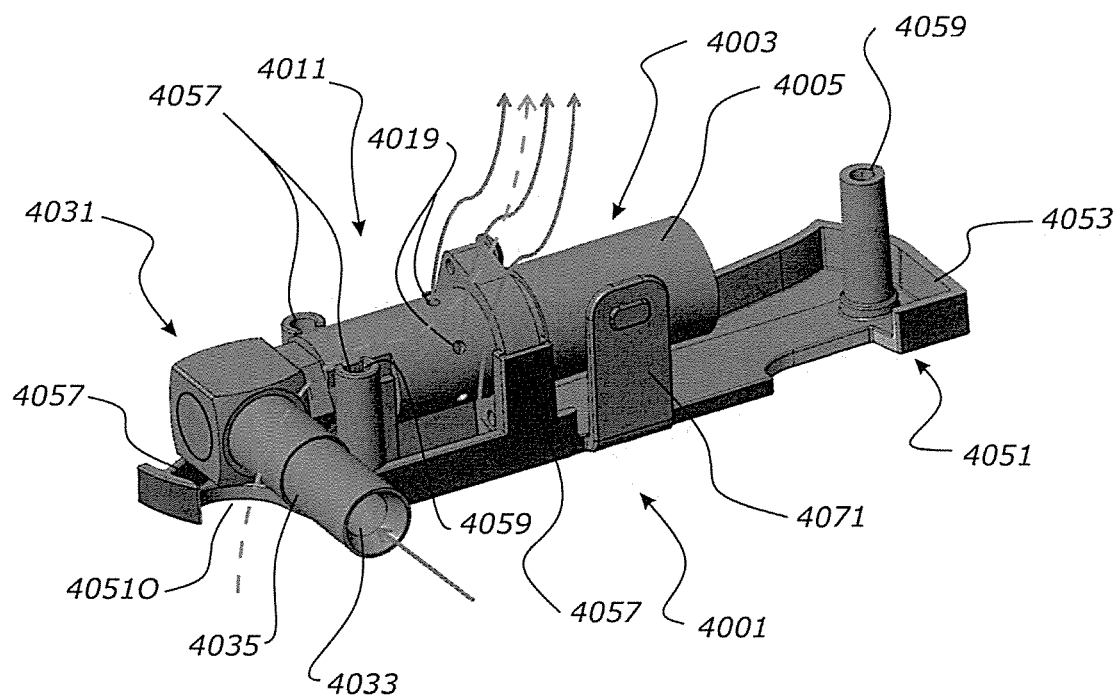
FIG. 15 is a rear side overhead perspective view showing the gas flow paths through the first configuration valve module, with the solid line arrows representing the flow of oxygen (or another gas), and the dashed line arrow representing the flow of ambient air.
Figure 16:
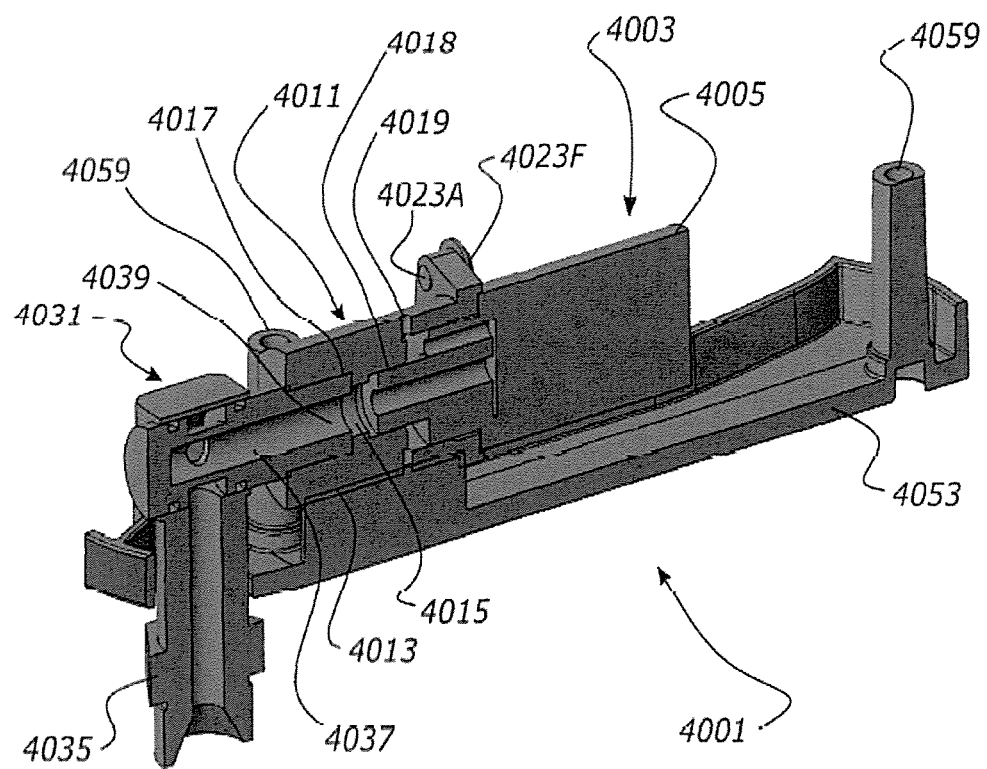
FIG. 16 is a sectional view through the first configuration valve module.
Figure 17:
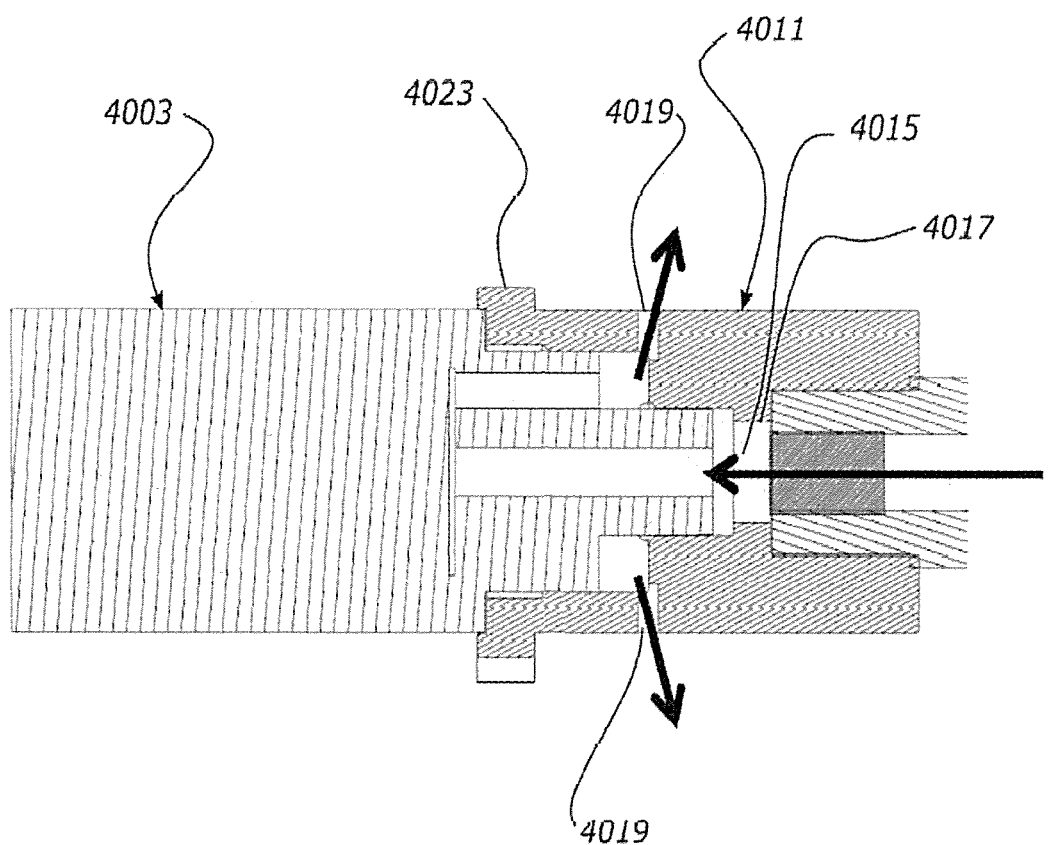
FIG. 17 is a sectional view showing the coupling of, and gas flow path through, the valve and valve manifold of the first configuration valve module.

As shown in FIGS. 7 and 8, the cover layer 440 comprises a sensing printed circuit board (PCB) 456. The cover layer 440 may also comprise one or more temperature sensors such as thermistors that sit in the elongate portion 428, 448 of the gas flow path. One sensor will measure gas temperature and the other can act as a redundant temperature sensor. Alternatively, one of the thermistors could be used as a reference flow sensor (e.g. via use as a constant-temperature thermistor), and the measured temperatures could be used to determine the gas flow rate through the portion 428, 448 of the gas flow path. The one or more temperature sensors may be located on a portion of the sensing PCB 456 that faces the gas flow. The sensing PCB 456 may additionally comprise other sensors including but not limited to pressure sensors, humidity sensors and dew point sensors.

One or both of the electronics boards 272 will be in electrical communication or coupled with the sensors to process information received from the sensors and operate the apparatus 10 based on the information received from the sensors.

In an alternative configuration, the motor/impeller unit may be provided remotely from the apparatus 10. In that configuration, the module received in the recess 250 may only comprise a gas flow path and various sensors, to deliver gases to the fixed elbow 324 and thereby to the liquid chamber 300. In an alternative configuration, the module received in the recess 250 may only comprise the motor and a gas flow path, but no sensors.

In another alternative configuration the motor and/or sensor module 400 may not be removable from the recess 250, but instead may be permanently mounted therein. The benefits of the gas isolation from the electrical/electronics components would still be provided in that configuration.

The flow path is compact, and has reduced turns/sharp turns which reduces flow separation and reduces resistance to flow.

The arrangement of the motor and flow path provides another layer of isolation because of the wall arrangement.

Having a modular motor and/or sensor module enables the various parts of the module to be taken apart if needed for cleaning and/or servicing.

There are advantageously no leak paths in the motor and/or sensor module. While the motor and/or sensor module may be a potential leak point, a leak in that region would result in the oxygen venting to atmosphere or into the liquid chamber.

Valve Module

FIGS. 9 to 17 show a first configuration of a valve module 4001. The valve module 4001 controls the flow of oxygen and/or other gases entering the gas flow path of the apparatus 10, and enables the apparatus 10 to regulate the proportion of oxygen entrained in the airflow. The valve module is formed as a modular unit for ease of manufacture, assembly, servicing, or replacement, for example in the event of malfunction, routine maintenance, or future upgrade/improvement.

The valve module 4001 inserts vertically in an upward direction into the valve module receptacle 306 in the lower chassis 202 of the main housing. In alternative configurations, the valve module may be insertable in a different direction into the housing, such as a forward direction, downward direction, rearward direction, or side direction. The valve module 4001 is removably engageable with the main housing of the apparatus, such that the valve module 4001 is substantially received in the housing and is accessible from the exterior of the housing. In some configurations, the valve module 4001 can be fixed within the main hosing and not removable. Part of the valve module 4001 is arranged to be substantially flush with an external wall of the housing when the valve module is removably engaged with the housing.

Because the valve module is modular and is accessible from the exterior of the housing, the valve module can be replaced without significant disassembly of the apparatus 10 and without compromising seals of the housing of the apparatus. Because the valve module 4001 is substantially received within the housing, when the valve module is engaged with the housing it becomes integrated with the housing and does not increase the size or bulk of the housing. Additionally, the components of the valve module such as the valve 4003 and valve manifold 4011 described below are protected in use because they are positioned within the valve carrier 4051 and main housing of the apparatus in use. This configuration significantly reduces the likelihood of damage of the valve module and valve module components if the apparatus 10 is inadvertently knocked or dropped.

The valve module comprises a flow control valve 4003 that is arranged to control a flow of gas through a valve manifold 4011. The valve is arranged to control a flow of gas into part of the apparatus. For example, the valve may be arranged to control a flow of gas to a filter module 1001. Alternatively, the valve 4003 may be arranged to control a flow of gas to another part of the apparatus. The valve module 4001 and filter module 1001 are positioned upstream of the blower 402 and motor and/or sensor module 400. In some embodiments, the valve module 4001 and filter module 1001 are positioned downstream of the blower 402.

The valve 4003 comprises a cylindrical body 4005 and a valve member in the body.

The flow control valve could be a solenoid valve, could be motor-driven, or could be piezo-operated for example.

In a solenoid valve, the valve member is actuated between open and closed positions. The solenoid valve may be a proportional valve. The extent of gas flow through the valve (i.e. due to the size of the valve opening) is relative to the electrical current supplied to the valve.

Alternatively, the solenoid valve may be controlled with a modulated input signal, so that the valve is modulated between open and closed positions.

The valve 4003 could be a needle valve, plunger valve, gate valve, ball valve, butterfly valve, globe valve, etc. The valve may be of the pressure compensated type.

In some configurations, the valve is a normally-closed valve; that is, the valve is closed when powered off. That will prevent a connected gas supply line continuously releasing oxygen or other gas when the apparatus is powered off. In some alternative configurations, the valve is a normally-open valve.

In some configurations, the valve 4003 is an electrically actuated proportional solenoid valve. For example, the valve may be a μProp valve available from Staiger GmbH & Co. KG of Erligheim, Germany, may be an Asco 202 series Preciflow valve available from Emerson/Asco Valves of New Jersey, or may be any other suitable type of valve.

The valve may have a coaxial inlet-outlet configuration.

The valve module 4001 comprises a valve manifold 4011 which has a body 4013 defining a gas flow path 4015 between a valve manifold gases inlet 4017 and one or more valve manifold gases outlets 4019. The gases inlet 4017 of the valve manifold is axially located at or toward an end of the valve manifold. In some configurations the valve manifold 4011 has a single gases outlet 4019, which is radially located on the valve manifold. In some configurations, the valve manifold 4011 comprises a plurality of valve manifold gases outlets 4019 that are radially located about the valve manifold. The valve manifold outlets 4019 are arranged to deliver gases from the valve manifold gases inlet 4017 to a gases inlet of the filter module 1001. The radial arrangement of outlet(s) 4019 assists with directing oxygen (or other gas) towards the filter module, minimizing loss of oxygen and enhancing entrainment efficiency. The valve 4003 is arranged to control a flow of gas from the valve manifold gases inlet 4017 to the valve manifold gases outlet(s) 4019. When the valve is 'closed', gas flow from the gases inlet 4017 to the gases outlet(s) 4019 is prevented. When the valve is 'open', gas flow from the gases inlet 4017 to the gases outlet(s) 4019 is enabled.

An end 4018 of the valve manifold 4011 opposite to the gases inlet receives and sealingly engages with the valve 4003 such that the valve and valve manifold are in fluid communication. The end 4018 comprises a flange 4023 to mount to the valve. The flange 4023 has apertures 4023A to receive fasteners 4023F to fasten the manifold to the valve 4003. O-ring(s) may be provided about the periphery of the interface between the valve 4003 and the valve manifold 4011 to sealingly engage the valve with the valve manifold.

The valve manifold 4011 directs/disperses oxygen from the valve via radially located gases outlets 4019. In some embodiments, a single gases outlet 4019 is provided in the valve manifold. As oxygen passes through the outlet(s), noise is generated. Because the apparatus may be used in medical and/or home environments in close proximity to the patient, it is desirable to minimize the noise produced.

Additionally, or alternatively, a hood, duct, or channel may be formed around, in proximity to, or in fluid communication with the valve manifold outlet(s) 4019 in order to reduce noise. Additionally and/or alternatively, foam, or the like, may be placed around the valve manifold, in proximity to the valve manifold outlets, to reduce noise.

A small filter may be provided inside the valve manifold gases inlet 4017 inlet to prevent the introduction of dust or particulates into the valve.

An end of the valve manifold corresponding to the gases inlet 4015 is arranged to receive and connect to a connector 4031. In the form shown, the connector 4031 is a swivel connector. Alternatively, the connector 4031 may be arranged such that a gases inlet 4033 of the connector can move in a different way, such as a translational movement or pivoting movement for example.

The valve module 4001 is located at the start of the flow path of the apparatus. If the valve 4003 was to be obstructed (i.e. by dust, particulate, etc.) such that it would be held open, excess pressurized oxygen or other gas would 'dump' out ambient air entry opening(s) in the valve carrier 4051 (e.g. the opening shown beneath the swivel connector in FIG. 26). This would prevent any excess pressure reaching the patient. As such, the system may be considered inherently pressure limited without the use of a pressure relief valve.

Opening(s) 4051O are provided in the valve carrier 4051 to allow ambient air to be drawn in to the gas flow path of the apparatus. The ambient air flow path passes near or adjacent to the valve. In the form shown, the opening 4051O is located around the gases inlet of the swivel connector. Additionally, or alternatively, the opening may be located elsewhere in the valve carrier. When the blower motor 402 of the apparatus is operated, that will create suction through the filter module and valve module, to suck ambient air into the apparatus. The ambient air flow path passes through the valve module and allows ambient air to be entrained with the flow of gas from the flow control valve. The ambient air flow path has a gas outlet adapted to deliver ambient air such that it flows past one or more temperature sensors of the apparatus for delivering a flow of gas.

The apparatus may simultaneously draw in gas from the gases inlet of the valve manifold and ambient air, or the pressurization of gas from the gases inlet may force that gas through the filter. The gases will exit the valve module and enter the gases inlets in the filter. The apparatus may be configured such that the gas from the gases inlet and the ambient air are dynamically entrained/mixed in the apparatus prior to being delivered to the gases outlet of the apparatus.

The valve module may be configured to minimize pressure drop across the valve module by having one or more of: the large opening 4051O for ambient air located around the swivel connector and/or elsewhere; radiuses/rounded/sloped edges in the flow path (i.e. inside the valve manifold, for example) to minimize turbulence and smooth flow.

This valve module 4001 described herein are arranged to directly couple with the filter 1001 to provide a gas flow path from the valve module to the filter. A hose connection is not required between the valve module and the filter module. This minimizes the size of the components and makes it easy to connect and disconnect the modular valve module and filter module.

The filter modules and valve modules described herein may provide varying gas flow paths for the apparatus. For example, the valve module may control the flow of oxygen entering the gas flow path of the apparatus, via the valve module and filter module. Alternatively, the valve module may be bypassed by means of direct connection of an alternative oxygen source to the filter module by the first sub-compartment gases inlet (inlet 1011 of FIG. 13 for example). This may be practical in circumstances where a user may wish to manually adjust the oxygen supply (i.e. such as by the wall supply rotameter).

It will be appreciated that the filter modules and the valve modules described herein may be used separately in apparatuses for delivering a flow of gas. Alternatively, the filter and the valve module may be used together as a filer and valve assembly for improved functionality.

In the configurations shown, the apparatus 10 receives oxygen by at least one of the following: via the valve module (for automatic oxygen regulation by the apparatus), or via the alternative gases inlet provided on the top of the filter (allowing attachment of a manually adjustable oxygen supply—i.e. such as by the wall supply rotameter).

The various configurations described are exemplary configurations only. Any one or more features from any of the configurations may be used in combination with any one or more features from any of the other configurations.

For example, the swivel connector used in the valve module may have additional functionality. In some configurations, the swivel connector may be arranged to swivel about more than one axis; and may for example have two adjacent swivel connection portions with swivel axes that are transverse to each other, so that the gases inlet of the swivel connector can rotate around the two axes. In some configurations, the swivel connector may comprise a ball and socket arrangement or similar, to enable the gases inlet of the swivel connector to rotate in substantially any direction. In some configurations, the swivel connector may be arranged to provide both swiveling and translational movement; so that the gases inlet of the swivel connector may both swivel about one or more axes and may also travel linearly for example. This may be practical for translating the gases inlet from one portion of the apparatus to another, such as from one side of the apparatus to the other of the apparatus for example. In some configurations, the gases inlet may be arranged to translate instead of rotate.

As another example, while the motor and/or sensor sub-assembly recess is described as being in the underside of the main housing, it could alternatively be in a rear, side, front, or top of the housing. With such a variant, the air and/or oxygen inlets may also be positioned differently as required.

As another example, rather than the liquid chamber and chamber bay being configured so that the liquid chamber is inserted into and removed from the chamber bay from a front of the housing, the configuration could be such that the liquid chamber is inserted into and removed from the chamber bay from a side, rear, or top of the housing.

As another example, while the filter modules are described as being inserted into the housing from above and the valve modules inserted into the housing from below, either or both of those components could be inserted into any suitable part of the housing, such as an upper part, lower part, side part, front part, or rear part.

The filter module and valve module are described with reference to a flow therapy apparatus that is capable of delivering heated and humidified gases to a patient or user. The apparatus may be suitable for treating chronic obstructive pulmonary disease (COPD). The apparatus may be configured to deliver gases to a patient interface at a high flow rate (high flow therapy), particularly nasal high flow therapy.

Alternatively, the filter module and/or valve module may be used in an apparatus for a different purpose. The apparatus may be a high flow therapy apparatus, or may be a low flow therapy apparatus. The features may also be provided in an apparatus for providing continuous positive airway pressure (CPAP), which may deliver gases (humidified or otherwise) at positive pressure.

The filter module and/or valve module may alternatively be used with an apparatus that does not require a humidifier and therefore does not require the liquid chamber 300 or chamber bay 108 features. For example, it will be appreciated that the configuration that isolates the motor and gas flow path from the electrical and electronic components has broad applications in other types of gas delivery apparatuses.

The 'flow therapy apparatus' language is intended to cover all such variants.

Reference to any prior art in this specification is not, and should not be taken as, an acknowledgement or any form of suggestion that the prior art forms part of the common general knowledge in the field of endeavor in any country in the world.

Where reference is used herein to directional terms such as 'up', 'down', 'forward', 'rearward', 'horizontal', 'vertical' etc., those terms refer to when the apparatus is in a typical in-use position, and are used to show and/or describe relative directions or orientations.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The terms "approximately," "about," and "substantially" as used herein represent an amount close to the stated amount that still performs a desired function or achieves a desired result. For example, in some embodiments, as the context may permit, the terms "approximately", "about", and "substantially" may refer to an amount that is within less than or equal to 10% of, within less than or equal to 5% of, and within less than or equal to 1% of the stated amount.

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. A respiratory apparatus that provides a flow of gases to a patient, the respiratory apparatus comprising:
   an ambient air inlet;
   a supplemental inlet for receiving supplemental gases from a supplemental gases source;
   a valve, wherein the valve requires a minimum amount of current in order to open;
   a gases composition sensor configured to measure gases composition of mixed flow of ambient air and supplemental gases;
   a main controller configured to control delivery of gases to the patient, the controller configured to:
      adjust actuation of a valve opening by controlling valve current; and activate a coarse controller when a target flow rate of supplemental gas is increased from zero;
a coarse controller configured to:
control actuation of the valve opening by controlling the valve current, wherein the main controller or the coarse controller can control the valve current;
iteratively increases current supplied to the valve; and
switch control of the actuation of the valve to the main controller after flow through the valve is detected.

2. The respiratory apparatus of claim 1, wherein prior to iteratively increasing the valve current, the controller sets the valve current at an initial value.

3. The respiratory apparatus of claim 2, wherein the initial value corresponds to the minimum possible current required to open the valve opening of the valve.

4. The respiratory apparatus of claim 1, wherein at each iteration of the coarse controller, the controller executes a step change in the valve current.

5. The respiratory apparatus of claim 4, wherein the size of step change increases at each iteration.

6. The respiratory apparatus of claim 4, wherein the size of step change is based at least in part on a target FdO2.

7. The respiratory apparatus of claim 4, wherein the size of step change is based at least in part on total flow rate.

8. The respiratory apparatus of claim 1, comprises a gases composition sensor.

9. The respiratory apparatus of claim 8, wherein flow through the valve is detected using the gases composition sensor.

10. The respiratory apparatus of claim 8, wherein flow through the valve is determined to be occurring when the concentration of supplemental gas exceeds ambient levels.

11. The respiratory apparatus of claim 8, wherein flow through the valve is determined to be occurring when the concentration of supplemental gas exceeds ambient levels by an amount greater than the potential sensor error.

12. The respiratory apparatus of claim 1, wherein the supplemental gases comprise concentrated oxygen.

* * * * *